(12) United States Patent
Tsuchiya et al.

(10) Patent No.: US 12,705,705 B2
(45) Date of Patent: Aug. 11, 2026

(54) RADIOGRAPHIC IMAGE PROCESSING METHOD, MACHINE-LEARNING METHOD, TRAINED MODEL, MACHINE-LEARNING PREPROCESSING METHOD, RADIOGRAPHIC IMAGE PROCESSING MODULE, RADIOGRAPHIC IMAGE PROCESSING PROGRAM, AND RADIOGRAPHIC IMAGE PROCESSING SYSTEM

(71) Applicant: HAMAMATSU PHOTONICS K.K., Hamamatsu (JP)

(72) Inventors: Satoshi Tsuchiya, Hamamatsu (JP); Tatsuya Onishi, Hamamatsu (JP); Toshiyasu Suyama, Hamamatsu (JP)

(73) Assignee: HAMAMATSU PHOTONICS K.K., Hamamatsu (JP)

( * ) Notice: Subject to any disclaimer, the term of this patent is extended or adjusted under 35 U.S.C. 154(b) by 304 days.

(21) Appl. No.: 18/270,897

(22) PCT Filed: Oct. 7, 2021

(86) PCT No.: PCT/JP2021/037173
§ 371 (c)(1),
(2) Date: Jul. 5, 2023

(87) PCT Pub. No.: WO2022/172506
PCT Pub. Date: Aug. 18, 2022

(65) Prior Publication Data

US 2024/0054617 A1 Feb. 15, 2024

(30) Foreign Application Priority Data

Feb. 15, 2021 (JP) ................................ 2021-021673

(51) Int. Cl.
*G06T 5/70* (2024.01)
*A61B 6/00* (2006.01)
*A61B 6/42* (2024.01)

(52) U.S. Cl.
CPC ............. *G06T 5/70* (2024.01); *A61B 6/4291* (2013.01); *A61B 6/5258* (2013.01);
(Continued)

(58) Field of Classification Search
None
See application file for complete search history.

(56) References Cited

U.S. PATENT DOCUMENTS 5,335,260 A 8/1994 Arnold
5,565,678 A 10/1996 Manian
(Continued)

FOREIGN PATENT DOCUMENTS

CN 102297873 A 12/2011
CN 102577356 A 7/2012
(Continued)

OTHER PUBLICATIONS

International Preliminary Report on Patentability mailed Aug. 24, 2023 for PCT/JP2021/037173.
(Continued)

*Primary Examiner* — Jiangeng Sun
(74) *Attorney, Agent, or Firm* — Faegre Drinker Biddle & Reath LLP

(57) ABSTRACT

A control device 20 includes an image acquisition unit 203 configured to acquire a radiographic image obtained by irradiating a subject F with radiation and capturing an image of the radiation passing through the subject F, a noise map generation unit 204 configured to derive an evaluation value obtained by evaluating spread of a noise value from a pixel value of each pixel in the radiographic image on the basis of
(Continued)

relationship data indicating a relationship between the pixel value and the evaluation value and generate a noise map that is data in which the derived evaluation value is associated with each pixel in the radiographic image, and a processing unit 205 configured to input the radiographic image and the noise map to a trained model 207 constructed in advance through machine learning and execute image processing of removing noise from the radiographic image.

19 Claims, 33 Drawing Sheets

(52) U.S. Cl.
CPC ............... *G06T 2207/10116* (2013.01); *G06T 2207/20081* (2013.01); *G06T 2207/20084* (2013.01)

(56) References Cited

U.S. PATENT DOCUMENTS

| | | | | |
|---|---|---|---|---|
| 5,585,603 | A | 12/1996 | Vogeley, Jr. | |
| 5,687,210 | A | 11/1997 | Maitrejean et al. | |
| 5,917,877 | A | 6/1999 | Chiabrera et al. | |
| 6,173,038 | B1 | 1/2001 | Siffert et al. | |
| 6,198,795 | B1 | 3/2001 | Naumann et al. | |
| 6,201,850 | B1 | 3/2001 | Heumann | |
| 6,231,231 | B1 | 5/2001 | Farrokhnia | |
| 6,269,142 | B1 | 7/2001 | Smith | |
| 6,315,447 | B1 | 11/2001 | Nord et al. | |
| 6,347,131 | B1 | 2/2002 | Gusterson | |
| 6,370,223 | B1 | 4/2002 | Gleason et al. | |
| 6,398,408 | B1 | 6/2002 | Polkus | |
| 6,516,045 | B2 | 2/2003 | Shepherd et al. | |
| 6,570,955 | B1 | 5/2003 | Siffert et al. | |
| 6,574,302 | B2 | 6/2003 | Adriaansz | |
| 6,574,303 | B2 | 6/2003 | Sawada | |
| 6,600,805 | B2 | 7/2003 | Hansen | |
| 6,632,020 | B2 | 10/2003 | Kaufhold et al. | |
| 6,661,868 | B2 | 12/2003 | Sawada | |
| 6,872,949 | B2 | 3/2005 | Mizuoka et al. | |
| 7,260,177 | B2 | 8/2007 | Hirose | |
| 7,311,440 | B2 | 12/2007 | Yoon et al. | |
| 7,467,892 | B2 | 12/2008 | Lang et al. | |
| 7,477,726 | B2 | 1/2009 | Kabumoto | |
| 7,570,787 | B2 | 8/2009 | Hirose | |
| 7,696,480 | B2 | 4/2010 | Kostka et al. | |
| 7,746,976 | B2 | 6/2010 | Huo et al. | |
| 7,980,760 | B2 | 7/2011 | Kabumoto et al. | |
| 7,991,110 | B2 | 8/2011 | Hirose | |
| 8,068,656 | B2 | 11/2011 | Hirose | |
| 8,077,827 | B2 | 12/2011 | Perng | |
| 8,223,922 | B2 | 7/2012 | Suyama et al. | |
| 8,280,005 | B2 | 10/2012 | Suyama et al. | |
| 8,858,076 | B2 | 10/2014 | Quintana et al. | |
| 8,873,825 | B2 | 10/2014 | Mercuriev | |
| 8,938,110 | B2 | 1/2015 | Goshen et al. | |
| 8,989,345 | B2 | 3/2015 | Kim et al. | |
| 9,413,995 | B2 | 8/2016 | Ohguri | |
| 9,547,889 | B2 | 1/2017 | Goshen | |
| 9,615,808 | B2 | 4/2017 | Mentrup et al. | |
| 9,619,906 | B2 | 4/2017 | Choi et al. | |
| 9,886,765 | B2 | 2/2018 | Naito | |
| 9,943,282 | B2 | 4/2018 | Katsumata | |
| 10,010,304 | B2 * | 7/2018 | Morita .................. | G16H 50/20 |
| 10,242,443 | B2 | 3/2019 | Hsieh et al. | |
| 10,430,708 | B1 | 10/2019 | Hu et al. | |
| 10,697,904 | B2 | 6/2020 | Yamakawa et al. | |
| 10,803,555 | B2 | 10/2020 | Song et al. | |
| 10,820,197 | B2 | 10/2020 | Rosenberg et al. | |
| 10,824,857 | B2 | 11/2020 | Flohr et al. | |
| 10,832,381 | B2 | 11/2020 | Strobel et al. | |
| 10,888,296 | B2 | 1/2021 | Ji et al. | |
| 10,949,951 | B2 | 3/2021 | Tang et al. | |
| 10,970,887 | B2 | 4/2021 | Wang et al. | |
| 10,984,564 | B2 | 4/2021 | Bergner et al. | |
| 11,079,344 | B2 | 8/2021 | Suyama et al. | |
| 11,126,914 | B2 | 9/2021 | Thibault et al. | |
| 11,166,994 | B2 | 11/2021 | Lichtenstein et al. | |
| 11,185,302 | B2 | 11/2021 | Tsuchiya et al. | |
| 11,195,277 | B2 | 12/2021 | Shanbhag et al. | |
| 11,244,480 | B2 | 2/2022 | Teshigawara et al. | |
| 11,257,196 | B2 | 2/2022 | Kaneko et al. | |
| 11,324,472 | B2 | 5/2022 | Hamill | |
| 11,386,592 | B2 | 7/2022 | Paysan et al. | |
| 11,436,720 | B2 | 9/2022 | Gong et al. | |
| 11,501,431 | B2 | 11/2022 | Xiao et al. | |
| 11,517,197 | B2 | 12/2022 | Zhou et al. | |
| 11,574,170 | B2 | 2/2023 | Isogawa et al. | |
| 11,710,230 | B2 | 7/2023 | Takeshima et al. | |
| 11,798,159 | B2 | 10/2023 | Zhou et al. | |
| 11,972,559 | B2 | 4/2024 | Hamauzu | |
| 12,094,037 | B2 * | 9/2024 | Takahashi ............. | G06T 11/008 |
| 12,141,965 | B2 | 11/2024 | Mao et al. | |
| 12,167,926 | B2 | 12/2024 | Nishii et al. | |
| 12,243,127 | B2 | 3/2025 | Lee et al. | |
| 2005/0078802 | A1 | 4/2005 | Lang et al. | |
| 2011/0206177 | A1 * | 8/2011 | Hirasawa ............... | A61B 6/542 378/16 |
| 2012/0224760 | A1 | 9/2012 | Goshen et al. | |
| 2013/0051516 | A1 * | 2/2013 | Yang ..................... | G06T 11/005 378/4 |
| 2013/0051527 | A1 | 2/2013 | Sakaguchi et al. | |
| 2013/0071876 | A1 | 3/2013 | Hao et al. | |
| 2015/0342554 | A1 | 12/2015 | Mentrup et al. | |
| 2015/0371414 | A1 | 12/2015 | Choi et al. | |
| 2017/0065244 | A1 | 3/2017 | Taki | |
| 2018/0122094 | A1 * | 5/2018 | Naito .................. | A61B 6/5282 |
| 2018/0349759 | A1 | 12/2018 | Isogawa et al. | |
| 2019/0035058 | A1 | 1/2019 | Strobel et al. | |
| 2019/0102621 | A1 | 4/2019 | Flohr et al. | |
| 2019/0108441 | A1 | 4/2019 | Thibault et al. | |
| 2019/0201106 | A1 | 7/2019 | Siemionow et al. | |
| 2019/0325621 | A1 | 10/2019 | Wang et al. | |
| 2019/0385345 | A1 * | 12/2019 | Bergner ................ | G06T 11/006 |
| 2020/0065940 | A1 | 2/2020 | Tang et al. | |
| 2020/0241150 | A1 * | 7/2020 | Ikeda .................... | H10F 39/189 |
| 2020/0286214 | A1 * | 9/2020 | Kaneko ................. | G06T 11/003 |
| 2020/0315566 | A1 | 10/2020 | Takagi | |
| 2021/0059629 | A1 | 3/2021 | Hamill | |
| 2021/0251583 | A1 * | 8/2021 | Hamauzu ............... | A61B 17/29 |
| 2022/0313199 | A1 | 10/2022 | Nishii et al. | |
| 2023/0135988 | A1 | 5/2023 | Onishi et al. | |
| 2023/0136930 | A1 | 5/2023 | Suyama et al. | |

FOREIGN PATENT DOCUMENTS

| | | | |
|---|---|---|---|
| CN | 103649990 | A | 3/2014 |
| CN | 106233127 | A | 12/2016 |
| CN | 107516330 | A | 12/2017 |
| CN | 107533019 | A | 1/2018 |
| CN | 107595312 | A | 1/2018 |
| CN | 107871332 | A | 4/2018 |
| CN | 108139489 | A | 6/2018 |
| CN | 108271411 | A | 7/2018 |
| CN | 108926353 | A | 12/2018 |
| CN | 109544477 | A | 3/2019 |
| CN | 109697476 | A | 4/2019 |
| CN | 109805950 | A | 5/2019 |
| CN | 109983325 | A | 7/2019 |
| CN | 115398215 | A | 11/2022 |
| JP | 2001-099941 | A | 4/2001 |
| JP | 2003-167060 | A | 6/2003 |
| JP | 2006-318103 | A | 11/2006 |
| JP | 2008-229161 | A | 10/2008 |
| JP | 2013-512024 | A | 4/2013 |
| JP | 2018-117900 | A | 8/2018 |
| JP | 2018-206382 | A | 12/2018 |
| JP | 6454820 | B1 | 1/2019 |
| JP | 2019-045235 | A | 3/2019 |
| JP | 2019-068912 | A | 5/2019 |
| JP | 2019-091393 | A | 6/2019 |
| JP | 2019-111322 | A | 7/2019 |

(56) References Cited

FOREIGN PATENT DOCUMENTS

| | | | | | |
|---|---|---|---|---|---|
| JP | 2019-158663 | A | | 9/2019 | |
| JP | 2019-168360 | A | | 10/2019 | |
| JP | 2019-202087 | A | | 11/2019 | |
| JP | 2019-208990 | A | | 12/2019 | |
| JP | 2019-535451 | A | | 12/2019 | |
| JP | 2020-096646 | A | | 6/2020 | |
| JP | 2020-141908 | A | | 9/2020 | |
| KR | 2013-0096658 | A | | 8/2013 | |
| TW | 200801571 | A | | 1/2008 | |
| TW | 202018431 | A | | 5/2020 | |
| TW | 202113349 | A | | 4/2021 | |
| WO | 2007/114470 | A1 | | 10/2007 | |
| WO | WO-2011/064683 | A2 | | 6/2011 | |
| WO | WO-2013/005805 | A1 | | 1/2013 | |
| WO | 2014/052267 | A1 | | 4/2014 | |
| WO | WO-2018/098077 | A1 | | 5/2018 | |
| WO | WO-2018/104349 | A1 | | 6/2018 | |
| WO | WO-2019/082276 | A1 | | 5/2019 | |
| WO | WO-2019/097796 | A1 | | 5/2019 | |
| WO | WO-2020/031984 | A1 | | 2/2020 | |
| WO | WO-2021210617 | A1 | * | 10/2021 | ............. A61B 6/482 |
| WO | WO-2021210618 | A1 | * | 10/2021 | ........... G01N 23/087 |

OTHER PUBLICATIONS

Zhang et al, "FFDNet: Toward a Fast and Flexible Solution for CNN based Image Denoising", arxiv.org, Cornell University Library, 201 Olin Library, Cornell University, Ithaca, NY 14853, Oct. 11, 2017, XP081150272.

Abramova et al, "Analysis of Noise Properties in Dental Images", 2020 IEEE 40th International Conference On Electronics and Nanotechnology (ELNANO), Apr. 22, 2020 May 6, 2020, p. 511-p. 515, XP033769133.

Lu Qiu_hong et al., "Fault detecting technology based on neural netwom: algorithm", Optics and Precision Engineering, Feb. 2002, vol. 10, No. 1, p. 25-p. 30 May 29, 2025.

Li Wei, "High-resolution X-ray digital radiography of electronic industry", School of Information Engineering, Chang'an University, Xi'an 710064, China, Jul. 2012, vol. 33, No. 4, p. 654-p. 659.

Notice of Allowance issued Apr. 18, 2025 in U.S. Appl. No. 17/918,397.

Hideki Kato, et al., "A Presumption Calculating Formula of the X-ray Spectrum Generated from a Molybdenum Target X-ray Tube", The Journal of the Japan Society of Radiological Technology, Mar. 31, 2011, p. 193-p. 201.

Kenzo Isogawa et al., "Deep Shrinkage Convolutional Neural Network for Adaptive Noise Reduction", IEEE Signal Processing Letters, vol. 25, No. 2, Feb. 1, 2018, p. 224-p. 228, XP055508221.

Xiao-Ping Zhang et al., "Thresholding Neural Network for Adaptive Noise Reduction", IEEE Transactions On Neural Networks, IEEE Service Center, Piscataway, NJ, US, vol. 12, No. 3, May 1, 2001, p. 567-p. 584, XP011039623.

Notice of Allowance dated Jul. 16, 2025 that issued in U.S. Appl. No. 17/918,397.

International Preliminary Report on Patentability mailed Oct. 27, 2022 for PCT/JP2021/015464.

International Preliminary Report on Patentability mailed Oct. 27, 2022 for PCT/JP2021/015488.

International Preliminary Report on Patentability mailed Oct. 27, 2022 for PCT/JP2021/015489.

Sungmin Cha et al., "Proceedings of the IEEE/CVF International Conference on Computer Vision (ICCV)", IEEE/CVF, 2019, p. 4160-p. 4169.

U.S. Final Office Action issued Oct. 24, 2024 in U.S. Appl. No. 17/918,397.

Sungmin Cha et al, "Fully Convolutional Pixel Adaptive Image Denoiser", arxiv.org, Cornell University Library, 201 Olin Library Cornell University Ithaca, NY 14853, Jul. 19, 2018, p. 1-p. 19, XP081114501.

Yuewen Sun, "Digital radiography image denoising using a generative adversarial network", Journal of X-Ray Science and Technology, vol. 26, No. 4, Aug. 10, 2018, p. 523-p. 534, XP93154123.

Notice of Allowance dated Sep. 23, 2025 that issued in U.S. Appl. No. 17/918,397.

Notice of Allowance dated Aug. 5, 2025 that issued in U.S. Appl. No. 17/918,397.

Office action received from European patent application No. 21789365.0 mailed on Feb. 16, 2026, 7 pages.

Tabary et al., "New Functionalities in "SINDBAD" Software for Realistic XRay Simulation Devoted to Complex Parts Inspection", 9th European Conference on NDT, XP093363902, Sep. 25, 2006, pp. 1-12.

* cited by examiner

1
F
TD
19
11a
12a
50
51
11b
12b
13
SENSOR CONTROL UNIT
AMPLIFIER
14a
AMPLIFIER
14b
AMPLIFIER CONTROL UNIT
18
15a
15b
60
CORRECTION CIRCUIT
16a
CORRECTION CIRCUIT
16b
OUTPUT INTERFACE
17a
OUTPUT INTERFACE
17b
10
CONTROL DEVICE
20
DISPLAY DEVICE
30
INPUT DEVICE
40

(a)
G14
ENERGY
(b)
G15
ENERGY
(c)
G16
ENERGY
(d)
G17
ENERGY

Fig. 14

| SPECTRUM | G14 | G15 | G16 | G17 |
| --- | --- | --- | --- | --- |
| THICKNESS | 0mm | 10mm | 20mm | 30mm |
| AVERAGE ENERGY | 17keV | 24keV | 26keV | 27keV |
| TRANSMITTANCE | 1 | 0.4 | 0.2 | 0.1 |

G26
G1
G1
0
PIXEL POSITION
G2
STANDARD DEVIATION OF NOISE VALUES
PIXEL POSITION
G27
STANDARD DEVIATION OF NOISE VALUES
PIXEL VALUE
G5
G5
0
PIXEL POSITION
G4
STANDARD DEVIATION OF NOISE VALUES
PIXEL POSITION

RADIOGRAPHIC IMAGE PROCESSING METHOD, MACHINE-LEARNING METHOD, TRAINED MODEL, MACHINE-LEARNING PREPROCESSING METHOD, RADIOGRAPHIC IMAGE PROCESSING MODULE, RADIOGRAPHIC IMAGE PROCESSING PROGRAM, AND RADIOGRAPHIC IMAGE PROCESSING SYSTEM

TECHNICAL FIELD

One aspect of an embodiment relates to a radiographic image processing method, a machine-learning method, a trained model, a machine-learning preprocessing method, a radiographic image processing module, a radiographic image processing program, and a radiographic image processing system.

BACKGROUND ART

Since the past, a method of removing noise from image data using a trained model through machine learning has been known (see, for example, Patent Literature 1). According to this method, noise from the image data is automatically removed, and thus it is possible to observe a subject with high accuracy.

CITATION LIST

Patent Literature

[Patent Literature 1] Japanese Unexamined Patent Publication No. 2019-91393

SUMMARY OF INVENTION

Technical Problem

In the method of the related art as described above, noise may not be sufficiently removed in a case where a radiographic image generated by transmitting radiation such as X-rays through a subject is used as a target. For example, a relationship between pixel values and noise in an image has a tendency to fluctuate depending on the conditions of a radiation source such as an X-ray source, the type of filter being used, and the like, and the noise tends to be difficult to remove effectively.

Consequently, one aspect of an embodiment was contrived in view of such a problem, and an object thereof is to provide a radiographic image processing method, a machine-learning method, a trained model, a machine-learning preprocessing method, a radiographic image processing module, a radiographic image processing program, and a radiographic image processing system that make it possible to effectively remove noise from a radiographic image.

Solution to Problem

According to one aspect of an embodiment, there is provided a radiographic image processing method including: an image acquisition step of acquiring a radiographic image obtained by irradiating a subject with radiation and capturing an image of the radiation passing through the subject; a noise map generation step of deriving an evaluation value obtained by evaluating spread of a noise value from a pixel value of each pixel in the radiographic image on the basis of relationship data indicating a relationship between the pixel value and the evaluation value, and generating a noise map that is data in which the derived evaluation value is associated with each pixel in the radiographic image; and a processing step of inputting the radiographic image and the noise map to a trained model constructed in advance through machine learning and executing image processing of removing noise from the radiographic image.

Alternatively, according to another aspect of an embodiment, there is provided a radiographic image processing module including: an image acquisition unit configured to acquire a radiographic image obtained by irradiating a subject with radiation and capturing an image of the radiation passing through the subject; a noise map generation unit configured to derive an evaluation value obtained by evaluating spread of a noise value from a pixel value of each pixel in the radiographic image on the basis of relationship data indicating a relationship between the pixel value and the evaluation value and generate a noise map that is data in which the derived evaluation value is associated with each pixel in the radiographic image; and a processing unit configured to input the radiographic image and the noise map to a trained model constructed in advance through machine learning and execute image processing of removing noise from the radiographic image.

Alternatively, according to another aspect of an embodiment, there is provided a radiographic image processing program causing a processor to function as: an image acquisition unit configured to acquire a radiographic image obtained by irradiating a subject with radiation and capturing an image of the radiation passing through the subject; a noise map generation unit configured to derive an evaluation value obtained by evaluating spread of a noise value from a pixel value of each pixel in the radiographic image on the basis of relationship data indicating a relationship between the pixel value and the evaluation value and generate a noise map that is data in which the derived evaluation value is associated with each pixel in the radiographic image; and a processing unit configured to input the radiographic image and the noise map to a trained model constructed in advance through machine learning and execute image processing of removing noise from the radiographic image.

Alternatively, according to another aspect of an embodiment, there is provided a radiographic image processing system including: the above radiographic image processing module; a source configured to irradiate the subject with radiation; and an imaging device configured to capture an image of the radiation passing through the subject and acquire the radiographic image.

According to the one aspect or the other aspects, an evaluation value is derived from the pixel value of each image in a radiographic image on the basis of the relationship data indicating the relationship between the pixel value and the evaluation value obtained by evaluating the spread of a noise value, and a noise map that is data in which the derived evaluation value is associated with each pixel in the radiographic image is generated. A radiographic image and a noise map are input to a trained model constructed in advance through machine learning, and image processing of removing noise from the radiographic image is executed. With such a configuration, the noise in each pixel in the radiographic image is removed through machine learning in consideration of the spread of the noise value evaluated from the pixel value of each pixel in the radiographic image. This makes it possible to realize noise removal corresponding to the relationship between the pixel value and the spread of noise in the radiographic image using the trained model. As a result, it is possible to effectively remove noise in the radiographic image.

Advantageous Effects of Invention

According to an aspect of the present disclosure, it is possible to effectively remove noise in a radiographic image of a subject.

BRIEF DESCRIPTION OF DRAWINGS

FIG. 14 is a table illustrating an example of simulation calculation results of a relationship between the thickness of a subject and average energy and transmittance obtained by the calculation unit 202A of FIG. 11.

FIG. 27 is a block diagram illustrating a functional configuration of an X-ray detection camera 10C of FIG. 25.

DESCRIPTION OF EMBODIMENTS

Hereinafter, embodiments of the present disclosure will be described in detail with reference to the accompanying drawings. Meanwhile, in the description, the same elements or elements having the same function are denoted by the same reference signs, and thus duplicate description will be omitted.

First Embodiment

Figure 1:
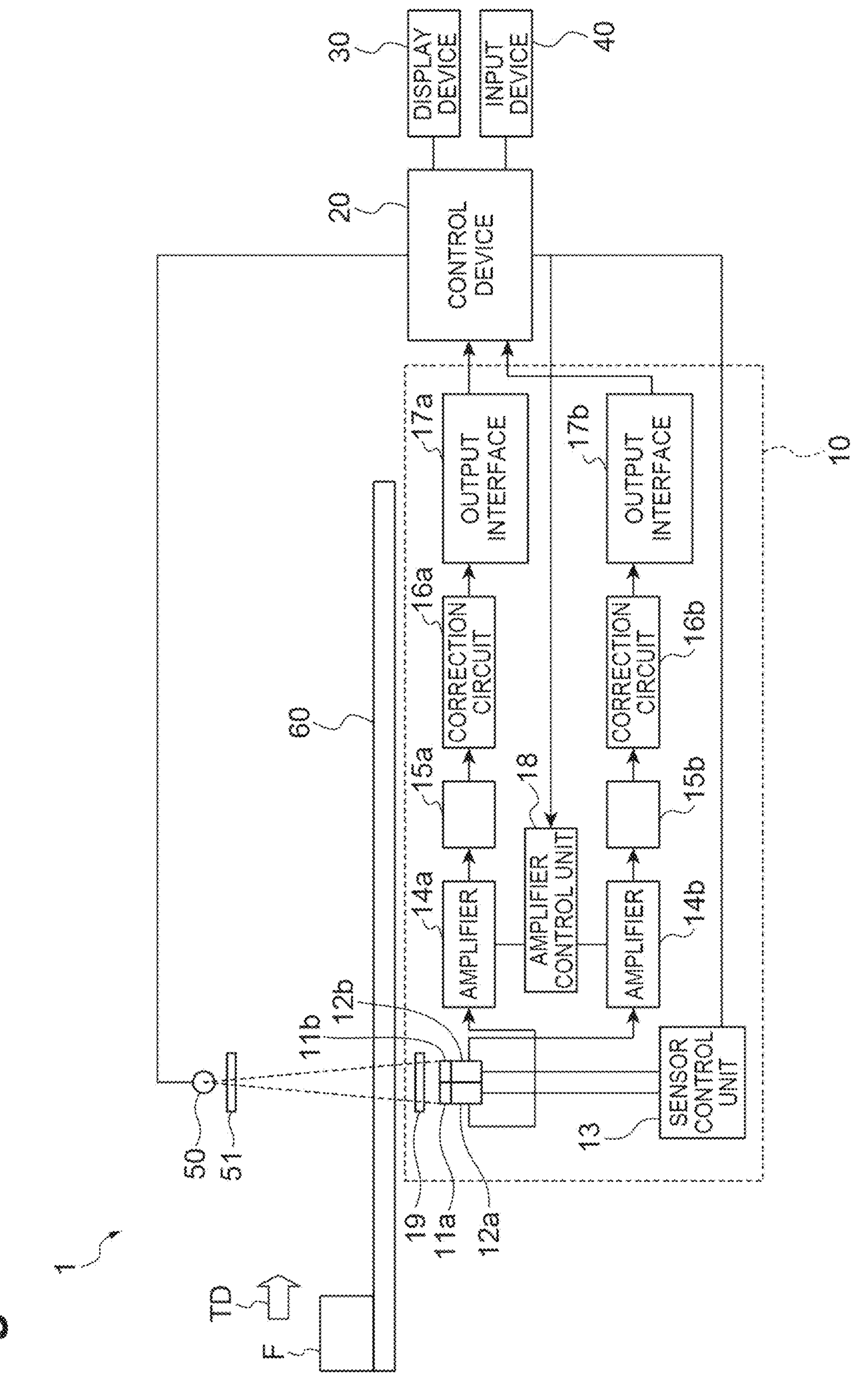
FIG. 1 is a schematic configuration diagram of an image acquisition device 1 according to an embodiment.

FIG. 1 is a configuration diagram of an image acquisition device 1 which is a radiographic image processing system according to a first embodiment. As shown in FIG. 1, the image acquisition device 1 is a device that irradiates a subject F transported in a transport direction TD with X-rays (radiation) and acquires an X-ray image (radiographic image) obtained by capturing an image of the subject F on the basis of the X-rays passing through the subject F. The image acquisition device 1 performs a foreign substance inspection, a weight inspection, a product inspection, or the like on the subject F using an X-ray image, and examples of the application include a food inspection, a baggage inspection, a substrate inspection, a battery inspection, a material inspection, and the like. The image acquisition device 1 is configured to include a belt conveyor (transport means) 60, X-rays (radiation source) 50, an X-ray detection camera (imaging device) 10, a control device (radiographic image processing module) 20, a display device 30, and an input device 40 for performing various inputs. Meanwhile, the radiographic image in the embodiment of the present disclosure is not limited to an X-ray image, and may also be an image caused by radiation other than X-rays such as γ-rays.

The belt conveyor 60 has a belt portion on which the subject F is placed, and transports the subject F in the transport direction TD at a predetermined transport speed by moving the belt portion in the transport direction TD. The transport speed of the subject F is, for example, 48 m/min. The belt conveyor 60 can change the transport speed as necessary to a transport speed such as, for example, 24 m/min or 96 m/min. In addition, the belt conveyor 60 can appropriately change the height position of the belt portion to change a distance between the X-ray irradiator 50 and the subject F. Meanwhile, examples of the subject F transported by the belt conveyor 60 include foodstuffs such as meat, seafood, agricultural products, or confectionery, rubber products such as tires, resin products, metal products, resource materials such as minerals, waste, and various products such as electronic parts or electronic substrates. The X-ray irradiator 50 is a device that radiates (outputs) X-rays to the subject F as an X-ray source. The X-ray irradiator 50 is a point light source, and diffuses and radiates the X-rays in a predetermined angle range in a fixed irradiation direction. The X-ray irradiator 50 is disposed above the belt conveyor 60 at a predetermined distance from the belt conveyor 60 so that the irradiation direction of the X-rays is directed toward the belt conveyor 60 and the diffused X-rays extend in the entire width direction of the subject F (a direction intersecting the transport direction TD). In addition, in the lengthwise direction of the subject F (a direction parallel to the transport direction TD), the irradiation range of the X-ray irradiator 50 is set as a predetermined division range in the lengthwise direction, and the X-rays are radiated in the entire lengthwise direction of the subject F by the subject F being transported in the transport direction TD by the belt conveyor 60. The tube voltage and tube current of the X-ray irradiator 50 are set by the control device 20. The X-ray irradiator 50 irradiates the belt conveyor 60 with X-rays having predetermined energy and a radiation dose according to the set tube voltage and tube current. In addition, a filter 51 that transmits a predetermined wavelength region of the X-rays is provided in the vicinity of the X-ray irradiator 50 on the belt conveyor 60 side. The filter 51 is not necessarily required and may be omitted as appropriate.

The X-ray detection camera 10 detects X-rays passing through the subject F among the X-rays radiated to the subject F by the X-ray irradiator 50, and outputs a signal based on the X-rays. The X-ray detection camera 10 is a dual-line X-ray camera in which two sets of configurations for detecting X-rays are disposed. In the image acquisition device 1 according to the first embodiment, each X-ray image is generated on the basis of the X-rays detected in each line (a first line and a second line) of the dual-line X-ray camera. By performing average processing, addition processing, or the like on the two generated X-ray images, a clear (high-luminance) image can be acquired with a smaller X-ray dose than in a case where an X-ray image is generated on the basis of the X-rays detected in one line.

The X-ray detection camera 10 includes a filter 19, scintillators 11*a* and 11*b*, line scan cameras 12*a* and 12*b*, a sensor control unit 13, amplifiers 14*a* and 14*b*, AD converters 15*a* and 15*b*, correction circuits 16*a* and 16*b*, output interfaces 17*a* and 17*b*, and an amplifier control unit 18. The scintillator 11*a*, the line scan camera 12*a*, the amplifier 14*a*, the AD converter 15*a*, the correction circuit 16*a*, and the output interface 17*a* are electrically connected to each other, and have components related to the first line. In addition, the scintillator 11*b*, the line scan camera 12*b*, the amplifier 14*b*, the AD converter 15*b*, the correction circuit 16*b*, and the output interface 17*b* are electrically connected to each other, and have components related to the second line. The line scan camera 12*a* of the first line and the line scan camera 12*b* of the second line are disposed side by side in the transport direction TD. Meanwhile, hereinafter, the components of the first line will be described to represent components common to the first line and the second line.

The scintillator 11*a* is fixed on the line scan camera 12*a* by adhesion or the like, and converts the X-rays passing through the subject F into scintillation light. The scintillator 11*a* outputs the scintillation light to the line scan camera 12*a*. The filter 19 transmits a predetermined wavelength region of the X-rays toward the scintillator 11*a*. The filter 19 is not necessarily required and may be omitted as appropriate.

The line scan camera 12*a* detects the scintillation light from the scintillator 11*a*, converts the detected light into electric charge, and outputs it as a detection signal (electrical signal) to the amplifier 14*a*. The line scan camera 12*a* has a plurality of line sensors arranged in parallel in a direction intersecting the transport direction TD. The line sensor is, for example, a charge coupled device (CCD) image sensor, a complementary metal-oxide semiconductor (CMOS) image sensor, or the like, and includes a plurality of photodiodes.

The sensor control unit 13 controls the line scan cameras 12*a* and 12*b* to repeatedly capture images at a predetermined detection period so that the line scan cameras 12*a* and 12*b* can capture an image of X-rays passing through the same region of the subject F. As the predetermined detection period, for example, a period common to the line scan cameras 12*a* and 12*b* may be set on the basis of the distance between the line scan cameras 12*a* and 12*b*, the speed of the belt conveyor 60, the distance between the X-ray irradiator 50 and the subject F on the belt conveyor 60 (focus object distance (FOD)), and the distance between the X-ray irradiator 50 and the line scan cameras 12*a* and 12*b* (focus detector distance (FDD)). In addition, the predetermined period may be individually set on the basis of the pixel width of a photodiode in a direction perpendicular to the arrangement direction of pixels of the line sensors of the line scan cameras 12*a* and 12*b*. In this case, the deviation (delay time) of the detection period between the line scan cameras 12*a* and 12*b* may be specified in accordance with the distance between the line scan cameras 12*a* and 12*b*, the speed of the belt conveyor 60, the distance between the X-ray irradiator 50 and the subject F on the belt conveyor 60 (FOD), and the distance between the X-ray irradiator 50 and the line scan cameras 12*a* and 12*b* (FDD), and individual periods may be set for each. The amplifier 14*a* amplifies the detection signal at a predetermined set amplification factor to generate an amplified signal, and outputs the amplified signal to the AD converter 15*a*. The set amplification factor is an amplification factor which is set by the amplifier control unit 18. The amplifier control unit 18 sets the set amplification factor of the amplifiers 14*a* and 14*b* on the basis of predetermined imaging conditions.

The AD converter 15*a* converts the amplified signal (voltage signal) output by the amplifier 14*a* into a digital signal, and outputs the converted signal to the correction circuit 16*a*. The correction circuit 16*a* performs a predetermined correction such as signal amplification on the digital signal, and outputs the corrected digital signal to the output interface 17*a*. The output interface 17*a* outputs the digital signal to the outside of the X-ray detection camera 10. In FIG. 1, the AD converter, the correction circuit, and the output interface exist individually, but they may be integrated into one.

The control device 20 is a computer such as, for example, a personal computer (PC). The control device 20 generates an X-ray image on the basis of the digital signal (amplified signal) output from the X-ray detection camera 10 (more specifically, the output interfaces 17*a* and 17*b*). The control device 20 generates one X-ray image by performing average processing or addition processing on two digital signals output from the output interfaces 17*a* and 17*b*. The generated X-ray image is output to the display device 30 after a noise removal process to be described later is performed, and is displayed by the display device 30. In addition, the control device 20 controls the X-ray irradiator 50, the amplifier control unit 18, and the sensor control unit 13. Meanwhile, the control device 20 of the first embodiment is a device which is independently provided outside the X-ray detection camera 10, but it may be integrated inside the X-ray detection camera 10.

Figure 2:
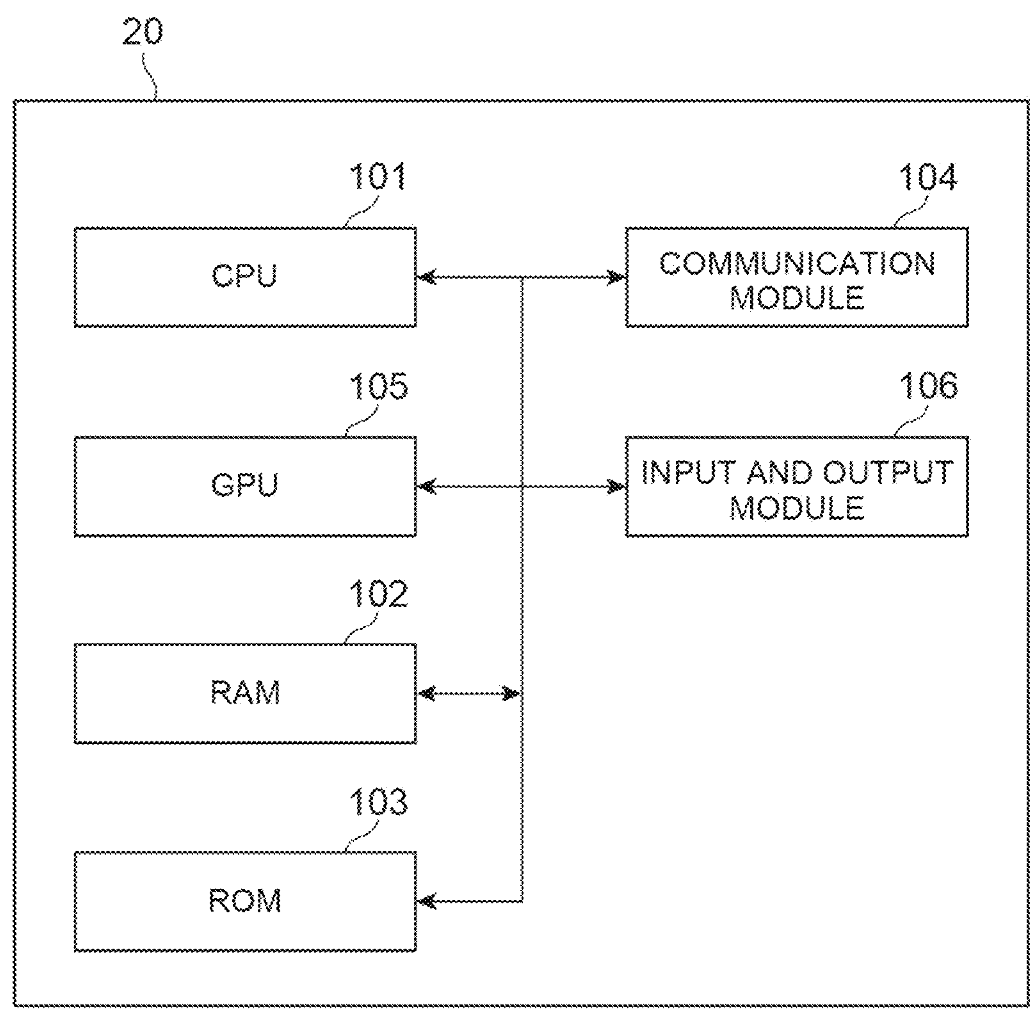
FIG. 2 is a block diagram illustrating an example of a hardware configuration of a control device 20 of FIG. 1.

FIG. 2 shows a hardware configuration of the control device 20. As shown in FIG. 2, the control device 20 is a computer or the like physically including a central processing unit (CPU) 101 and graphic processing unit (GPU) 105 which are processors, a random access memory (RAM) 102 and a read only memory (ROM) 103 which are recording media, a communication module 104, an input and output module 106, and the like, which are electrically connected to each other. Meanwhile, the control device 20 may include a display, a keyboard, a mouse, a touch panel display, and the like as the input device 40 and the display device 30, or may include a data recording device such as a hard disk drive or a semiconductor memory. In addition, the control device may be constituted by a plurality of computers.

Figure 3:
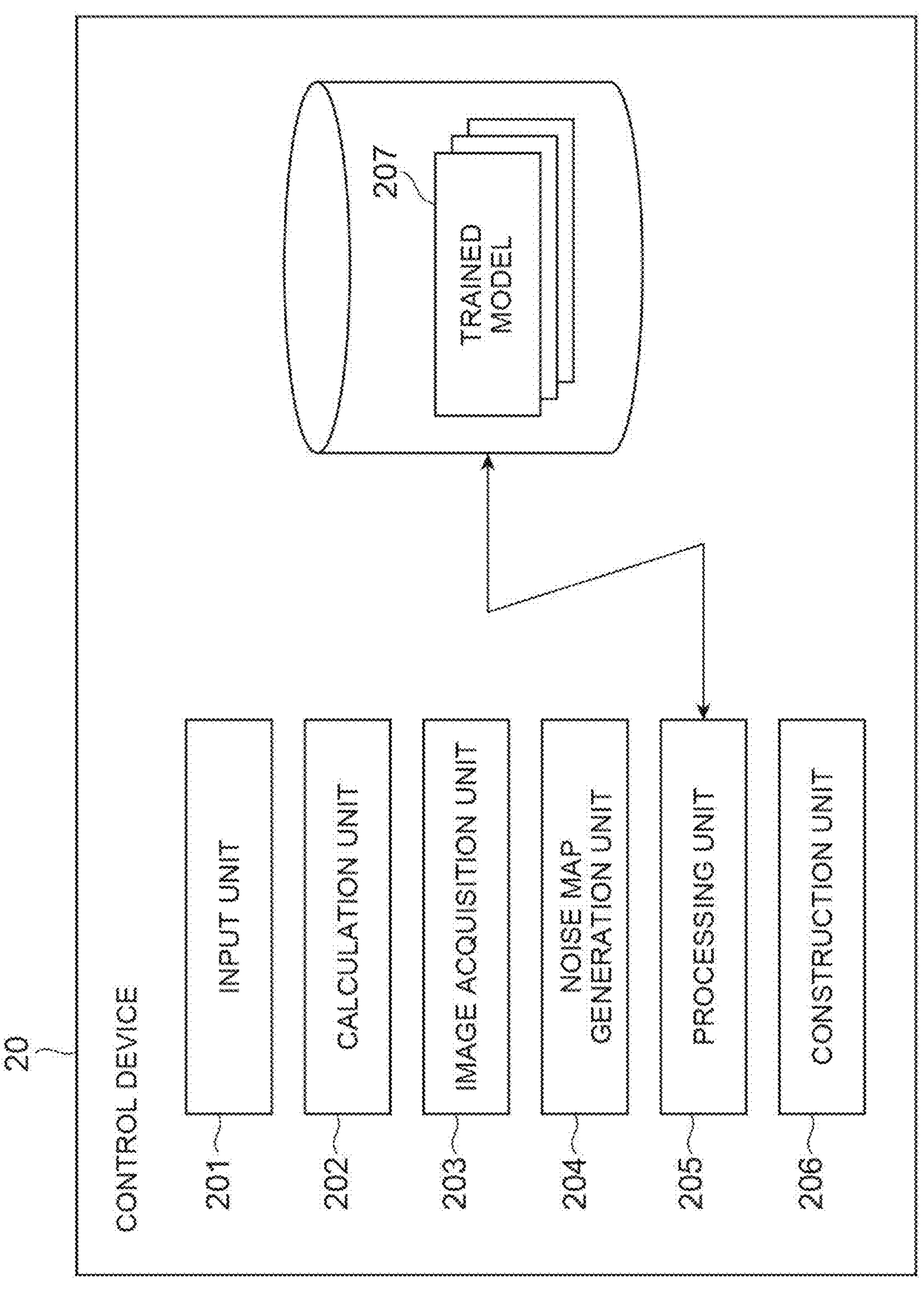
FIG. 3 is a block diagram illustrating a functional configuration of the control device 20 of FIG. 1.

FIG. 3 is a block diagram illustrating a functional configuration of the control device 20. The control device 20 includes an input unit 201, a calculation unit 202, an image acquisition unit 203, a noise map generation unit 204, a processing unit 205, and a construction unit 206. Each functional unit of the control device 20 shown in FIG. 3 is realized by loading a program (a radiographic image processing program of the first embodiment) on the hardware such as the CPU 101, the GPU 105, and the RAM 102 to thereby bring the communication module 104, the input and output module 106, and the like into operation under the control of the CPU 101 and the GPU 105 and read out and write data in the RANI 102. The CPU 101 and the GPU 105 of the control device cause the control device 20 to function as each functional unit in FIG. 3 by executing this computer program, and sequentially execute processing corresponding to a radiographic image processing method to be described later. Meanwhile, the CPU 101 and the GPU 105 may be a single piece of hardware, or only one may be used. In addition, the CPU 101 and the GPU 105 may be implemented in a programmable logic such as an FPGA like a soft processor. The RANI or the ROM may also be a single piece of hardware, or may be built into a programmable logic such as an FPGA. Various types of data required for executing this computer program and various types of data generated by executing this computer program are all stored in a built-in memory such as the ROM 103 or the RANI 102, or a storage medium such as a hard disk drive. In addition, a built-in memory or a storage medium in the control device 20 stores in advance a trained model 207 which is read by the CPU 101 and the GPU 105 and causes the CPU 101 and the GPU 105 to execute noise removal processing on an X-ray image (which will be described later).

The details of the function of each functional unit of the control device 20 will be described below.

The input unit 201 accepts an input of condition information indicating either the conditions of the radiation source or the imaging conditions when radiation is radiated to capture an image of the subject F. Specifically, the input unit 201 accepts an input of condition information indicating the operating conditions of the X-ray irradiator (radiation source) 50 when the X-ray image of the subject F is captured, the imaging conditions of the X-ray detection camera 10, or the like from a user of the image acquisition device 1. Examples of the operating conditions include all or some of a tube voltage, a target angle, a target material, and the like. Examples of the operating conditions include all or some of a tube voltage, a target angle, a target material, and the like. Examples of the condition information indicating the imaging conditions include the material and thickness of the filters 51 and 19 disposed between the X-ray irradiator 50 and the X-ray detection camera 10, the distance (FDD) between the X-ray irradiator 50 and the X-ray detection camera 10, the type of window material of the X-ray detection camera 10, and all or some of information relating to the material and thickness of the scintillators 11*a* and 11*b* of the X-ray detection camera 10, X-ray detection camera information (for example, a gain setting value, a circuit noise value, an amount of saturated charge, a conversion coefficient value (e-/count), and the line rate (Hz) or line speed (m/min) of the camera), information on the subject F, and the like. The input unit 201 may accept an input of the condition information as a direct input of information such as numerical values, or may accept the input as a selective input for information such as numerical values which are set in an internal memory in advance. The input unit 201 accepts the input of the above condition information from a user, but it may acquire some condition information (such as a tube voltage) in accordance with the detection result of the state of control performed by the control device 20.

The calculation unit 202 calculates the average energy related to the X-rays (radiation) passing through the subject F on the basis of the condition information. The condition information includes at least any one of the tube voltage of the source, information relating to the subject F, information on a filter included in a camera used to capture an image of the subject F, information on a scintillator included in the camera, and information on a filter included in the X-ray source. Specifically, the calculation unit 202 calculates the value of the average energy of X-rays passing through the subject F and detected by the X-ray detection camera 10 using the image acquisition device 1 on the basis of the condition information whose input is accepted by the input unit 201. For example, the calculation unit 202 calculates an X-ray spectrum detected by the X-ray detection camera 10 using, for example, a known Tucker approximation or the like on the basis of information such as a tube voltage, a target angle, a target material, the material and thickness of the filters 51 and 19 and their presence or absence, the type of window material of the X-ray detection camera 10 and its presence or absence, and the material and thickness of the scintillators 11*a* and 11*b* of the X-ray detection camera 10 which are included in the condition information. The calculation unit 202 further calculates a spectral intensity integration value and a photon number integration value from the spectrum of the X-rays, and calculates the value of the average energy of the X-rays by dividing the spectral intensity integration value by the photon number integration value.

A calculation method using a known Tucker approximation will be described. For example, in a case where the target is specified as tungsten and the target angle is specified as 25°, the calculation unit 202 can determine Em: kinetic energy during electron target collision, T: electron kinetic energy in the target, A: proportionality constant determined by the atomic number of the target substance, ρ: the density of the target, μ(E): the linear attenuation coefficient of the target substance, B: the function of Z and T that changes gently, C: the Thomson-Whiddington constant, θ: the target angle, and c: the speed of light in vacuum. Further, the calculation unit 202 can calculate an irradiation X-ray spectrum by calculating the following Formula (1) on the basis of these values.

[Expression 1]

$$\varphi(E) = A \cdot \int_{E}^{Em} \left( \frac{T + m_0 c^2}{T} \right) \cdot B \cdot \left( \frac{1}{\rho} \frac{dT}{dx} \right)^{-1} \exp\left\{ -\mu(E) \frac{\left(E_m^2 - T^2\right)}{\rho C \sin(\theta + \varphi)} \right\} dT \tag{1}$$

Meanwhile, Em can be determined from information on the tube voltage, A, ρ, and (μE) can be determined from information on the material of the subject F, and θ can be determined from information on the angle of the subject F.

Next, the calculation unit 202 can calculate the X-ray energy spectrum that passes through the filter and the subject F and is absorbed by the scintillator by using the X-ray attenuation expression of the following Formula (2).

[Expression 2]

$$I = I_0 e^{-\mu x} \tag{2}$$

Here, μ is the attenuation coefficient of the subject F, the filter, the scintillator, or the like, and x is the thickness of the subject F, the filter, the scintillator, or the like. In addition, μ can be determined from information on the materials of the subject F, the filter, and the scintillator, and x can be determined from information on the thicknesses of the subject F, the filter, and the scintillator. The X-ray photon number spectrum can be obtained by dividing this X-ray energy spectrum by energy of each X-ray. The calculation unit 202 calculates the average energy of X-rays using the following Formula (3) by dividing the integration value of energy intensity by the integration value of the number of photons.

Average energy $E$=spectral intensity integration value/photon number integration value (3)

The calculation unit 202 calculates the average energy of X-rays through the above calculation process. Meanwhile, for the calculation of the X-ray spectrum, a known Kramers or Birch approximation or the like may be used.

The image acquisition unit 203 acquires a radiographic image obtained by irradiating the subject F with radiation and capturing an image of the radiation passing through the subject F. Specifically, the image acquisition unit 203 generates an X-ray image on the basis of the digital signal (amplified signal) output from the X-ray detection camera (more specifically, the output interfaces 17*a* and 17*b*). The image acquisition unit 203 generates one X-ray image by performing average processing or addition processing on two digital signals output from the output interfaces 17*a* and

Figure 4:
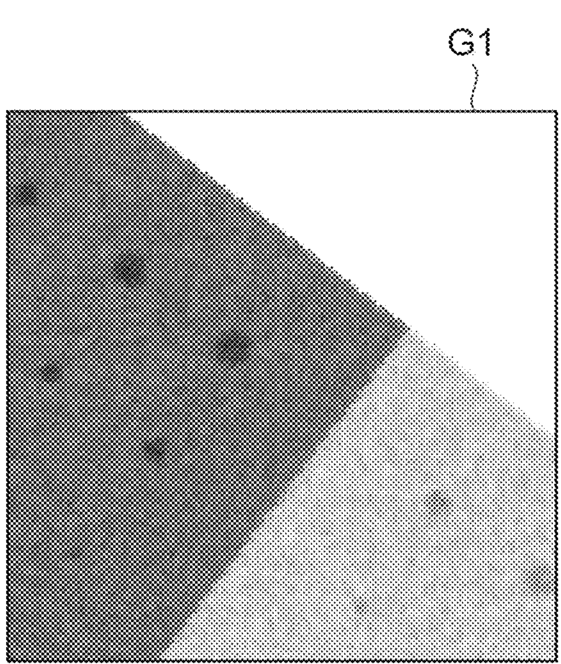
FIG. 4 is a diagram illustrating an example of an X-ray image acquired by an image acquisition unit 203 of FIG. 3.

17*b*. FIG. 4 is a diagram illustrating an example of an X-ray image acquired by the image acquisition unit 203.

The noise map generation unit 204 derives an evaluation value from the pixel value of each pixel in the radiographic image on the basis of relationship data indicating a relationship between the pixel value and the evaluation value obtained by evaluating the spread of the noise value, and generates a noise map that is data in which the derived evaluation value is associated with each pixel in the radiographic image. In this case, the noise map generation unit 204 derives an evaluation value from the average energy related to radiation passing through the subject F and the pixel value of each pixel in the radiographic image. Specifically, the noise map generation unit 204 uses the relational expression (relationship data) between the pixel value and the standard deviation of noise values (evaluation value obtained by evaluating the spread of the noise value) to derive the standard deviation of noise values from the average energy of X-rays calculated by the calculation unit 202 and the pixel value of each pixel in the X-ray image (radiographic image) acquired by the image acquisition unit 203. The noise map generation unit 204 generates a noise standard deviation map (noise map) by associating the derived standard deviation of noise values with each pixel in the X-ray image.

The relational expression between the pixel value and average energy used by the noise map generation unit 204 and the standard deviation of noise values is represented by the following Formula (4).

[Expression 3]

$$\text{Noise} = \sqrt{\left( FMCQ \sqrt{\frac{cf}{E_m M_E CQ} \cdot \text{Signal}} \right)^2 + \left(\sqrt{D}\right)^2 + (R)^2} \tag{4}$$

In Formula (4), the variable Noise is the standard deviation of noise values, the variable Signal is the signal value of a pixel (pixel value), the constant F is a noise factor, the constant M is a scintillator multiplication factor, the constant C is coupling efficiency between the line scan camera 12*a* and the scintillator 11*a* or the line scan camera 12*b* and the scintillator 11*b* in the X-ray detection camera 10, the constant Q is the quantum efficiency of the line scan camera 12*a* or the line scan camera 12*b*, the constant cf is a conversion coefficient for converting the signal value of a pixel into an electric charge in the line scan camera 12*a* or the line scan camera 12*b*, the variable Em is the average energy of X-rays, the constant D is dark current noise generated by thermal noise in the image sensor, and the constant R is readout noise in the line scan camera 12*a* or the line scan camera 12*b*. when Formula (4) is used, the noise map generation unit 204 substitutes the pixel value of each pixel in the X-ray image acquired by the image acquisition unit 203 into the variable Signal, and substitutes the numerical value of average energy calculated by the calculation unit 202 into the variable Em. The noise map generation unit 204 obtains the variable Noise calculated using Formula (4) as the numerical value of the standard deviation of noise values. Meanwhile, other parameters including the average energy may be acquired by the input unit 201 accepting an input, or may be set in advance.

Figure 5:
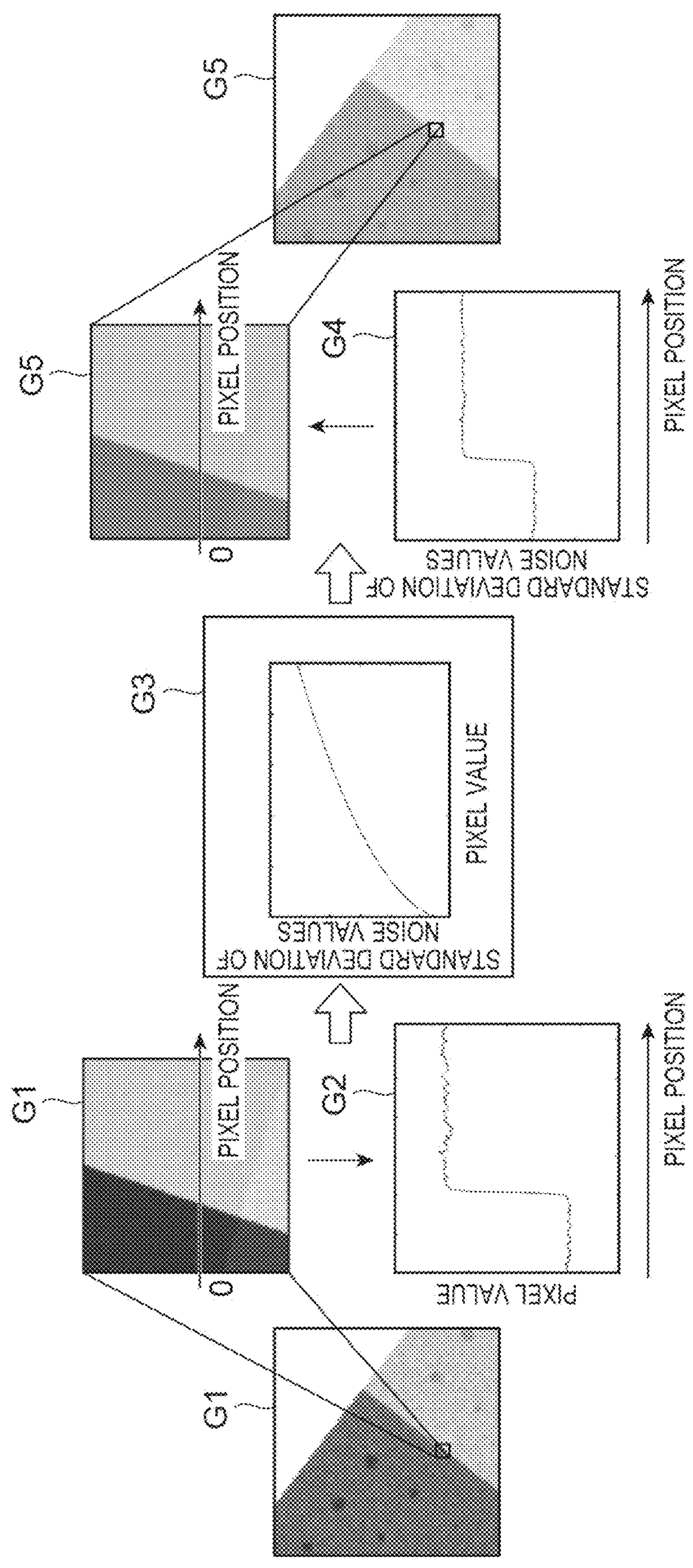
FIG. 5 is a diagram illustrating an example of generation of a noise standard deviation map which is performed by a noise map generation unit 204 of FIG. 3.

FIG. 5 is a diagram illustrating an example of generation of a noise standard deviation map which is performed by the noise map generation unit 204. The noise map generation unit 204 substitutes various pixel values into the variable Signal and acquires a correspondence relation between the pixel value and the variable Noise using the relational expression (4) between the pixel value and the standard deviation of noise values to thereby derive a relational graph G3 indicating the correspondence relation between the pixel value and the standard deviation of noise values. The noise map generation unit 204 derives relationship data G2 indicating the correspondence relation between each pixel position and the pixel value from an X-ray image G1 acquired by the image acquisition unit 203. Further, the noise map generation unit 204 derives the standard deviation of noise values corresponding to a pixel at each pixel position in the X-ray image by applying the correspondence relation indicating the relational graph G3 to each pixel value in the relationship data G2. As a result, the noise map generation unit 204 associates the derived standard deviation of noise with each pixel position and derives relationship data G4 indicating the correspondence relation between each pixel position and the standard deviation of noise. The noise map generation unit 204 generates a noise standard deviation map G5 on the basis of the derived relationship data G4.

Figure 6:
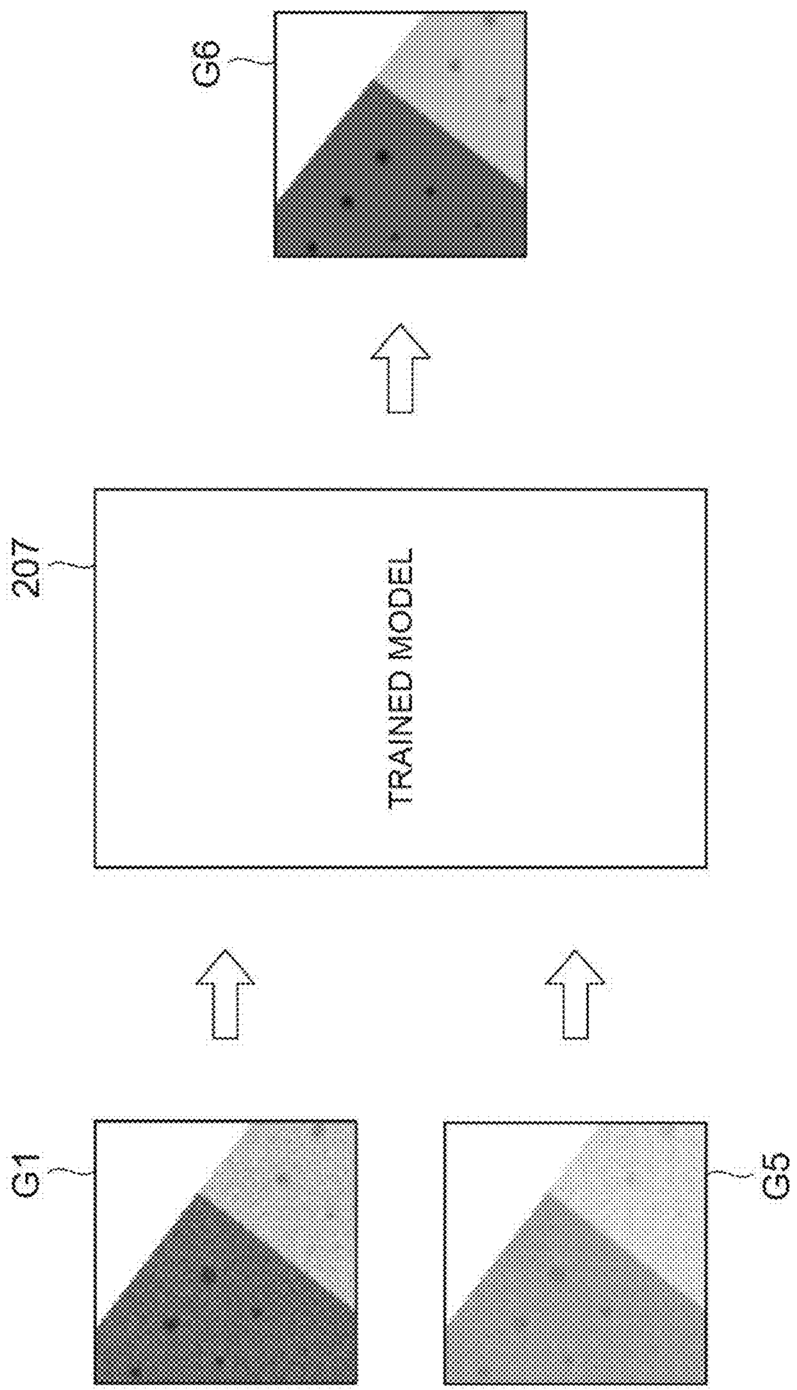
FIG. 6 is a diagram illustrating an example of input and output data of a trained model 207 of FIG. 3.

The processing unit 205 inputs the radiographic image and the noise map to the trained model 207 constructed in advance through machine learning and executes image processing of removing noise from the radiographic image. That is, as shown in FIG. 6, the processing unit 205 acquires the trained model 207 (which will be described later) constructed by the construction unit 206 from a built-in memory or a storage medium in the control device 20. The processing unit 205 inputs the X-ray image G1 acquired by the image acquisition unit 203 and the noise standard deviation map G5 generated by the noise map generation unit 204 to the trained model 207. Thereby, the processing unit 205 generates an output image G6 by executing image processing of removing noise from the X-ray image G1 using the trained model 207. The processing unit 205 then outputs the generated output image G6 to the display device 30 or the like.

The construction unit 206 uses a training image which is a radiographic image, a noise map generated from the training image on the basis of the relational expression between the pixel value and the standard deviation of noise values, and noise-removed image data which is data obtained by removing noise from the training image, as training data, to construct the trained model 207 that outputs noise-removed image data on the basis of the training image and the noise map through machine learning. The construction unit 206 stores the constructed trained model 207 in a built-in memory or a storage medium within the control device 20. Examples of machine learning include supervised learning, unsupervised learning, and reinforcement learning, including deep learning, neural network learning, and the like. In the first embodiment, the two-dimensional convolutional neural network described in the paper "Beyond a Gaussian Denoiser: Residual Learning of Deep CNN for Image Denoising" authored by Kai Zhang et al. is adopted as an example of a deep learning algorithm. Meanwhile, the trained model 207 may be generated by an external computer or the like and download to the control device 20 in addition to being constructed by the construction unit 206. Meanwhile, the radiographic image used for machine learning includes a radiographic image obtained by capturing an image of a known structure or an image obtained by reproducing the radiographic image.

Figure 7:
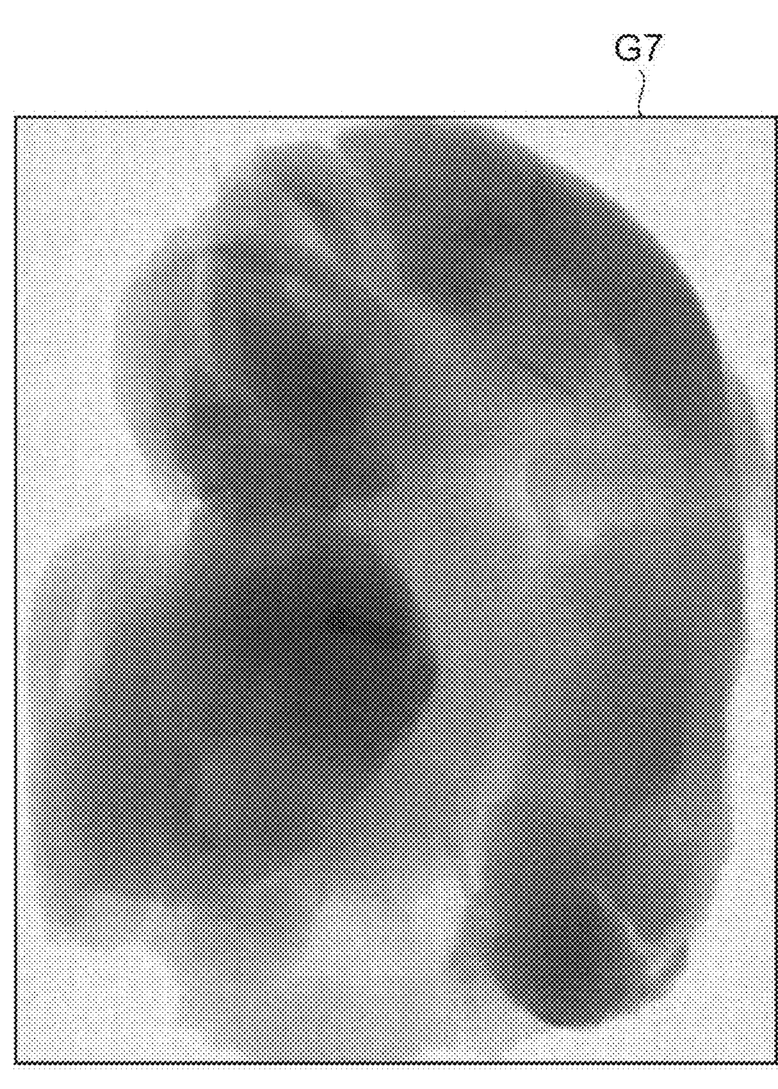
FIG. 7 is a diagram illustrating an example of a training image which is one piece of training data used to construct the trained model 207.

FIG. 7 is an example of a training image which is one piece of training data used to construct the trained model 207. X-ray images of patterns having various thicknesses, various materials, and various resolutions can be used as training images. The example shown in FIG. 7 is a training image G7 generated for chicken. The training image G7 may be an X-ray image actually generated for a plurality of types of known structures using the image acquisition device 1, or may be an image generated by simulation calculation. The X-ray image may be acquired using a device different from the image acquisition device 1.

As preprocessing for performing machine learning, the construction unit 206 derives an evaluation value from the pixel value of each pixel in the radiographic image on the basis of the relationship data indicating the relationship between the pixel value and the evaluation value obtained by evaluating the spread of the noise value, and generates a noise map that is data in which the derived evaluation value is associated with each pixel in the radiographic image. Specifically, when the trained model 207 is constructed, the construction unit 206 acquires a training image generated by actual image capturing, simulation calculation, or the like from the image acquisition unit 203 or the like. The construction unit 206 then sets, for example, the operating conditions of the X-ray irradiator 50 of the image acquisition device 1, the imaging conditions of the image acquisition device 1, or the like. Alternatively, the construction unit 206 sets the operating conditions or imaging conditions of the X-ray irradiator 50 during simulation calculation. The construction unit 206 uses the same method as the calculation unit 202 to calculate the average energy of X-rays on the basis of the above operating conditions or imaging conditions. Further, the construction unit 206 uses the same method as the method used by the noise map generation unit 204 as shown in FIG. 5 to generate a noise standard deviation map on the basis of the average energy of X-rays and the training image. That is, the preprocessing method of the machine-learning method includes a noise map generation step of deriving an evaluation value from the pixel value of each pixel in the radiographic image on the basis of the relationship data indicating the relationship between the pixel value and the evaluation value obtained by evaluating the spread of the noise value, and generating a noise map that is data in which the derived evaluation value is associated with each pixel in the radiographic image.

The construction unit 206 constructs the trained model 207 through machine learning using a training image, a noise map generated from the training image, and noise-removed image data which is data from which noise is removed in advance from the training image, as training data. Specifically, the construction unit 206 acquires noise-removed image data in which noise is removed from the training image in advance. In a case where the training image is an X-ray image generated by simulation calculation, the construction unit 206 uses the image before noise is added in a process of generating the training image as the noise-removed image data. On the other hand, in a case where the training image is an X-ray image actually generated for a plurality of types of known structures using the image acquisition device 1, the construction unit 206 uses the noise-removed image as the noise-removed image data from the X-ray image using image processing such as an average filter, median filter, bilateral filter, or NLM filter. The construction unit 206 constructs the trained model 207 that outputs noise-removed image data on the basis of the training image and the noise standard deviation map by executing training based on machine learning.

Figure 8:
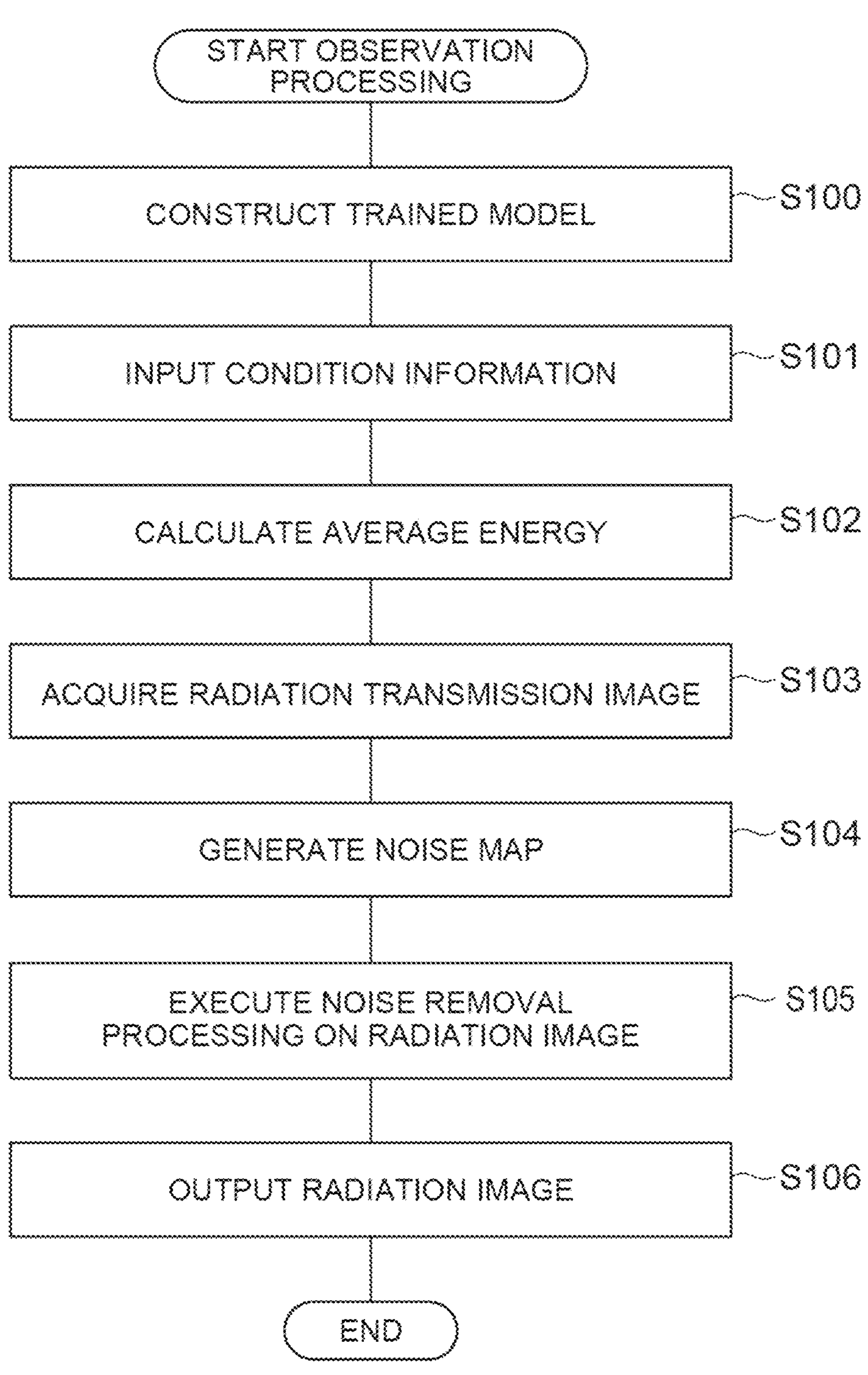
FIG. 8 is a flowchart illustrating a procedure of observation processing performed by the image acquisition device 1.

Next, a procedure of observing an X-ray transmission image of the subject F using the image acquisition device 1 according to the first embodiment, that is, a flow of the radiographic image processing method according to the first embodiment will be described. FIG. 8 is a flowchart illustrating a procedure of observation processing performed by the image acquisition device 1.

First, the construction unit 206 uses a training image, a noise standard deviation map generated from the training image on the basis of the relational expression, and noise-removed image data, as training data to construct the trained model 207 that outputs noise-removed image data on the basis of the training image and the noise standard deviation map through machine learning (step S100). Next, the input unit 201 accepts an input of condition information indicating the operating conditions of the X-ray irradiator 50, the imaging conditions of the X-ray detection camera 10, or the like from an operator (user) of the image acquisition device 1 (step S101). The calculation unit 202 calculates the value of average energy of X-rays detected by the X-ray detection camera 10 on the basis of the condition information (step S102).

Next, the subject F is set in the image acquisition device 1, an image of the subject F is captured, and an X-ray image of the subject F is acquired by the control device 20 (step S103). Further, the control device 20 derives the standard deviation of noise values from the average energy of X-rays and the pixel value of each pixel in the X-ray image on the basis of the relational expression between the pixel value and the standard deviation of noise values, and generates a noise standard deviation map by associating the derived standard deviation of noise with each pixel value (step S104).

Next, the processing unit 205 inputs the X-ray image of the subject F and the noise standard deviation map to the trained model 207 constructed and stored in advance, and executes noise removal processing on the X-ray image (step S105). Further, the processing unit 205 outputs an output image which is an X-ray image that has undergone noise removal processing to the display device 30 (step S106).

According to the image acquisition device 1 described above, the standard deviation of noise values is derived from the pixel value of each image of the X-ray image using the relational expression between the pixel value and the standard deviation of noise values, and a noise standard deviation map that is data in which the derived standard deviation of noise values is associated with each pixel in the X-ray image is generated. The X-ray image and the noise standard deviation map are then input to the trained model 207 constructed in advance through machine learning, and image processing of removing noise from the X-ray image is executed. With such a configuration, noise in each pixel in the X-ray image is removed through machine learning in consideration of the standard deviation of noise values derived from the pixel value of each pixel in the X-ray image. This makes it possible to realize noise removal corresponding to the relationship between the pixel value and the standard deviation of noise values in the X-ray image using the trained model 207. As a result, it is possible to effectively remove noise in the X-ray image.

Particularly, in the X-ray image, the mode of noise changes depending on differences in a tube voltage, a filter, a scintillator, conditions of an X-ray detection camera (a gain setting value, a circuit noise value, an amount of saturated charge, a conversion coefficient value (e-/count), and the line rate of the camera), a subject, and the like. For this reason, in a case where noise removal is attempted to be realized through machine learning, preparation of a trained model trained under various conditions can be considered. That is, as a comparative example, a method of constructing a plurality of trained models in accordance with the conditions during the measurement of the X-ray image, selecting a trained model for each condition, and executing noise removal processing can also be adopted. In the case of such a comparative example, a trained model must be constructed for each noise condition such as, for example, the average energy of X-rays, the gain of the X-ray detection camera, and the type of X-ray camera, and a huge number of trained models are required to be generated, which may take a long time to perform construction. As an example, when there are ten average energies of X-rays, eight gains of the X-ray detection camera, and three types of products, 240 trained models are required, but in a case where it takes one day per model to construct a trained model, it will take 240 days for machine learning. In this regard, according to the present embodiment, by generating a noise map from the X-ray image and using the noise map as input data for machine learning, it is possible to reduce the noise conditions that require the generation of a trained model, and the learning time to construct the trained model 207 is greatly reduced.

Figure 9:
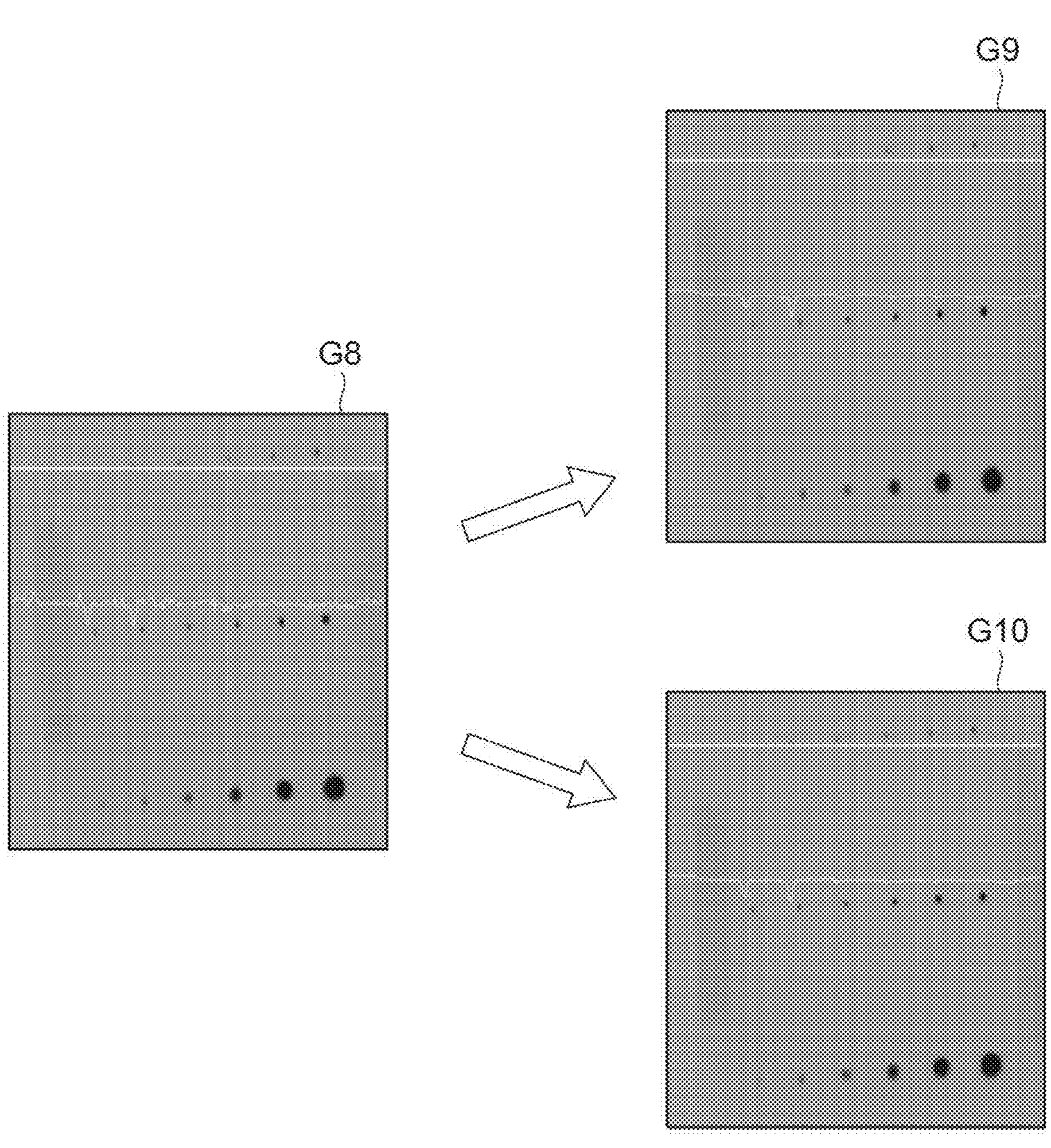
FIG. 9 is a diagram illustrating an example of X-ray images before and after noise removal processing, acquired by the image acquisition device 1.
Figure 10:
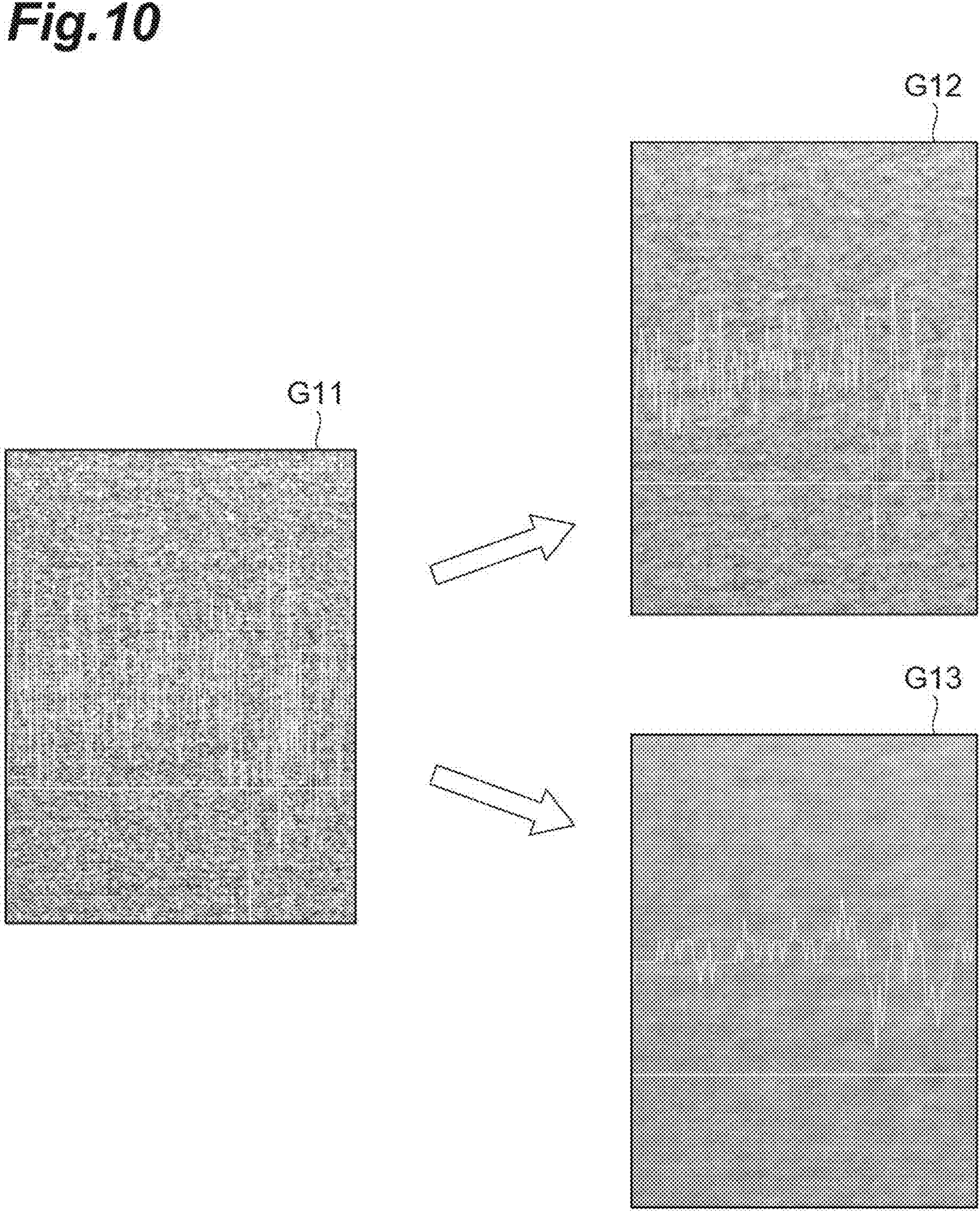
FIG. 10 is a diagram illustrating an example of X-ray images before and after noise removal processing, acquired by the image acquisition device 1.

FIGS. 9 and 10 show examples of X-ray images before and after noise removal processing acquired by the image acquisition device 1. FIG. 9 shows X-ray images acquired under the conditions in which the operating conditions of the X-ray irradiator 50 and the imaging conditions of the X-ray detection camera 10 are the same as training data used to construct the trained model 207. In the drawing, an X-ray image G8 is a measured image, an X-ray image G9 is an image that has undergone noise removal processing with a trained model trained under the same conditions as the imaging conditions in the comparative example, and an X-ray image G10 is an image that has undergone noise removal processing using a noise standard deviation map generated by the control device 20 in the first embodiment. The standard deviations of noise values in the X-ray images G8, G9 and G10 are 14.3, 3.4, and 3.7, respectively.

FIG. 10 shows X-ray images acquired in a case where the operating conditions of the X-ray irradiator 50 or the imaging conditions of the X-ray detection camera 10 are conditions different from the training data used to construct the trained model 207. In the drawing, an X-ray image G11 is a measured image, an X-ray image G12 is an image that has undergone noise removal processing with a trained model trained under conditions different from the imaging conditions in the comparative example, and an X-ray image G13 is an X-ray image that has undergone noise removal processing using the noise standard deviation map generated by the control device 20 in the first embodiment. The standard deviations of noise values in the X-ray image G11, G12 and G13 are 3.5, 2.0, and 0.9, respectively.

In the comparative example, as shown in FIG. 9, in a case where the operating conditions of the X-ray irradiator 50 or the imaging conditions of the X-ray detection camera 10 are the same conditions as the training data used to construct the trained model 207, the standard deviation of noise values in the X-ray image G9 is sufficiently reduced compared with the X-ray image G8 before noise removal processing. The trained model in the comparative example can output an X-ray image from which noise is sufficiently removed. However, as shown in FIG. 10, in a case where the operating conditions of the X-ray irradiator 50 or the imaging conditions of the X-ray detection camera 10 are conditions different from the training data used to construct the trained model 207, the standard deviation of noise values in the X-ray image G12 after noise processing is not sufficiently reduced compared with the X-ray image G11 before noise removal processing. Therefore, the trained model in the comparative example cannot output an X-ray image from which noise is sufficiently removed in a case where conditions differ between training and image capturing.

On the other hand, according to the first embodiment, the trained model 207 is constructed in consideration of changes in the operating conditions of the X-ray irradiator 50 or the imaging conditions of the X-ray detection camera 10 during the measurement of the X-ray image. Thereby, as shown in FIGS. 9 and 10, in the X-ray image G10 and 13, the standard deviation of noise values is sufficiently reduced compared with the X-ray images G8 and 11 before noise removal processing. Therefore, according to the first embodiment, sufficient noise removal corresponding to changes in the operating conditions of the X-ray irradiator 50 or the imaging conditions of the X-ray detection camera 10 is realized. This makes it possible to effectively remove noise in the X-ray image using a single trained model 207.

In general, X-ray images contain noise derived from X-ray generation. Increasing the X-ray dose in order to improve the SN ratio of the X-ray image can also be considered. However, in that case, increasing the X-ray dose leads to an increase in the amount of exposure to the sensor, a reduction in the life of the sensor, and a reduction in the life of the X-ray source, which makes it difficult to achieve both an improvement in SN ratio and a long life. In addition, since the amount of heat generated also increases with an increase in X-ray dose, it may be necessary to take measures to dissipate the increased heat. In the first embodiment, since there is no need to increase the X-ray dose, it is possible to achieve both an improvement in SN ratio and a long life, and to omit measures for heat dissipation.

In addition, the control device 20 of the first embodiment has a function of deriving the standard deviation of noise values from the average energy related to X-rays passing through the subject F and the pixel value of each pixel in the X-ray image. Here, in the comparative example, for example, when the average energy changes, the relationship between the pixel value and noise in the X-ray image fluctuates, and thus the noise cannot be sufficiently removed even with the trained model. On the other hand, in the present embodiment, since the standard deviation of noise values in the pixel value of each pixel in the X-ray image is derived considering the average energy related to X-rays passing through the subject F, it is possible to realize noise removal corresponding to the relationship between the pixel value in the X-ray image and the standard deviation of noise values. As a result, it is possible to more effectively remove noise in the X-ray image. In addition, in the comparative example, it was necessary to construct a different trained model for each average energy. On the other hand, according to the first embodiment, since the difference in average energy is reflected in the noise standard deviation map and the noise standard deviation map is input to the trained model, the number of trained models that need to be constructed is one. Thereby, the learning time to construct the trained model 207 is greatly reduced.

In addition, the control device 20 of the first embodiment has a function of accepting an input of condition information indicating either the operating conditions of the X-ray irradiator 50 or the imaging conditions of the X-ray detection camera 10 and calculating the average energy on the basis of the condition information. Further, the condition information includes at least any one of the tube voltage of the X-ray irradiator 50, information relating to the subject F, information on a filter included in the X-ray irradiator 50, information on a filter included in the X-ray detection camera 10, and information on a scintillator included in the X-ray detection camera 10. With such a configuration, since the average energy of X-rays passing through the subject F is calculated with a good degree of accuracy, it is possible to realize noise removal corresponding to the relationship between the pixel value and the standard deviation of noise values. As a result, it is possible to more effectively remove noise in the X-ray image.

In addition, in the control device 20 of the first embodiment, the spread of the noise value is evaluated as the standard deviation of noise values. Thereby, since the spread of the noise value in the pixel value of each pixel in the X-ray image is evaluated more precisely, it is possible to realize noise removal corresponding to the relationship between the pixel value and noise. As a result, it is possible to more effectively remove noise in the X-ray image.

In addition, the control device 20 of the first embodiment has a function of using a training image which is an X-ray image, a noise standard deviation map generated from the training image on the basis of the relational expression between the pixel value and the standard deviation of noise values, and noise-removed image data which is data obtained by removing noise from the training image, as training data, to construct the trained model 207 that outputs noise-removed image data on the basis of the training image and the noise standard deviation map through machine learning. With such a configuration, the trained model 207 used for noise removal in the X-ray image is constructed through machine learning using the training data. Thereby, when a training image and a noise standard deviation map generated from the training image are input to the trained model 207, it is possible to realize noise removal corresponding to the relationship between the pixel value and the standard deviation of noise values. As a result, it is possible to more effectively remove noise in the X-ray image.

In addition, in the control device 20 of the first embodiment, in order to generate a noise standard deviation map which is training data for machine learning, the standard deviation of noise values is derived from the pixel value of each pixel in the training image on the basis of the relational expression between the pixel value and the standard deviation of noise values, and a noise standard deviation map that is data in which the derived standard deviation of noise is associated with each pixel in training image is generated. With such a configuration, the noise standard deviation map which is training data for machine learning corresponds to the relational expression between the pixel value and the standard deviation of noise values. Thereby, when an X-ray image and a noise standard deviation map generated from the X-ray image are input to the trained model 207, it is possible to realize noise removal corresponding to the relational expression between the pixel value and the standard deviation of noise values. As a result, it is possible to more effectively remove noise in the X-ray image.

Modification Example of Control Device 20 of First Embodiment

Figure 11:
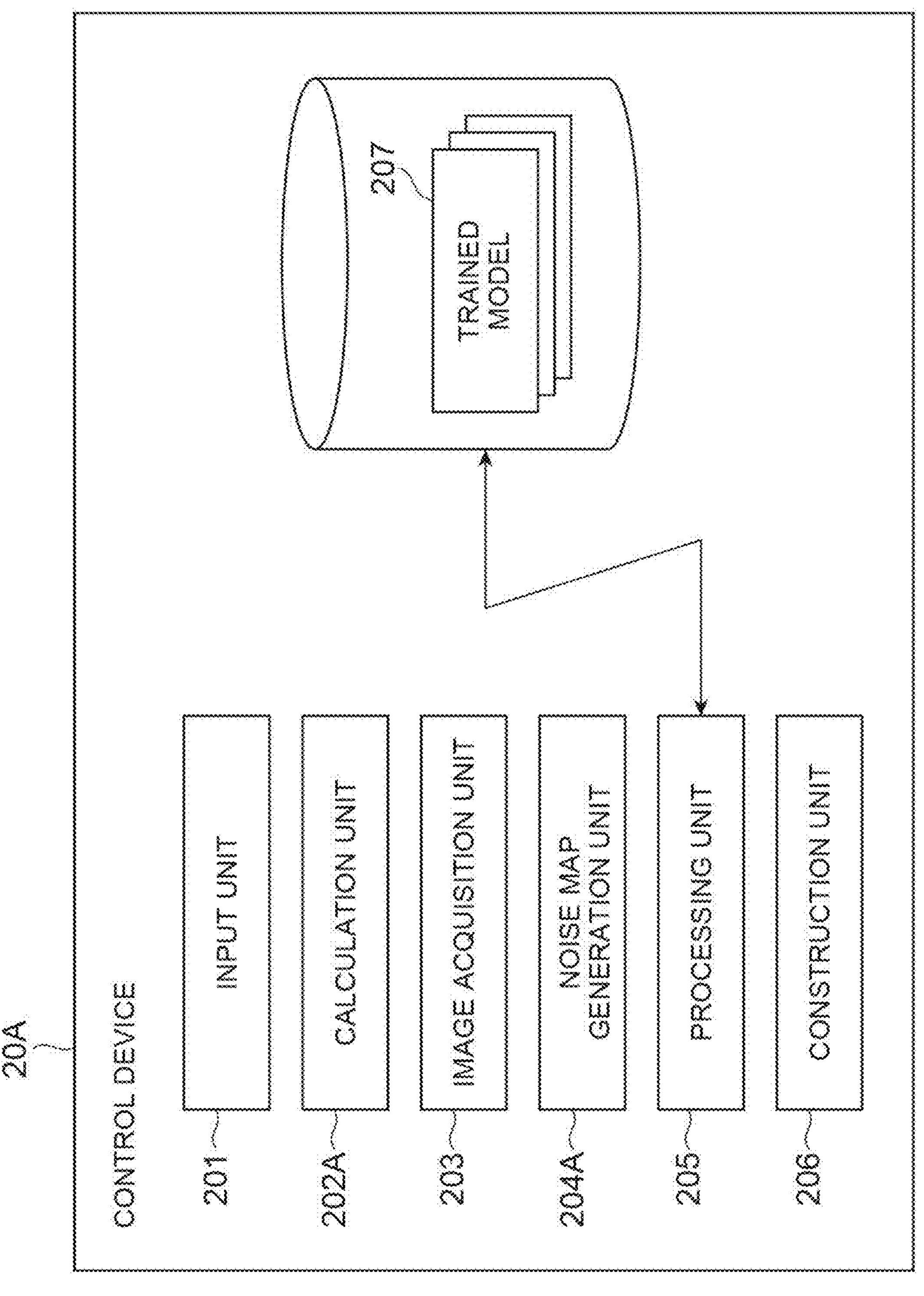
FIG. 11 is a block diagram illustrating a functional configuration of a control device 20A according to a modification example of the present disclosure.
Figure 12:
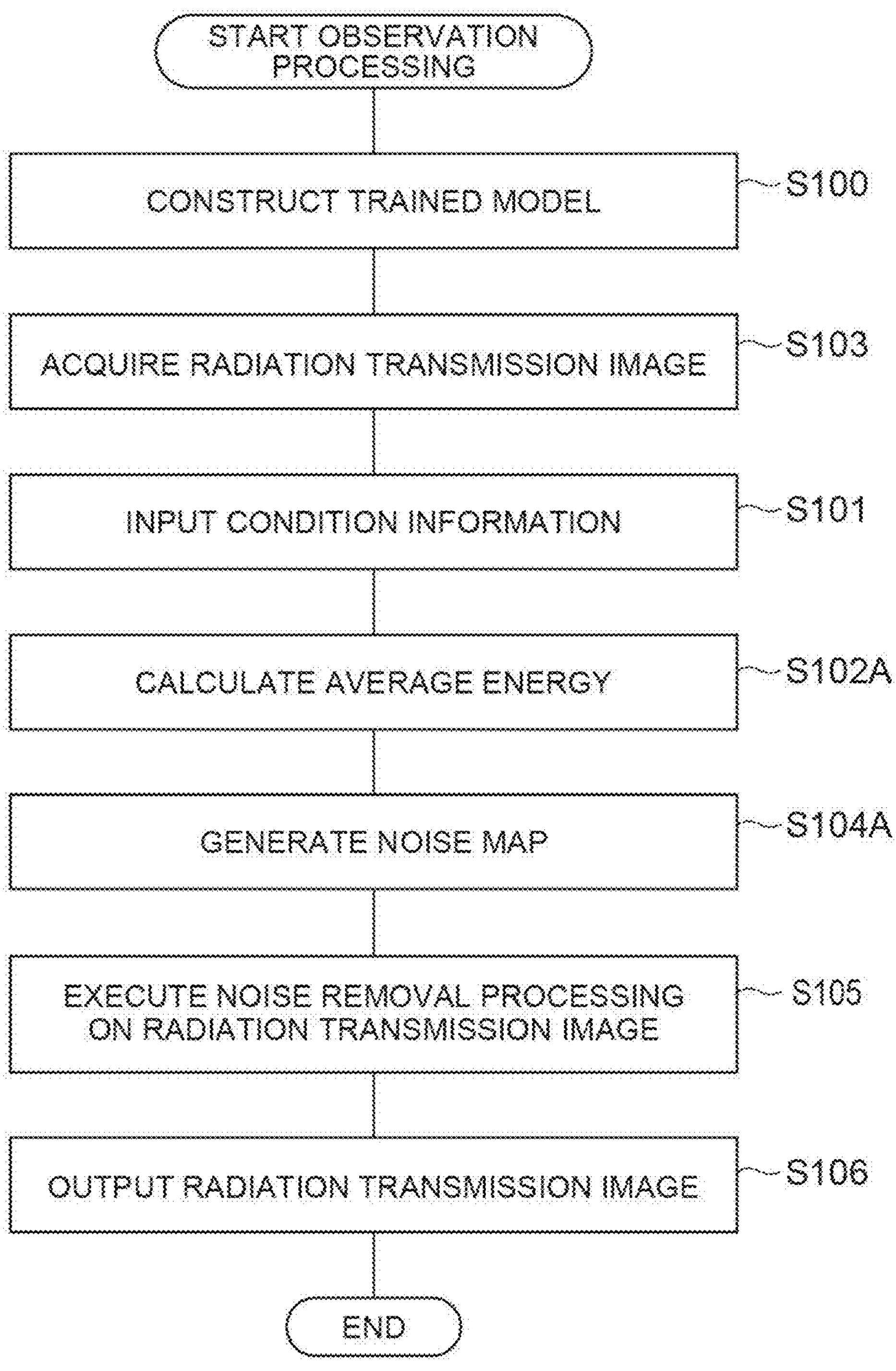
FIG. 12 is a flowchart illustrating a procedure of observation processing performed by the image acquisition device 1 according to the modification example of the present disclosure.

FIG. 11 is a block diagram illustrating a functional configuration of a control device 20A in a modification example of the first embodiment. The control device 20A is different from the above-described first embodiment in that a calculation unit 202A has a function of deriving the average energy of X-rays from the pixel value of the X-ray image, and that a noise map generation unit 204A has a function of deriving a noise standard deviation map on the basis of the pixel value of the X-ray image and the average energy of X-rays derived from the X-ray image. FIG. 12 is a flowchart illustrating a procedure of observation processing performed by the image acquisition device 1 including the control device 20A of FIG. 11. As shown in FIG. 12, in the control device 20A, the process shown in step S103 of the control device 20 according to the first embodiment shown in FIG. 8 is performed immediately after step S100. In the control device 20A, the processes shown in S102A and S104A are executed in place of the processes of steps S102 and S104 of the control device 20.

The calculation unit 202A calculates the average energy from the pixel value of each pixel in the radiographic image (step S102A). Specifically, the calculation unit 202A derives in advance the relationship between the pixel value and the average energy for each piece of condition information through simulation calculation of the X-ray spectrum or the like. The calculation unit 202A acquires condition information including at least the tube voltage acquired by the input unit 201 and information on a scintillator included in the X-ray detection camera 10. The calculation unit 202A then selects a relationship corresponding to the condition information from the previously derived relationship between the pixel value and the average energy on the basis of the condition information. Further, the calculation unit 202A derives the average energy for each pixel from the pixel value of each pixel in the X-ray image acquired by the image acquisition unit 203 on the basis of the selected relationship.

Hereinafter, the derivation of the relationship between the pixel value and the average energy for each piece of condition information which is performed by the calculation unit 202A will be described with reference to FIGS. 13 to 17.

Figure 13:
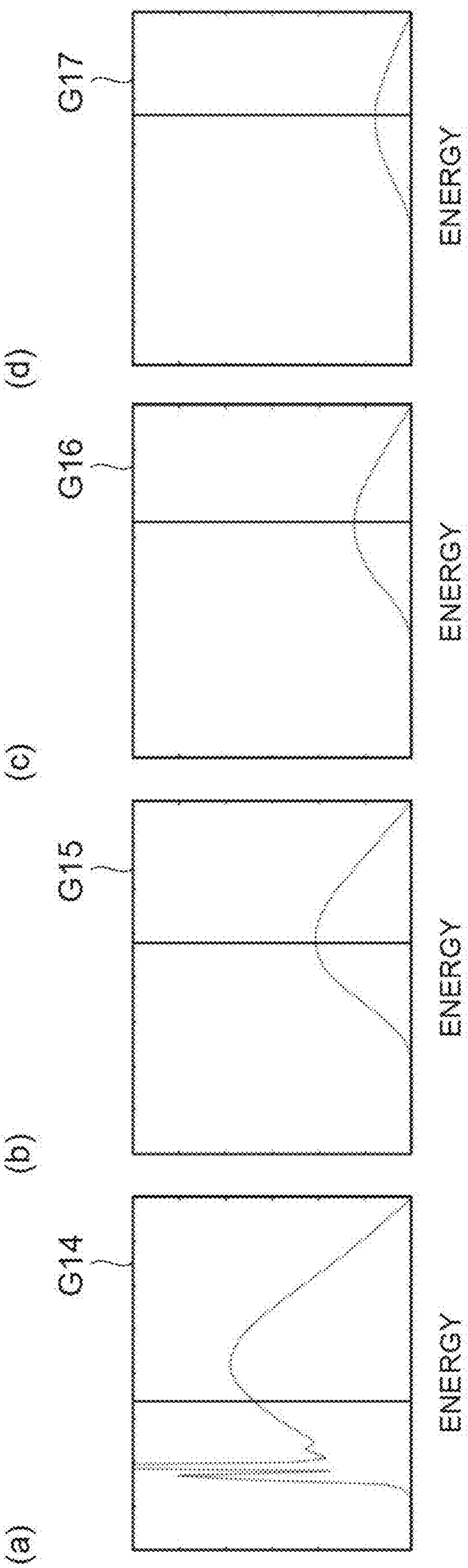
FIG. 13 is a graph illustrating an example of simulation calculation results of the energy spectrum of transmitted X-rays obtained by a calculation unit 202A of FIG. 11.

First, the calculation unit 202A derives a graph G18 indicating a relationship between the thickness of the subject F and the transmittance of X-rays and a graph G19 indicating a relationship between the thickness of the subject F and the average energy of X-rays on the basis of the condition information. Specifically, as shown in the parts (a) to (d) of FIG. 13, the calculation unit 202A calculates energy spectra G14 to G17 of X-rays transmitted in a case where the thickness of the subject F is changed in various ways on the basis of the condition information including at least information on the tube voltage and the scintillator included in the X-ray detection camera 10 through simulation calculation. FIG. 13 is a graph illustrating an example of simulation calculation results of energy spectra of X-rays passing through the subject F in the calculation unit 202A. Here, the energy spectra G14 to G17 of transmitted X-rays are exemplified in a case where simulation calculation is performed by gradually increasing the thickness of the subject F composed of water. Further, the calculation unit 202A calculates the average energy of X-rays transmitted in a case where the thickness of the subject F is changed in various ways on the basis of the calculated energy spectra G14 to G17. Meanwhile, in addition to the simulation calculation, the calculation unit 202A may obtain the relationship between the thickness of the subject F and the average energy on the basis of the X-ray image obtained by capturing an image of a structure of which the thickness is known.

Further, the calculation unit 202A also derives a relationship between the thickness of the subject F and the transmittance of X-rays on the basis of the above simulation results. FIG. 14 is a table illustrating an example of a relationship between the thickness of the subject F and the average energy and transmittance derived by the calculation unit 202A. As shown in FIG. 14, the average energy of transmitted X-rays and the transmittance of X-rays are derived corresponding to each of the energy spectra G14 to G17 calculated for each thickness of the subject F.

Figure 15:
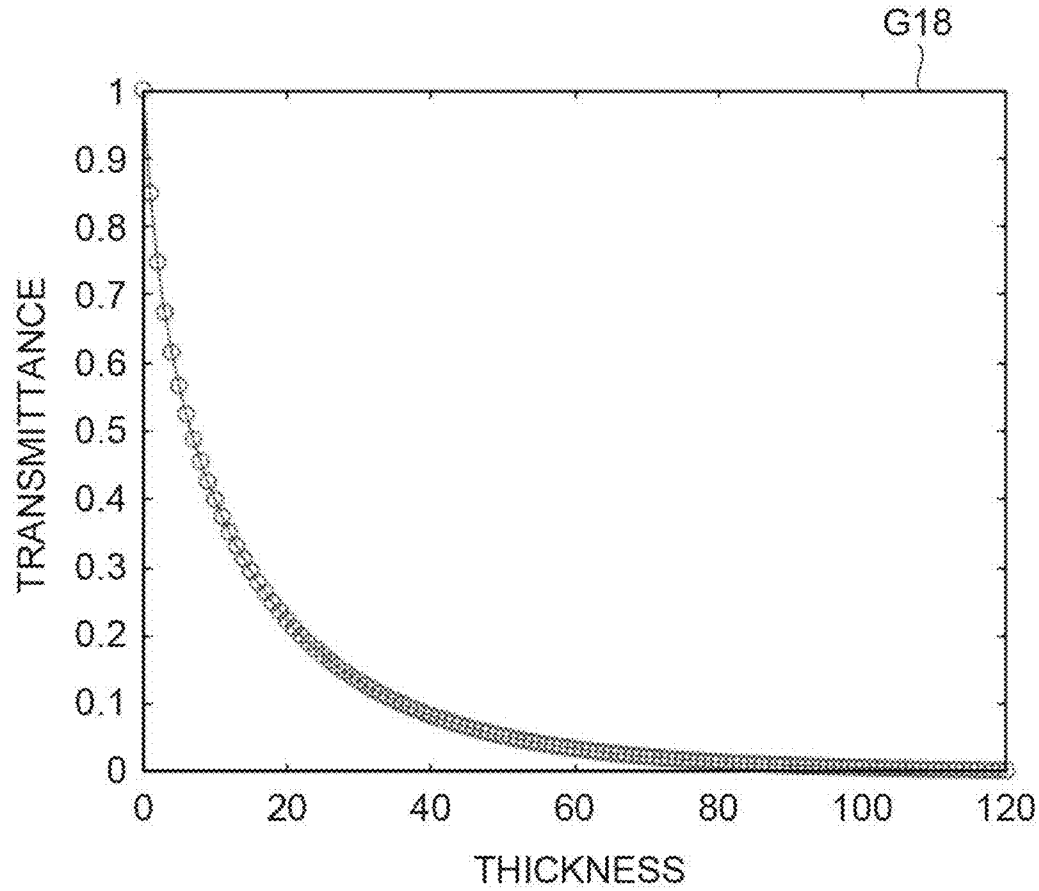
FIG. 15 is a graph illustrating an example of simulation calculation results of a relationship between the thickness of a subject and the transmittance of X-rays obtained by the calculation unit 202A of FIG. 11.
Figure 16:
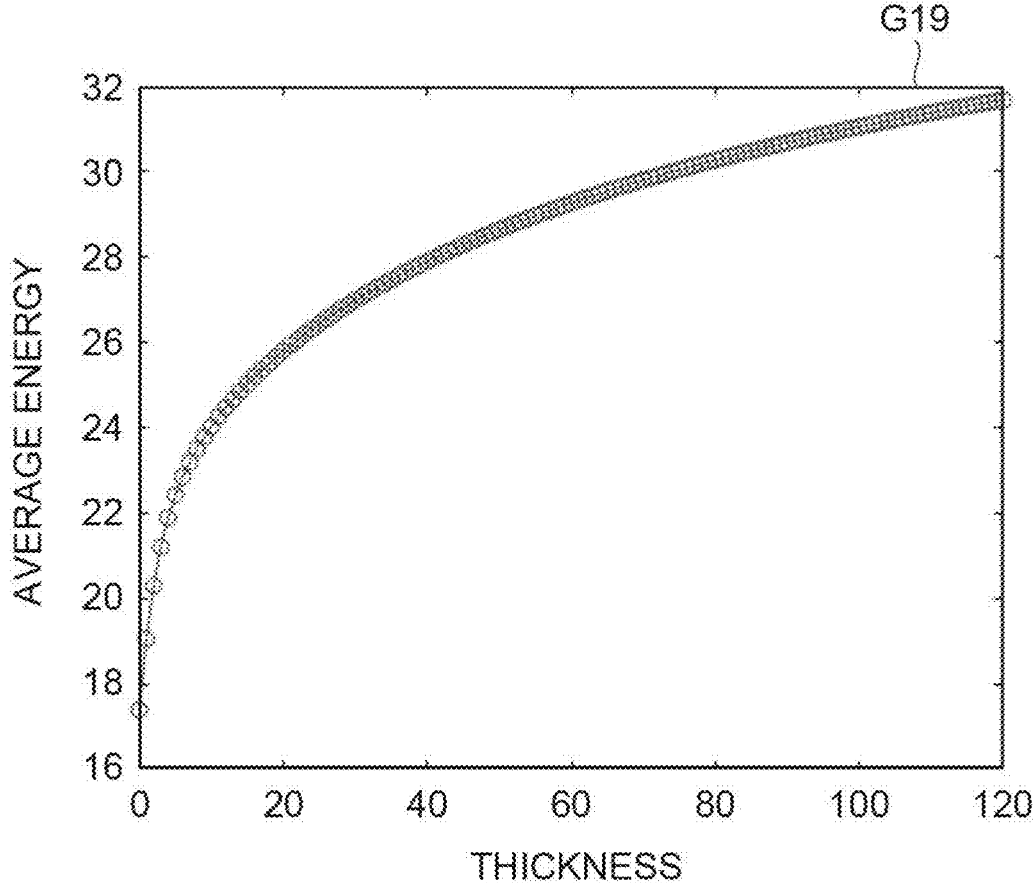
FIG. 16 is a graph illustrating an example of simulation calculation results of a relationship between the thickness of a subject and average energy of transmitted X-rays obtained by the calculation unit 202A of FIG. 11.

Subsequently, the calculation unit 202A derives the graph G18 indicating the relationship between the thickness of the subject F and the transmittance of X-rays from the transmittance of X-rays derived for the subject F having various thicknesses. FIG. 15 is a graph illustrating a relationship between the thickness of the subject F and the transmittance of X-rays with respect to the subject F derived by the calculation unit 202A. Additionally, the calculation unit 202A derives the graph G19 indicating a relationship between the thickness of the subject F and the average energy of X-rays from the average energy of X-rays derived for the subject F having various thicknesses. FIG. 16 is a graph illustrating a relationship between the thickness of the subject F and the average energy of X-rays passing through the subject F derived by the calculation unit 202A.

Figure 17:
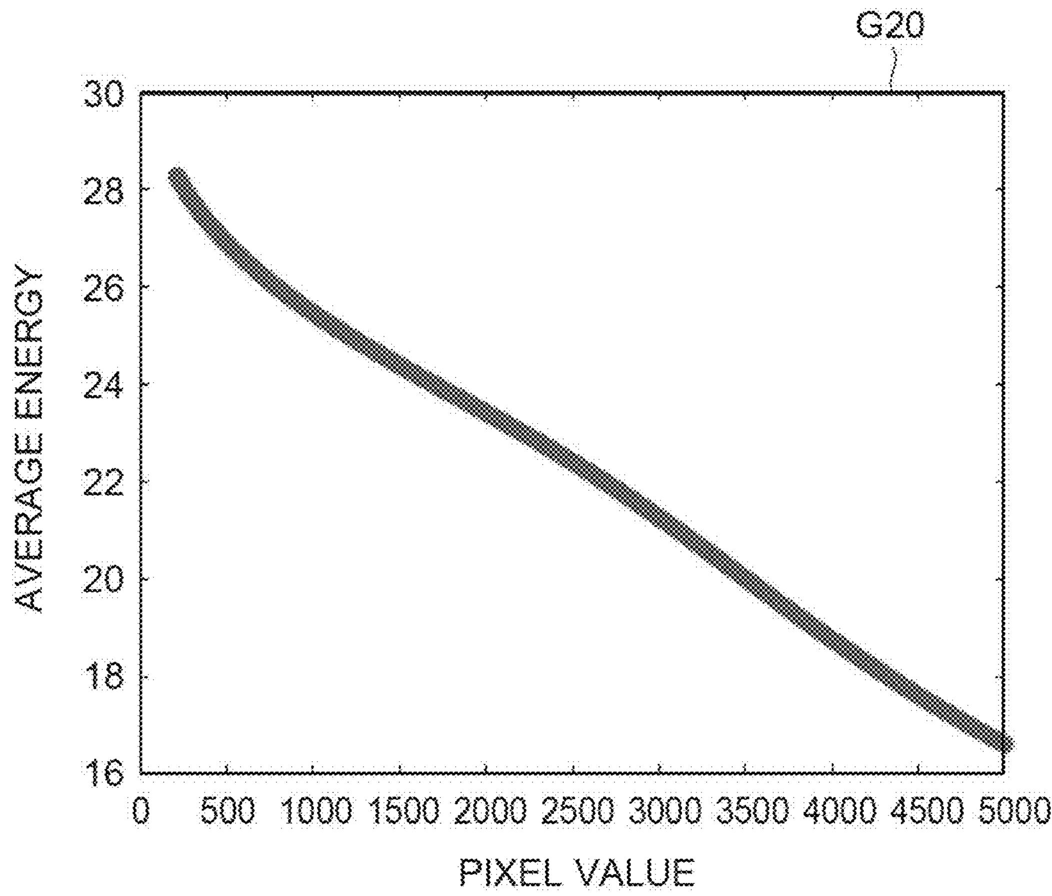
FIG. 17 is a graph illustrating an example of simulation calculation results of a relationship between the pixel value of an X-ray image and average energy obtained by the calculation unit 202A of FIG. 11.

The calculation unit 202A then derives a graph G20 indicating a relationship between the pixel value of the X-ray image and the average energy as shown in FIG. 17 for each of various types of condition information on the basis of the two graphs G18 and G19 derived for each of various types of condition information. FIG. 17 is a graph illustrating a relationship between the pixel value of the X-ray image and the average energy derived by the calculation unit 202A. Specifically, the calculation unit 202A derives the pixel value $I_0$ of the X-ray transmission image in a case where there is no subject F on the basis of the condition information. The calculation unit 202A then sets the pixel value I of the X-ray image in a case where there is the subject F, and calculates $I/I_0$ which is the transmittance of X-rays. Further, the calculation unit 202A derives the thickness of the subject F from $I/I_0$ which is the calculated transmittance of X-rays on the basis of the graph G18 of the thickness of the subject F and the transmittance of X-rays with respect to the subject F. Finally, the calculation unit 202A derives the average energy of transmitted X-rays corresponding to the thickness of the subject on the basis of the derived thickness of the subject F and the graph G19 of the thickness of the subject F and the average energy of transmitted X-rays. Subsequently, by performing the above derivation for each of various types of condition information while the pixel value I of the X-ray image is changed in various ways, the calculation unit 202A derives the graph G20 indicating the relationship between the pixel value of the X-ray image and the average energy of transmitted X-rays for each piece of condition information.

Here, an example of derivation of average energy based on the pixel value performed by the calculation unit 202A will be described. For example, it is assumed that the calculation unit 202A derives the pixel value of the X-ray transmission image in a case where there is no subject F as $I_0=5000$ on the basis of the condition information, and sets the pixel value of the X-ray image in a case where there is the subject F to be I=500. In this case, the calculation unit 202A calculates the transmittance of X-rays to be $I/I_0=0.1$. Subsequently, the calculation unit 202A derives that the thickness corresponding to the transmittance of X-rays of 0.1 is 30 mm on the basis of the graph G18 indicating the relationship between the thickness of the subject F and the transmittance of X-rays with respect to the subject F. Further, the calculation unit 202A derives that the average energy corresponding to the pixel value of 500 is 27 keV on the basis of the graph G19 indicating the relationship between the thickness of the subject F and the average energy of transmitted X-rays. Finally, the calculation unit 202A repeats the derivation of the average energy of X-rays for each pixel value, and derives the graph G20 indicating the relationship between the pixel value of the X-ray image and the average energy.

Further, the calculation unit 202A selects the graph G20 corresponding to the condition information acquired by the input unit 201 from a plurality of graph G20 derived in advance in the above procedure. The calculation unit 202A derives the average energy of transmitted X-rays corresponding to the pixel value of each pixel in the X-ray image acquired by the image acquisition unit 203 on the basis of the selected graph G20.

Meanwhile, instead of deriving the relationship between the pixel value and the average energy of X-rays for each piece of condition information in advance, the calculation unit 202A may derive the average energy of X-rays from the condition information acquired by the input unit 201 and the pixel value of each pixel in the X-ray image with reference to the graphs G18 and G19. Specifically, the calculation unit 202A derives the pixel value $I_0$ of the X-ray image in a case where there is no subject on the basis of the condition information. The calculation unit 202A then calculates the transmittance by obtaining the ratio of the pixel value I of each pixel in the X-ray image acquired by the image acquisition unit 203 to the pixel value $I_0$. Further, the calculation unit 202A derives the thickness on the basis of the calculated transmittance and the graph G18 indicating the relationship between the thickness and the transmittance of X-rays. The calculation unit 202A then derives the average energy for each pixel value of each pixel in the X-ray image by deriving the average energy on the basis of the derived thickness and the graph G19 indicating the relationship between the thickness and the average energy.

The noise map generation unit 204A generates a noise standard deviation map from the X-ray image acquired by the image acquisition unit 203 and the average energy of X-rays corresponding to each pixel of the X-ray image derived by the calculation unit 202A (step S104A). Specifically, the noise map generation unit 204A derives the standard deviation of noise values for each pixel considering the thickness of the subject by substituting the pixel value of each pixel in the X-ray image acquired by the image acquisition unit 203 and the average energy derived for each pixel by the calculation unit 202A into the relational expression (4). The noise map generation unit 204A generates the standard deviation of noise values corresponding to each pixel in the X-ray image as a noise standard deviation map.

Figure 18:
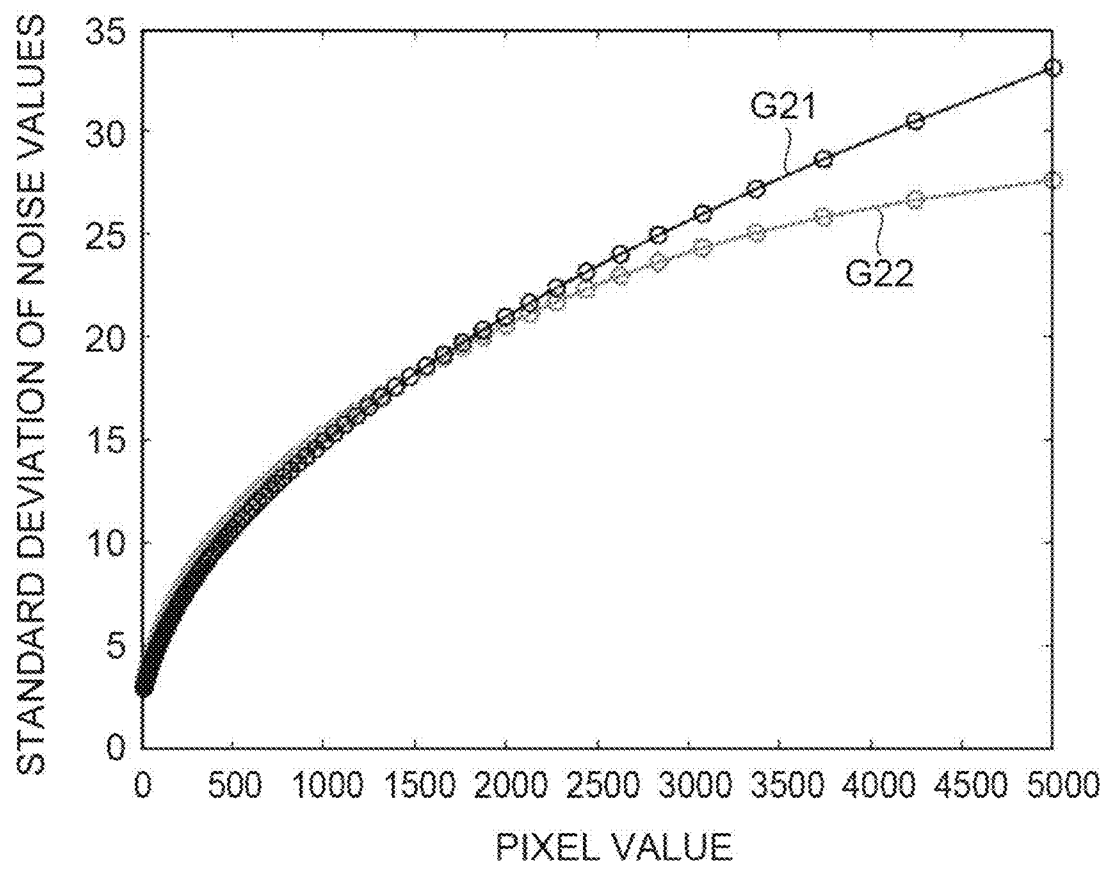
FIG. 18 is a graph illustrating an example of simulation calculation results of a relationship between the pixel value of an X-ray image and the standard deviation of noise values.

FIG. 18 is a graph indicating an example of a relationship between the pixel value and the standard deviation of noise values. This graph shows the relationship between the pixel value of the X-ray image and the standard deviation of noise values derived from the pixel value of the X-ray image by the calculation unit 202A and the noise map generation unit 204A according to the present modification example. In the present modification example, since the standard deviation of noise values is derived in consideration of the thickness of the subject, the thickness of the subject decreases as the pixel value increases, and the average energy in a pixel decreases. Therefore, as can be estimated from the relational expression (4), the first embodiment and the present modification example differ in a change in the standard deviation of noise values when the pixel value increases. In the example shown in FIG. 18, a graph G22 of the present modification example has a smaller degree of increase in the standard deviation of noise values when the pixel value increases than a graph G21 of the first embodiment.

In the control device 20A of the modification example of the first embodiment, the average energy is calculated from the pixel value of each pixel in the X-ray image. Here, for example, in a case where there are a plurality of subjects having different thicknesses or materials in the X-ray image, the average energy differs greatly for each subject, and noise cannot be sufficiently removed from the X-ray image. With such a configuration, since the average energy of X-rays passing through the subject F is calculated for each pixel value of each pixel in the X-ray image, noise removal corresponding to the relationship between the pixel value of each pixel in the X-ray image and the noise can be realized, for example, in consideration of differences in thickness, material, and the like. As a result, it is possible to effectively remove noise in the X-ray image.

Figure 19:
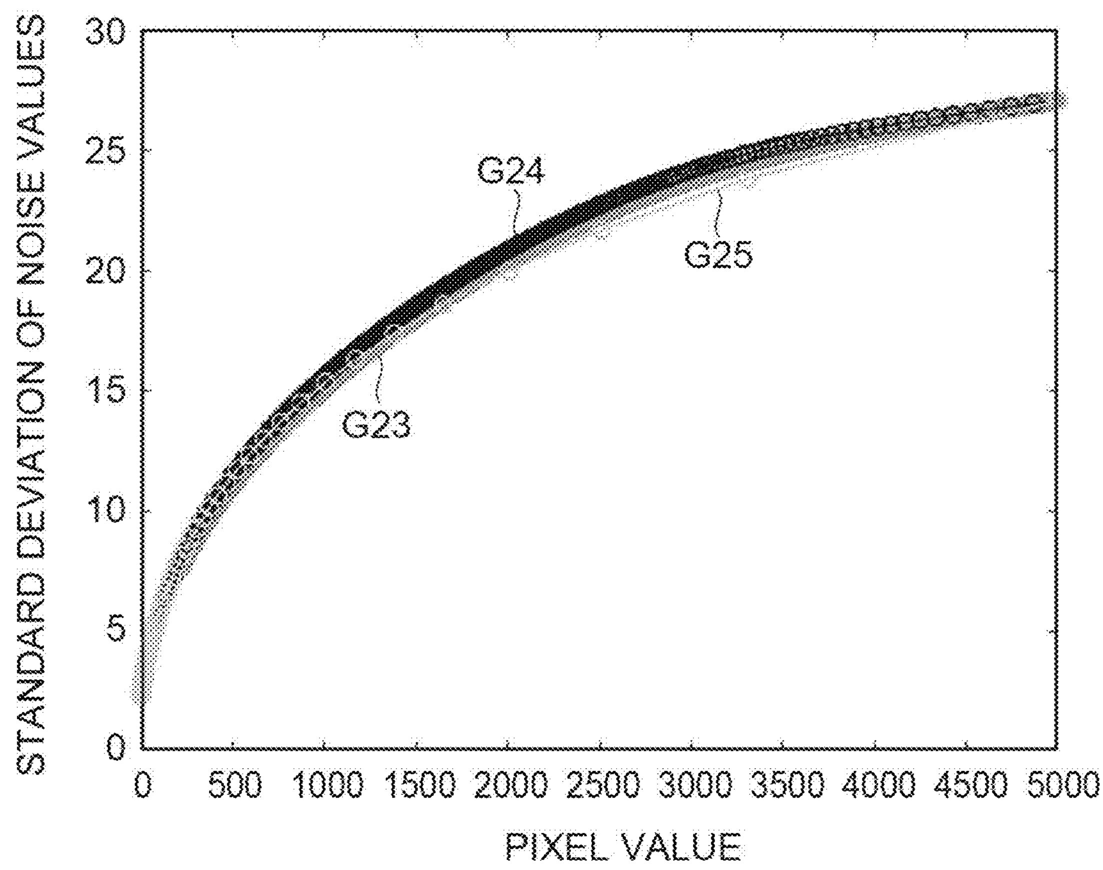
FIG. 19 is a graph illustrating an example of a relationship between the pixel value and the standard deviation of noise values in a case where the material of a subject changes, which is derived by the calculation unit 202A of FIG. 11.

Meanwhile, the control device 20A according to the present modification example derives the average energy from the pixel value of the X-ray image using the graph G20 derived for each of various types of condition information. In this case, the average energy may be derived from the pixel value while ignoring the difference in the material of the subject F. FIG. 19 is a graph illustrating a relationship between the pixel value of the X-ray image and the standard deviation of noise values derived by the calculation unit 202A. Here, changes in the material of the subject F are also taken into consideration as the condition information to derive the relationship. A graph G24 shows a derivation example in a case where the material is aluminum, a graph G23 shows a derivation example in a case where the material is polyethylene terephthalate (PET), and a graph G25 shows a derivation example in a case where the material is copper. In this way, if the tube voltage of the X-ray irradiator 50 and information on a scintillator included in the X-ray detection camera 10 used to capture an image of the subject F are the same even in a case where the material of the subject F changes, the relationship between the pixel value and the average energy of transmitted X-rays does not change significantly, and thus the relationship between the pixel value and the standard deviation of noise values also does not change significantly. In consideration of such properties, the control device 20A can derive the average energy from the pixel value of the X-ray image with a good degree of accuracy even if the difference in the material of the subject F as the condition information is ignored. Even in such a case, according to the control device 20A of the present modification example, it is possible to realize noise removal corresponding to the relationship between the pixel value and the standard deviation of noise. As a result, it is possible to more effectively remove noise in the X-ray image.

Second Embodiment

Figure 20:
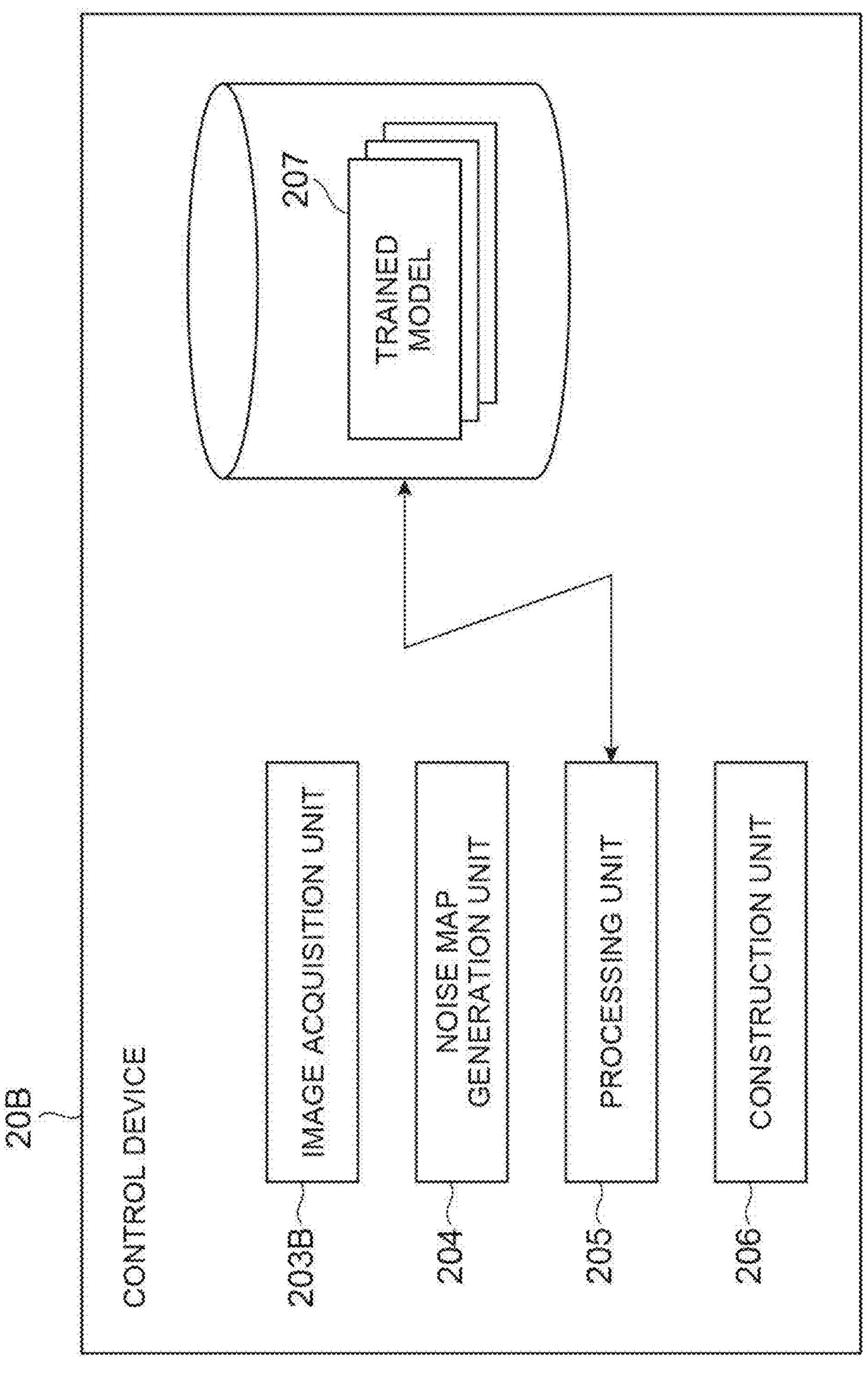
FIG. 20 is a block diagram illustrating a functional configuration of a control device 20B according to a second embodiment of the present disclosure.
Figure 21:
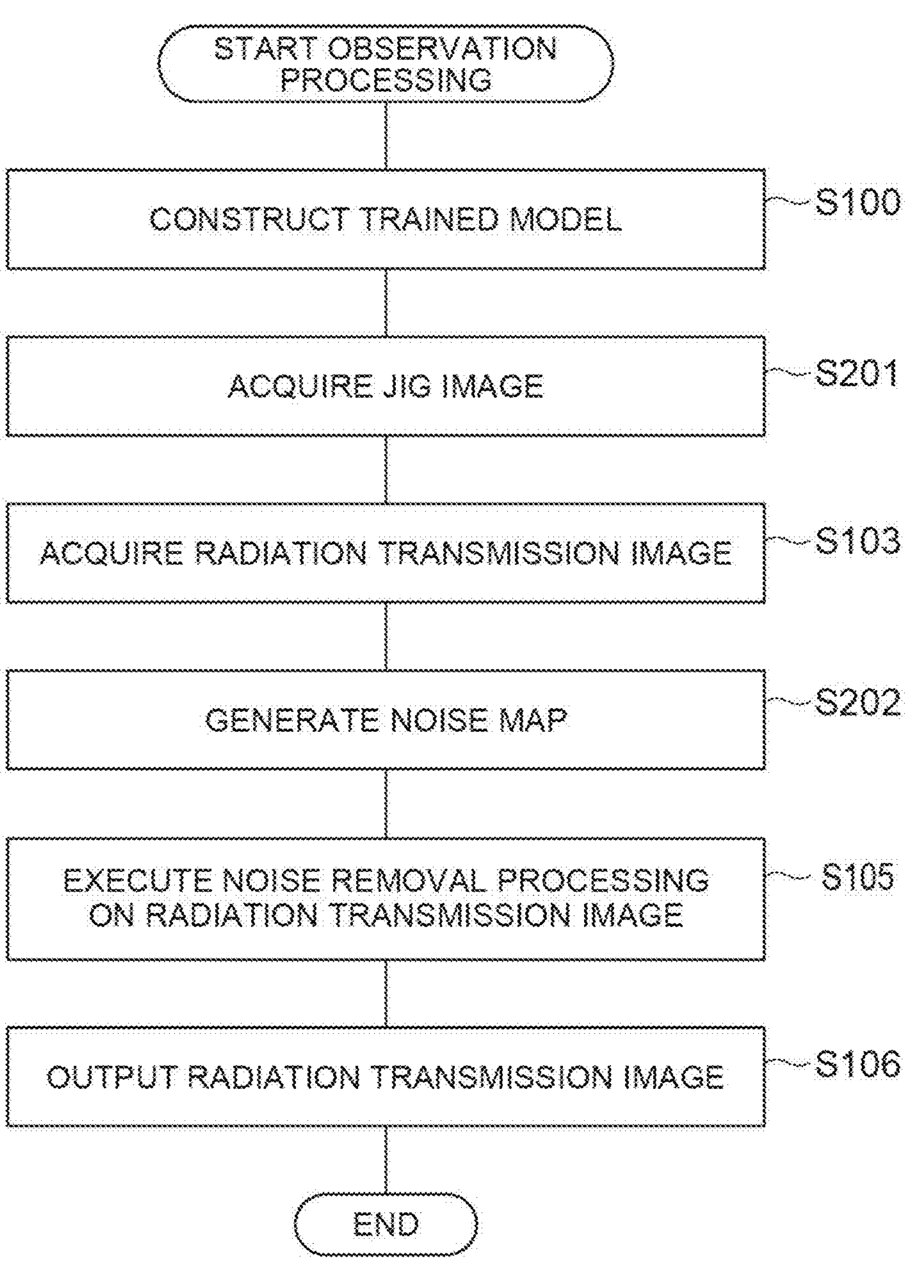
FIG. 21 is a flowchart illustrating a procedure of observation processing performed by an image acquisition device 1 according to the second embodiment of the present disclosure.

FIG. 20 is a block diagram illustrating a functional configuration of a control device 20B in a second embodiment. The control device 20B is different from the above-described first embodiment in that the image acquisition unit 203B has a function of acquiring an X-ray image of a jig, and that the noise map generation unit 204B has a function of deriving a graph indicating the relationship between the pixel value and the standard deviation of noise values from the X-ray image of the jig. FIG. 21 is a flowchart illustrating a procedure of observation processing performed by the image acquisition device 1 including the control device 20B of FIG. 20. As shown in FIG. 21, in the control device 20B according to the second embodiment, the processes shown in steps S201 and S202 are executed in place of the processes of steps S101, S102, and S104 performed by the control device 20 according to the first embodiment shown in FIG. 8.

The image acquisition unit 203B acquires a radiographic image of the jig obtained by irradiating the jig with radiation and capturing an image of the radiation passing through the jig (step S201). Specifically, the image acquisition unit 203B acquires an X-ray image captured by irradiating the jig and the subject F with X-rays using the image acquisition device 1. As the jig, a flat plate-like member or the like of which the thickness and material are known is used. That is, the image acquisition unit 203B acquires an X-ray image of the jig captured using the image acquisition device 1 in advance of the observation process for the subject F. The image acquisition unit 203B then acquires an X-ray image of the subject F captured using the image acquisition device 1. However, the acquisition timings of the X-ray images of the jig and the subject F are not limited to the above, and may be simultaneous or opposite (step S103). In addition, the image acquisition unit 203B acquires an X-ray image obtained by irradiating the subject F with X-rays and capturing an image of the X-rays passing through the subject F in the same way as the image acquisition unit 203.

A jig is set and the image acquisition device 1 captures an image of the jig, and the noise map generation unit 204B derives relationship data indicating the relationship between the pixel value and an evaluation value obtained by evaluating the spread of noise values from the radiographic image of the jig obtained as a result (step S202). Specifically, the noise map generation unit 204B derives a noise standard deviation map indicating the relationship between the pixel value and the standard deviation of noise values from the X-ray image of the jig.

Figure 22:
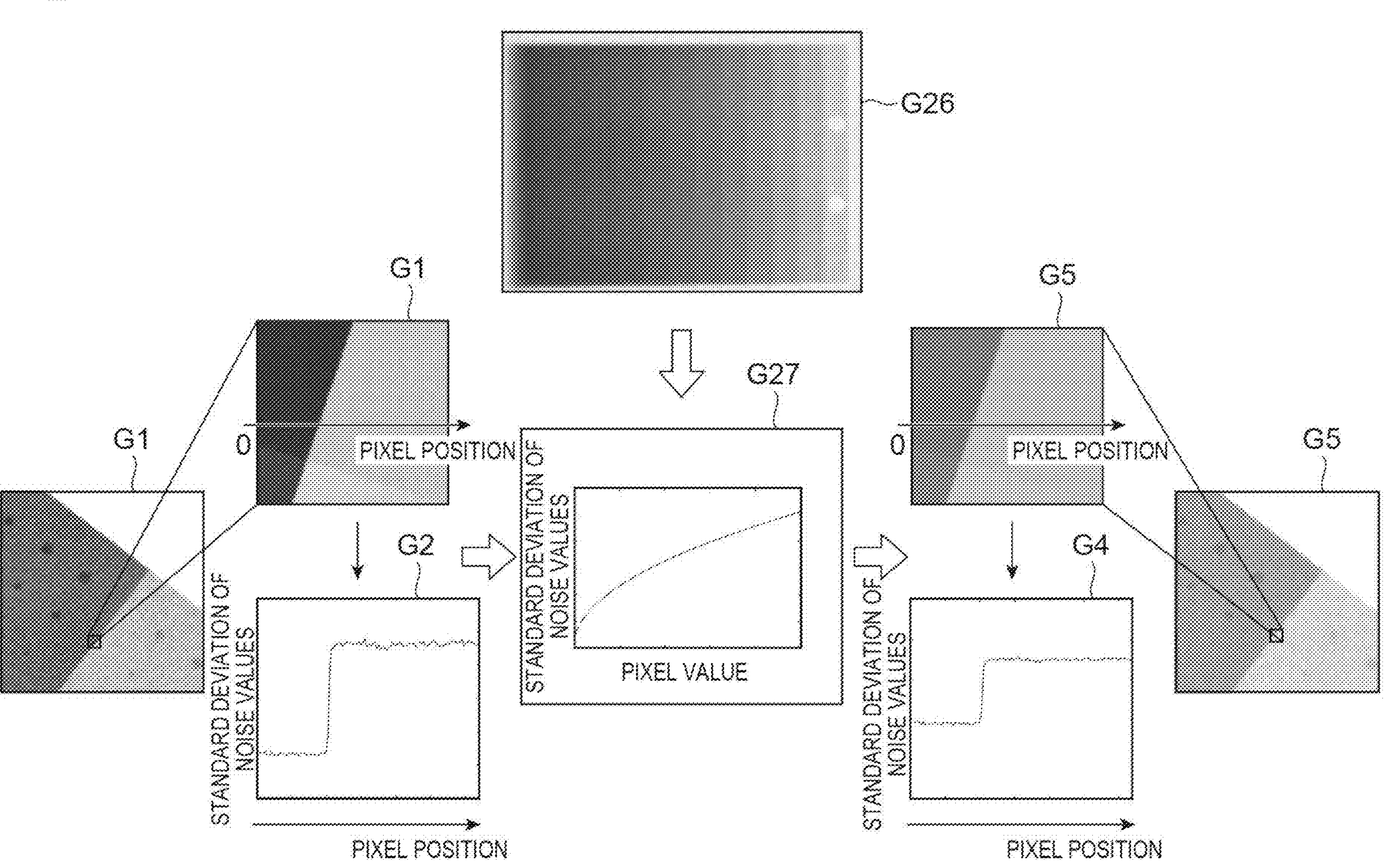
FIG. 22 is a diagram illustrating an example of generation of a noise standard deviation map which is performed by a noise map generation unit 204B of FIG. 20.

FIG. 22 is a diagram illustrating an example of generation of a noise standard deviation map which is performed by the noise map generation unit 204B. The noise map generation unit 204B derives a relationship graph G27 indicating the correspondence relation between the pixel value and the standard deviation of noise values from an X-ray image G26 of the jig. In the same way as in the first embodiment, the noise map generation unit 204B then derives the relationship data G2 indicating the correspondence relation between each pixel position and pixel value from the X-ray image G1 acquired by the image acquisition unit 203B. Further, the noise map generation unit 204 derives the standard deviation of noise values corresponding to a pixel at each pixel position in the X-ray image by applying the correspondence relation indicated by the relationship graph G27 to each pixel in the relationship data G2. As a result, the noise map generation unit 204 associates the derived standard deviation of noise with each pixel position, and derives a relationship data G4 indicating the correspondence relation between each pixel position and the standard deviation of noise. The noise map generation unit 204 then generates a noise standard deviation map G5 on the basis of the derived relationship data G4.

Figure 23:
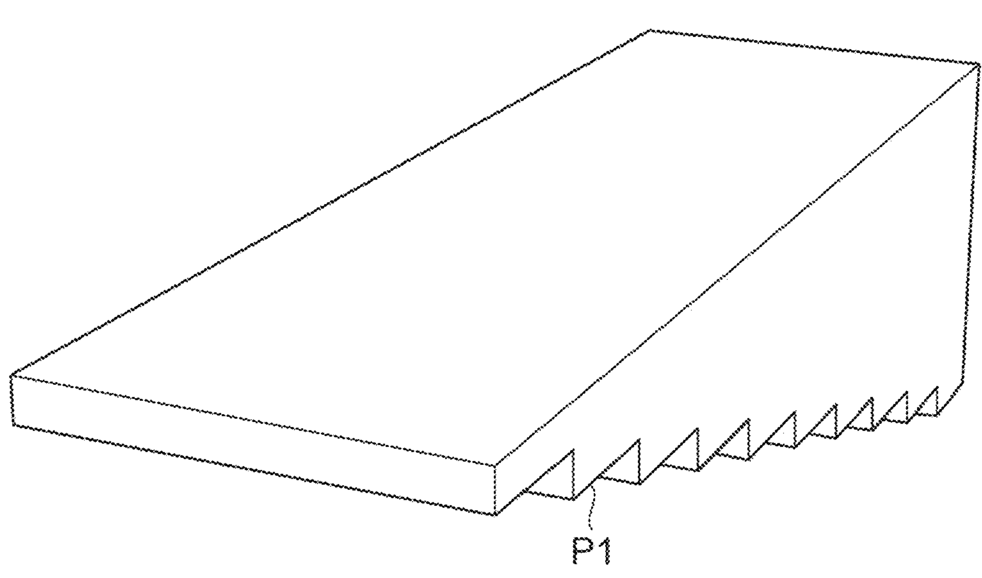
FIG. 23 is a perspective view illustrating an example of a structure of a jig used for image capturing in the image acquisition device 1 according to the second embodiment.
Figure 24:
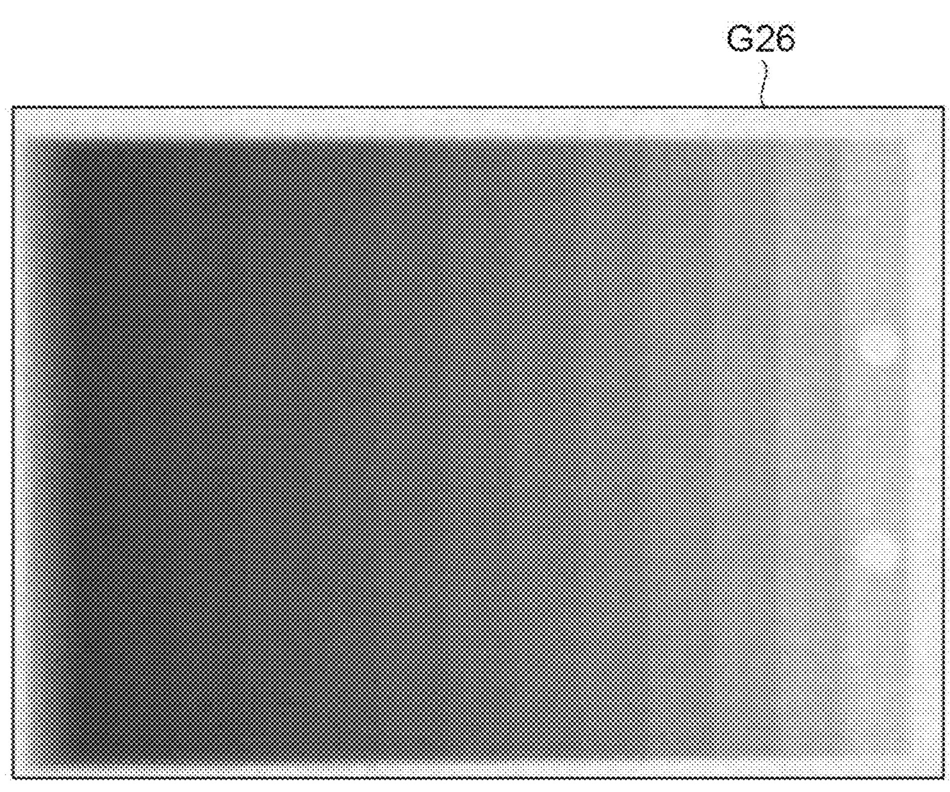
FIG. 24 is a diagram illustrating an example of a captured image of the jig of FIG. 23.

The derivation of the relationship graph G27 indicating the relationship between the pixel value and the standard deviation of noise values from the X-ray image G26 of the jig which is performed by the noise map generation unit 204B will be described. FIG. 23 shows an example of the structure of a jig used for image capturing in the second embodiment. For the jig, for example, a member P1 of which the thickness changes stepwise in one direction can be used. FIG. 24 shows an example of an X-ray image of the jig in FIG. 23. First, in the X-ray image G26 of the jig, the noise map generation unit 204B derives a pixel value in a case where there is no noise for each step of the jig (hereinafter referred to as a true pixel value), and derives the standard deviation of noise values on the basis of the true pixel value. Specifically, the noise map generation unit 204B derives the average value of the pixel values at a certain step of the jig. The noise map generation unit 204B then uses the derived average value of the pixel values as the true pixel value at that step. In that step, the noise map generation unit 204B derives the difference between each pixel value and the true pixel value as a noise value. The noise map generation unit 204B derives the standard deviation of the noise values from the derived noise value for each pixel value.

The noise map generation unit 204B then derives a relationship between the true pixel value and the standard deviation of noise values as the relationship graph G27 between the pixel value and the standard deviation of noise values. Specifically, the noise map generation unit 204B derives the true pixel value and the standard deviation of noise values for each step of the jig. The noise map generation unit 204B plots the derived relationship between the true pixel value and the standard deviation of noise values on a graph and draws an approximation curve to derive the relationship graph G27 indicating the relationship between the pixel value and the standard deviation of noise values. Meanwhile, for the approximation curve, exponential approximation, linear approximation, log approximation, polynomial approximation, power approximation, or the like is used.

In the control device 20B of the second embodiment, relationship data is generated on the basis of a radiographic image obtained by capturing an image of an actual jig. This makes it possible to obtain optimum relationship data for noise removal from the radiographic image of the subject F. As a result, it is possible to more effectively remove noise in the radiographic image.

Meanwhile, the noise map generation unit 204B may derive the relationship between the pixel value and the standard deviation of noise values from the captured image in a case where the tube current or the exposure time is change in the absence of a subject without using the jig. With such a configuration, since the relationship data is generated on the basis of the radiographic image obtained by actual image capturing and the noise map is generated, it is possible to realize noise removal corresponding to the relationship between the pixel value and the spread of noise. As a result, it is possible to more effectively remove noise in the radiographic image.

Specifically, the image acquisition unit 203B may acquire a plurality of radiographic images captured without a subject (step S201), and the noise map generation unit 204B may derive the relationship between the pixel value and the standard deviation of noise values from the radiographic image acquired by the image acquisition unit 203B (step S202). The plurality of radiographic images are a plurality of images that differ from each other in at least one of the conditions of the radiation source and the imaging conditions. As an example, the image acquisition unit 203B acquires a plurality of X-ray images captured using the image acquisition device 1 without the subject F in advance of the observation process for the subject F while the tube current or the exposure time is changed. The noise map generation unit 204B then derives the true pixel value for each X-ray image, and derives the standard deviation of noise on the basis of the true pixel value in the same way as in the second embodiment. Further, in the same way as in the second embodiment, the noise map generation unit 204B plots the relationship between the true pixel value and the standard deviation of noise on a graph and draws an approximation curve to derive a relationship graph indicating the relationship between the pixel value and the standard deviation of noise values. Finally, in the same way as in the first embodiment, the noise map generation unit 204B generates a noise standard deviation map from the X-ray image acquired by the image acquisition unit 203B on the basis of the derived relationship graph.

Third Embodiment

Figure 25:
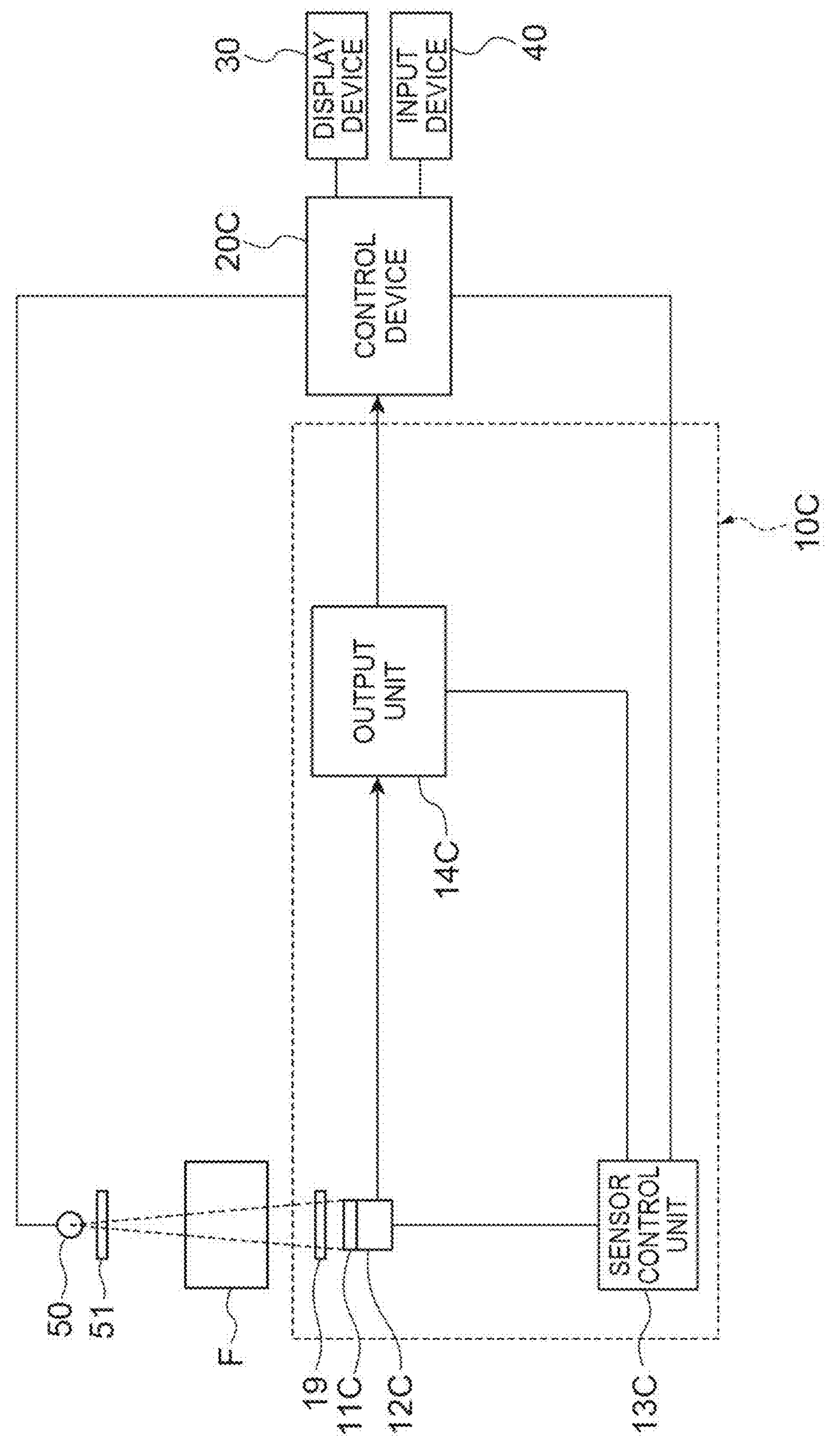
FIG. 25 is a schematic configuration diagram of an image acquisition device 1C according to a third embodiment.
Figure 26:
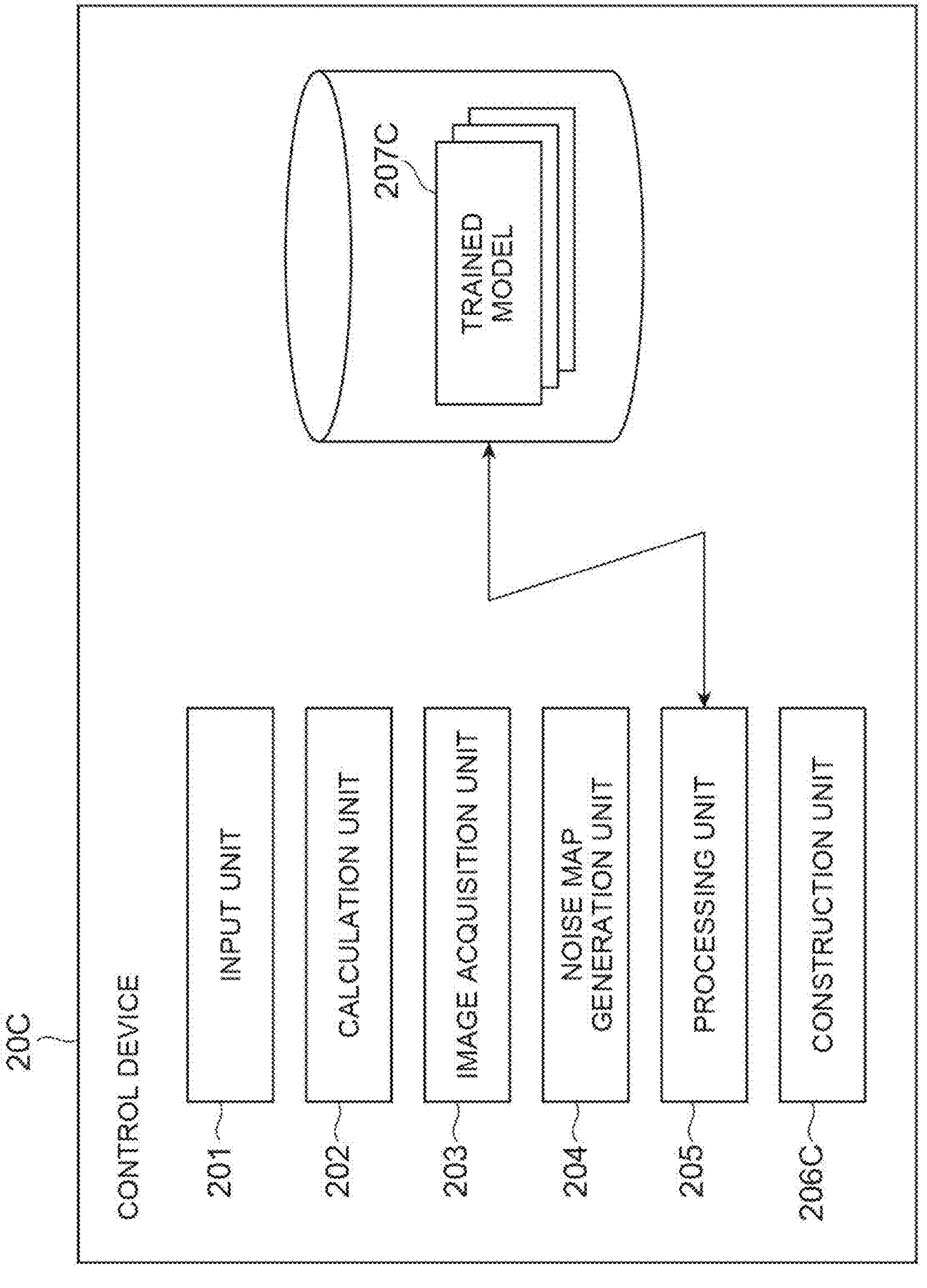
FIG. 26 is a block diagram illustrating a functional configuration of a control device 20C according to the third embodiment.

FIG. 25 is a configuration diagram of an image acquisition device 1C which is a radiographic image processing system according to a third embodiment. FIG. 26 is a block diagram illustrating an example of a functional configuration of a control device 20C according to the third embodiment. The image acquisition device 1C according to the third embodiment is different from the first embodiment or the second embodiment described above in that an X-ray detection camera 10C (imaging device) having a two-dimensional sensor 12C and the like and the control device 20C having a construction unit 206C and a trained model 207C are provided, and that the belt conveyor 60 is not provided.

The image acquisition device 1C uses an X-ray transmission image to perform a foreign substance inspection, a weight inspection, a product inspection, or the like on the subject F, and examples of applications include a food inspection, a baggage inspection, a substrate inspection, a battery inspection, a material inspection, and the like. Further, examples of applications of the image acquisition device 1C include a medical application, a dental application, an industrial application, and the like. Examples of the medical application include chest x-ray, mammography, computed tomography (CT), dual energy CT, tomosynthesis, and the like. The dental application is transmission, panorama, CT, or the like. The industrial application is a non-destructive test, security, a battery inspection, or the like.

The image acquisition device 1C according to the third embodiment outputs an X-ray image obtained by capturing an X-ray transmission image based on X-rays passing through the subject F in a stationary state. However, the image acquisition device 1C may be configured to have the belt conveyor 60 like the image acquisition device 1 described above and capture an image of the transported subject F.

Figure 27:
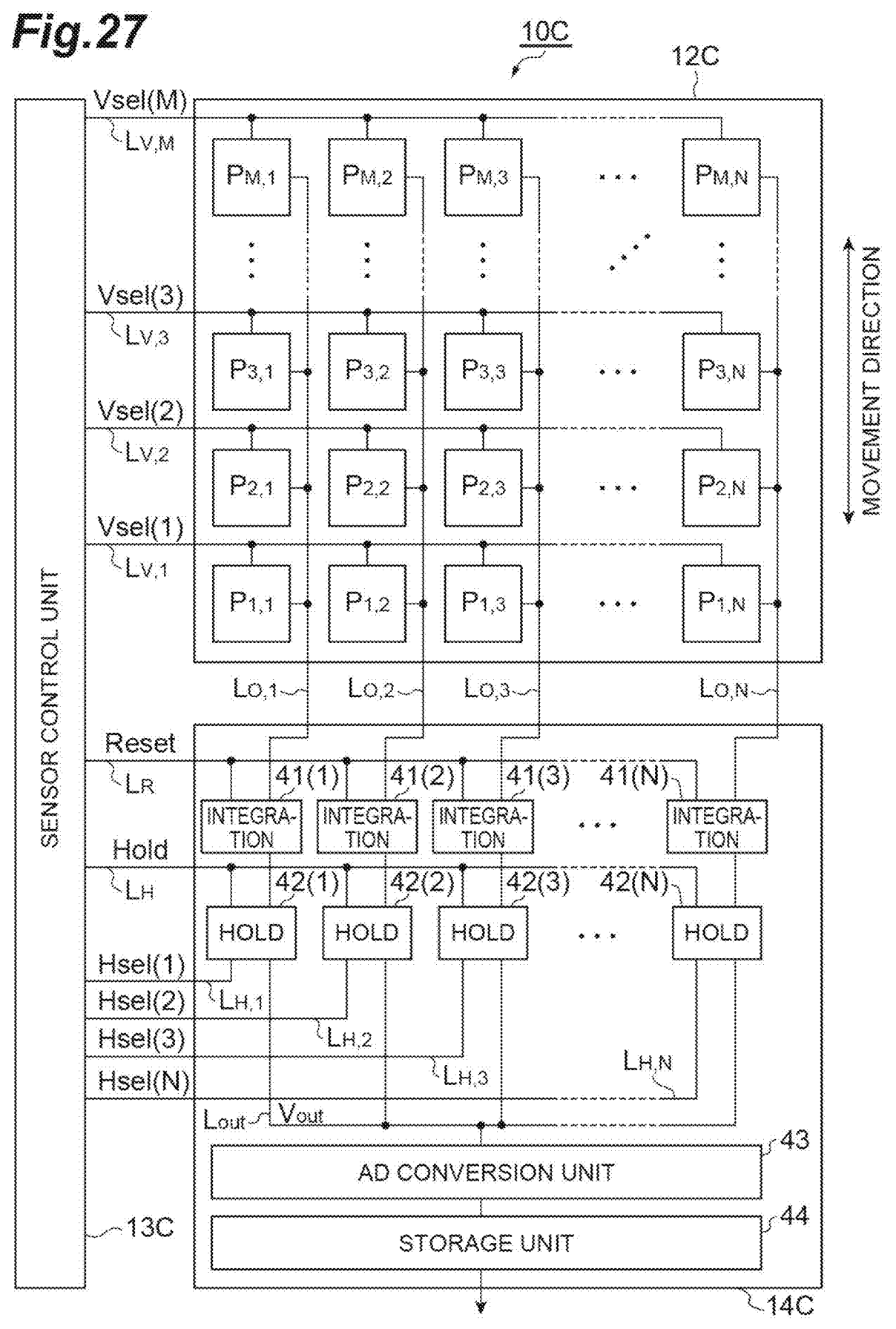

FIG. 27 is a block diagram illustrating a configuration of the X-ray detection camera 10C. As shown in FIGS. 25 and 27, the X-ray detection camera 10C includes a filter 19, a scintillator layer 11C, a two-dimensional sensor 12C, a sensor control unit 13C, and an output unit 14C. The sensor control unit 13C is electrically connected to the two-dimensional sensor 12C, the output unit 14C, and the control device 20C. The output unit 14C is also electrically connected to the two-dimensional sensor 12C and the control device 20C.

The scintillator layer 11C is fixed onto the two-dimensional sensor 12C by an adhesive or the like, and converts X-rays passing through the subject F into scintillation light (detailed configuration will be described later). The scintillator layer 11C outputs the scintillation light to the two-dimensional sensor 12C. The filter 19 transmits a predetermined wavelength region of X-rays toward the scintillator layer 11C.

The two-dimensional sensor 12C detects the scintillation light from the scintillator layer 11C, converts the light into electric charge, and outputs it as a detection signal (electrical signal) to the output unit 14C. The two-dimensional sensor 12C is, for example, a line sensor or a flat panel sensor, and is disposed on a substrate 15C. The two-dimensional sensor 12C has M×N pixels $P_{1,1}$ to $P_{M,N}$ arrayed two-dimensionally in M rows and N columns. The M×N pixels $P_{1,1}$ to $P_{M,N}$ are arrayed at a constant pitch both in the row direction and the column direction. The pixel $P_{m,n}$ is located at the m-th row and the n-th column Each of the N pixels $P_{m,1}$ to $P_{m,N}$ in the m-th row is connected to the sensor control unit 13C through an m-th row selection wiring $L_{V,m}$. The output terminal of each of the M pixels $P_{1,n}$ to $P_{M,n}$ in the n-th column is connected to the output unit 14C through an n-th column readout wiring $L_{O,n}$. Meanwhile, M and N are integers equal to or greater than 2, m is an integer equal to or greater than 1 and equal to or less than M, and n is an integer equal to or greater than 1 and equal to or less than N.

The output unit 14C outputs a digital value generated on the basis of the amount of electric charge which is input through the readout wiring $L_{O,n}$. The output unit 14C includes N integration circuits 41(1) to 41(N), N hold circuits 42(1) to 42(N), an AD conversion unit 43, and a storage unit 44. Each of the integration circuits 41(*n*) has a common configuration. In addition, each of the hold circuits 42(*n*) has a common configuration.

Each of the integration circuits 41(*n*) accumulates electric charges input to the input terminal through any of the column readout wiring $L_{O,n}$. Each of the integration circuits 41(*n*) outputs a voltage value corresponding to the amount of accumulated electric charge from the output terminal to the hold circuit 42(*n*). Each of the N integration circuits 41(1) to 41(N) is connected to the sensor control unit 13C through a reset wiring $L_R$.

Each of the hold circuits 42(*n*) has an input terminal connected to the output terminal of the integration circuit 41(*n*). Each of the hold circuits 42(*n*) holds the voltage value which is input to the input terminal, and outputs the held voltage value from the output terminal to the AD conversion unit 43. Each of the N hold circuits 42(1) to 42(N) is connected to the sensor control unit 13C through a hold wiring $L_H$. In addition, each of the hold circuits 42(*n*) is connected to the sensor control unit 13C through an n-th column selection wiring $L_{H,n}$.

The AD conversion unit 43 inputs a voltage value which is output from each of the N hold circuits 42(1) to 42(N), and performs an AD conversion process on the input voltage value (analog value). The AD conversion unit 43 outputs a digital value corresponding to the input voltage value to the storage unit 44. The storage unit 44 inputs and stores the digital value which is output from the AD conversion unit 43, and sequentially outputs the stored digital value.

The sensor control unit 13C outputs an m-th row selection control signal Vsel(m) to each of the N pixels $P_{m,1}$ to $P_{m,N}$ in the m-th row through the m-th row selection wiring $L_{V,m}$. The sensor control unit 13C outputs a reset control signal Reset to each of the N integration circuits 41(1) to 41(N) through the reset wiring $L_R$. The sensor control unit 13C outputs a hold control signal Hold to each of the N hold circuits 42(1) to 42(N) through the hold wiring $L_H$. The sensor control unit 13C outputs an n-th column selection control signal Hsel(n) to the hold circuit 42(*n*) through the n-th column selection wiring $L_{H,n}$. In addition, the sensor control unit 13C controls the AD conversion process in the AD conversion unit 43 and also controls writing and reading-out of digital values in the storage unit 44.

Figure 28:
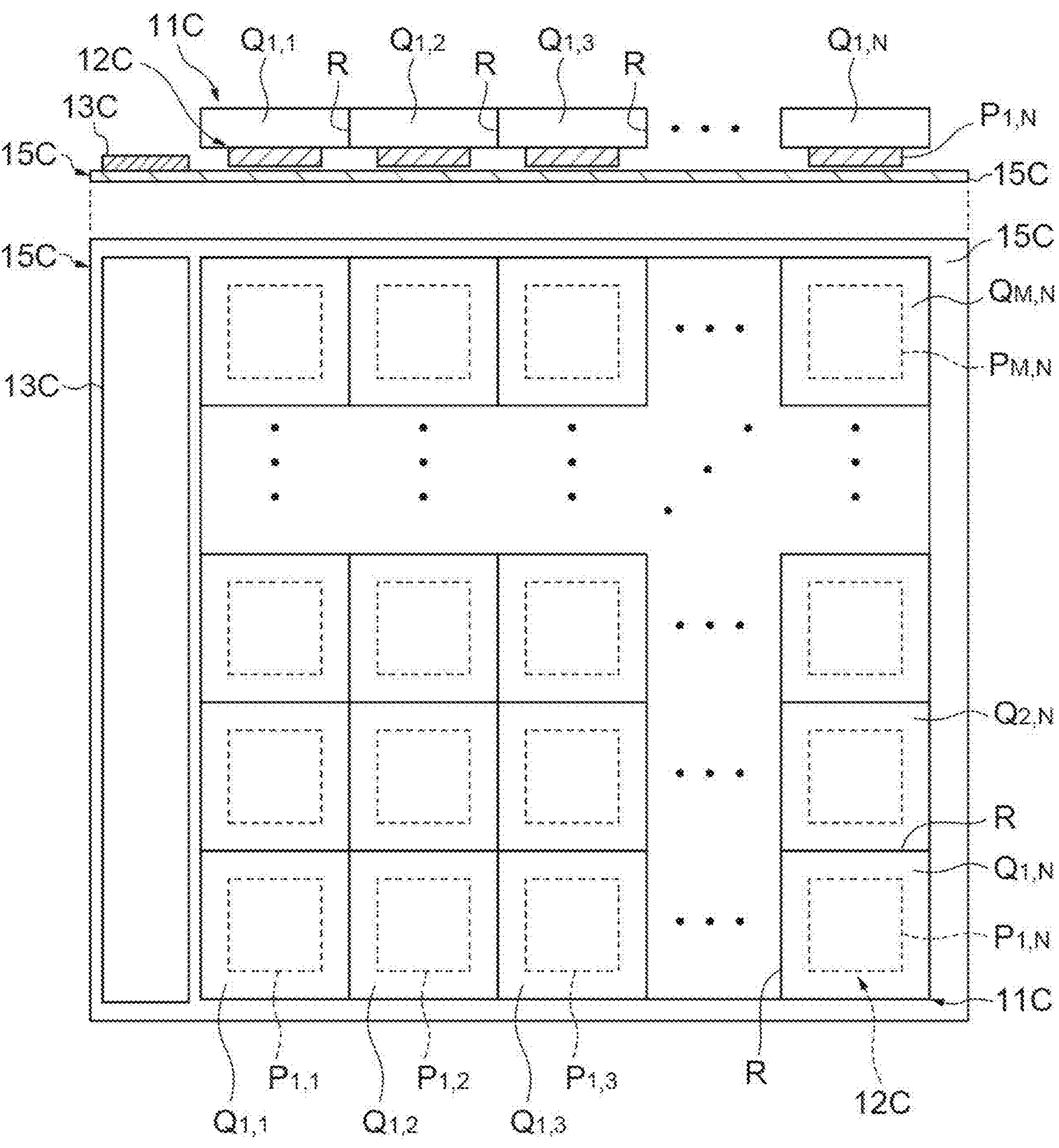
FIG. 28 is a diagram illustrating a configuration of a scintillator layer 11 disposed on a two-dimensional sensor 12C.

The configuration of the scintillator layer 11C disposed on the two-dimensional sensor 12C having the above configuration will be described. FIG. 28 is a diagram illustrating the configuration of the scintillator layer 11C, the top being a cross-sectional view in the thickness direction of the substrate 15C, and the bottom being a plan view illustrating the substrate 15C viewed from the lateral side where the two-dimensional sensor 12C is disposed. In this way, the scintillator layer 11C is formed with K×L (K and L are integers equal to or greater than 1) rectangular scintillator units $Q_{1,1}$ to $Q_{K,L}$ separately arranged corresponding to the M×N pixels $P_{1,1}$ to $P_{M,N}$ lined up along the substrate 15C and separation units R located between these scintillator units $Q_{1,1}$ to $Q_{K,L}$. Meanwhile, the number L may be equal to or greater than 1 and equal to or less than N, and the number K may be equal to or greater than 1 and equal to or less than M. Further, the number L may be an integer equal to or greater than 1, N divided by an integer, and the number K may be an integer equal to or greater than 1, M divided by an integer. In this case, it is possible to suppress blurring caused by the spread of light in accordance with the interval between the separation units R of the scintillator layer 11C. In addition, the number L may be an integer greater than N, and the number K may be an integer greater than M. In this case, although the interval between the separation units R of the scintillator layer 11C is smaller than the interval between the plurality of pixels $P_{1,1}$ to $P_{M,N}$, the alignment of the scintillator layer 11C and the plurality of pixels $P_{1,1}$ to $P_{M,N}$ is facilitated. In the present embodiment, for example, the relations of L=N and K=M are established, but there is no limitation thereto.

The K×L scintillator units $Q_{1,1}$ to $Q_{K,L}$ are made of a scintillator material that makes it possible to convert incident X-rays into scintillation light, and are arranged so as to cover the entire pixels $P_{1,1}$ to $P_{M,N}$. As an example, M×N scintillator units $Q_{1,1}$ to $Q_{M,N}$ are arranged so as to cover the entire corresponding pixels $P_{1,1}$ to $P_{M,N}$. The separation units R are formed in a mesh shape so as to separate the K×L scintillator units $Q_{1,1}$ to $Q_{K,L}$, and are made of a material that makes it possible to shield scintillation light. In addition, the separation units R may contain a material that reflects the scintillation light. Further, the separation units R may be made of a material that makes it possible to shield radiation. As the materials constituting such a scintillator layer 11C and a method of manufacturing the scintillator layer 11C, for example, materials and manufacturing methods disclosed in Japanese Unexamined Patent Publication No. 2001-99941 or Japanese Unexamined Patent Publication No. 2003-167060 can be used. However, the materials of the scintillator layer 11C and manufacturing methods therefor are not limited to those disclosed in the above document.

The control device 20C generates an X-ray image on the basis of the digital signal which is output from the X-ray detection camera 10C (more specifically, the storage unit 44 of the output unit 14C). The generated X-ray image is output to the display device 30 after noise removal processing to be described later is undergone, and displayed by the display device 30. In addition, the control device 20C controls the X-ray irradiator 50 and the sensor control unit 13C. Meanwhile, the control device 20C in the third embodiment is a device provided independently outside the X-ray detection camera 10C, but may be integrated inside the X-ray detection camera 10C.

Figure 29:
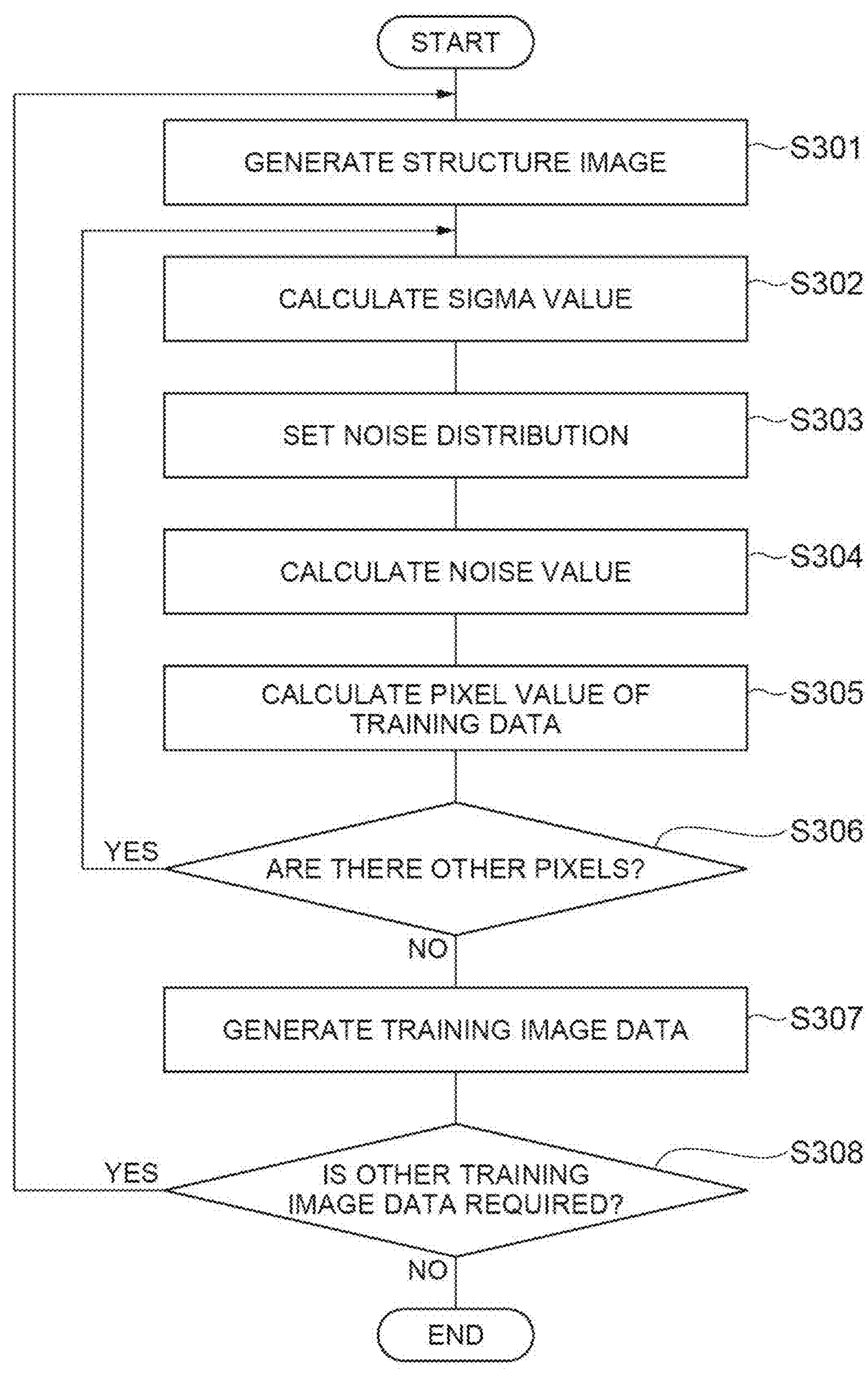
FIG. 29 is a flowchart illustrating a procedure of creating image data which is training data used to construct a trained model 207C by a construction unit 206C.

Here, a function of construction of the trained model 207C performed by the construction unit 206C in the third embodiment will be described. FIG. 29 is a flowchart illustrating a procedure of creating image data which is training data (training image in the first embodiment and the second embodiment) used for the construction unit 206C to construct the trained model 207C.

The image data (also referred to as training image data) which is training data is created by a computer in the following procedure. First, an image of a structure having a predetermined structure (structure image) is created (step S301). For example, an image of a structure (for example, a jig) having a predetermined structure may be created by simulation calculation. In addition, a structure image may be created by acquiring an X-ray image of a structure such as a chart having a predetermined structure. Next, a sigma value which is a standard deviation of pixel values is calculated for one pixel selected from a plurality of pixels constituting this structure image (step S302). Noise distribution is then set on the basis of the sigma value obtained in step S302 (step S303). This noise distribution is set so that the probability that the pixel value to which noise is added exceeds the original pixel value is higher than the normal distribution (Poisson distribution), and in particular, the probability that the pixel value to which noise is added is more than 1.2 times the original pixel value increases (the details will be described later). In this way, training data with various noise conditions can be generated by setting the noise distribution on the basis of the sigma value. Subsequently, a noise value set at random is calculated along the noise distribution set on the basis of the sigma value in step S303 (step S304). Further, by adding the noise value obtained in step S304 to the pixel value of one pixel, the pixel value constituting the image data which is training data is generated (step S305). The processes from step S302 to step S305 are performed for each of a plurality of pixels constituting the structure image (step S306), and training image data serving as training data is generated (step S307). In addition, in a case where more training image data is required, it is determined that the processes from step S301 to step S307 are performed on another structure image (step S308), and another training image data serving as training data is generated. Meanwhile, another structure image may be an image of a structure having the same structure, or may be an image of a structure having another structure.

Figure 30:
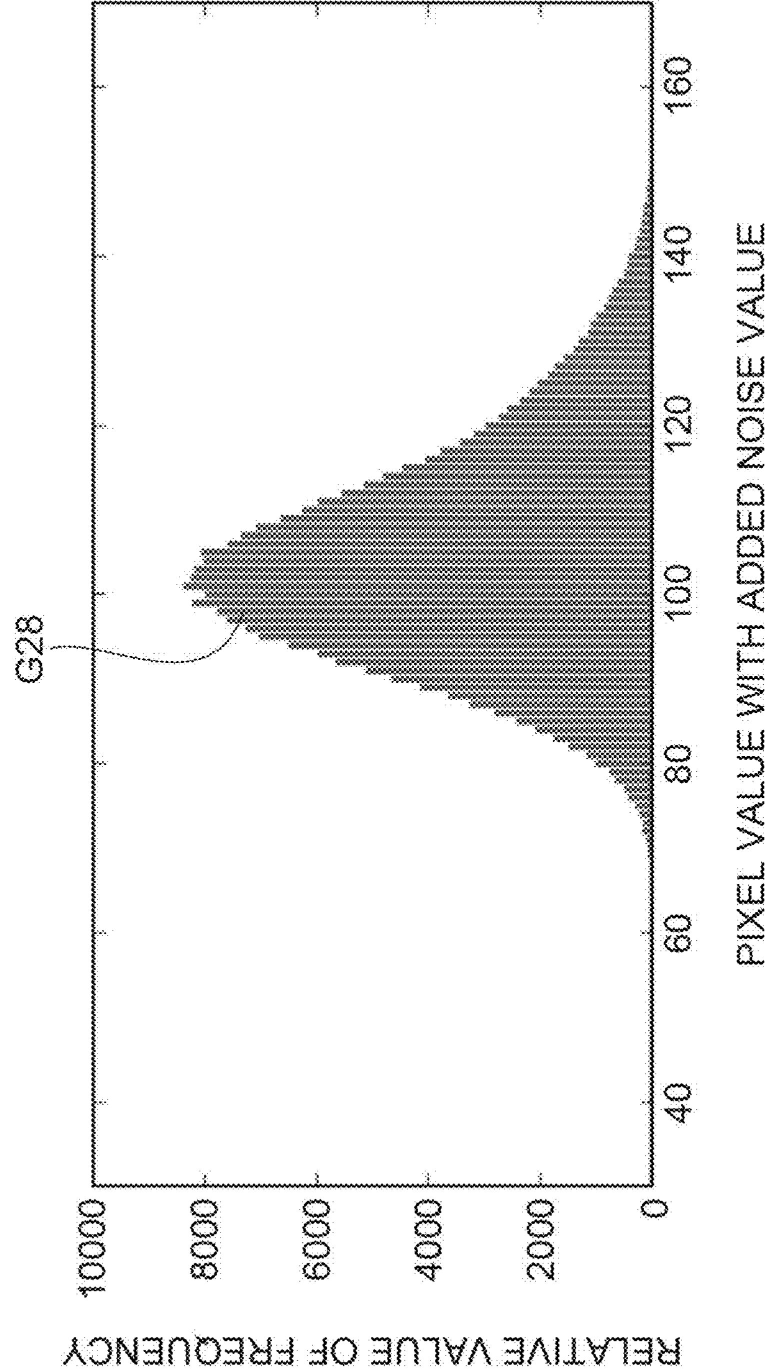
FIG. 30 is a graph illustrating an example of noise distribution used to generate training data.
Figure 31:
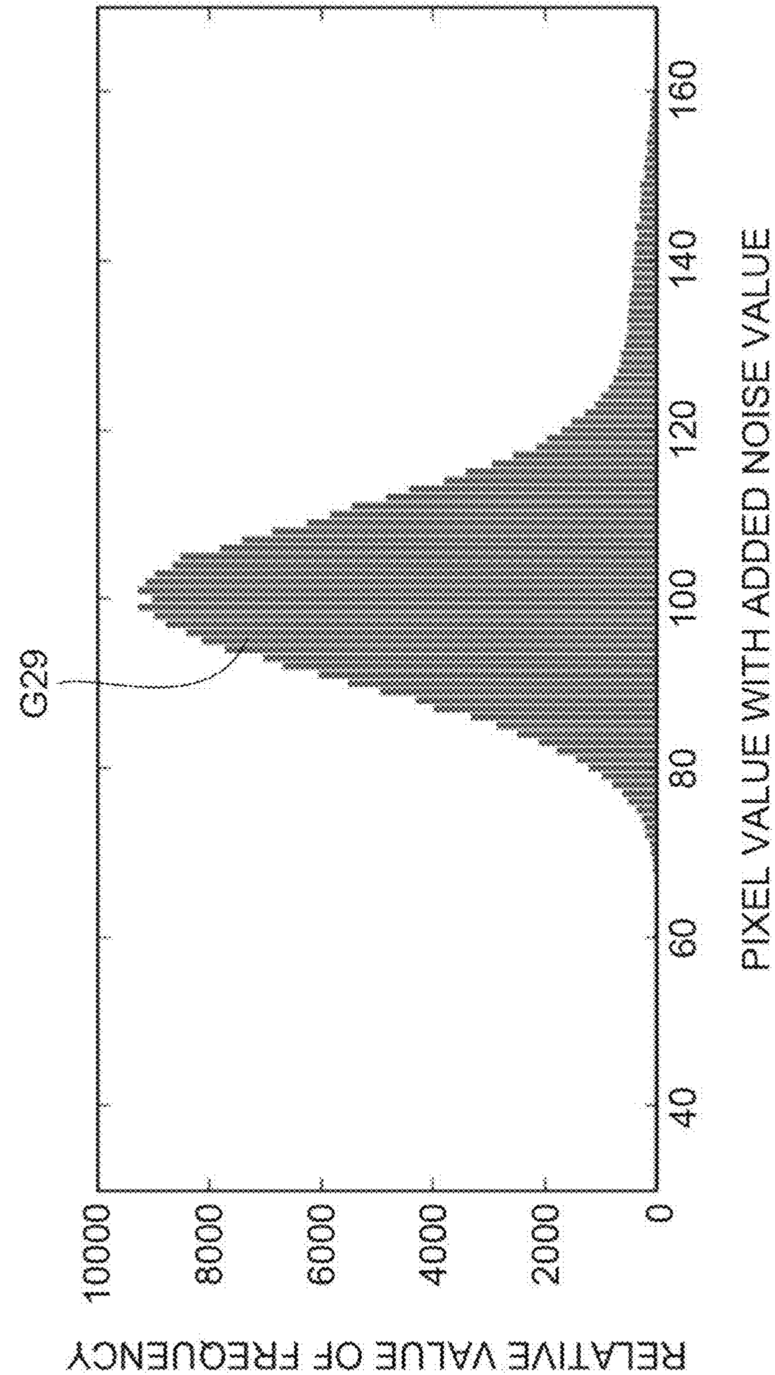
FIG. 31 is a graph illustrating an example of noise distribution used to generate training data.

FIGS. 30 and 31 are diagrams illustrating examples of the noise distribution set in step S303 described above. The horizontal axis in FIGS. 30 and 31 indicates a pixel value to which a noise value is added (hereinafter referred to as a noise pixel value) with the pixel value before the noise value of a pixel is added being set to 100. The vertical axis in FIGS. 30 and 31 is a relative value of the frequency of the noise pixel value. The relative value of the frequency of the noise pixel value is a value indicating the relative frequency of the pixel value after noise is added to the pixel value. When the relative value at each noise pixel value is divided by the sum of the relative values at each noise pixel value, the result is a value indicating the probability that the pixel value will be each noise pixel value when the noise value is added. Noise distributions G28 and G29 shown in FIGS. 30 and 31 are set in consideration of the fact that X-rays detected by a sensor in image capturing using a scintillator appear as white spots in the X-ray image. For this reason, compared with the normal distribution (Poisson distribution), the above noise distributions G28 and G29 have a higher probability that the noise pixel value exceeds the original pixel value, and particularly has a higher probability that the noise pixel value is equal to or greater than 120 (noise pixel value equivalent to a case where white spots occur in the X-ray image). Here, the case where X-rays detected by a sensor appear as white spots in the X-ray image is a case where X-rays pass through a scintillator without being absorbed by the scintillator and are directly converted into electrons by the sensor. In a case where the X-rays are absorbed by the scintillator and converted to visible light, the sensor detects the visible light. On the other hand, in a case where the X-rays are not absorbed by the scintillator, the X-rays are directly converted into electrons by the sensor. That is, the sensor that detects visible light detects not only scintillation light (visible light) generated in the scintillator layer 11C but also X-rays passing through the scintillator layer 11C. In this case, since the number of electrons generated from the X-rays incident on the sensor is greater than in a case where the X-rays are converted into visible light by the scintillator, the X-rays passing through the scintillator layer 11C appear as white spots in the X-ray image. The occurrence of the white spots causes noise in the X-ray image. Therefore, the trained model 207C is constructed using the noise distribution described above, and noise removal is executed using the construct trained model 207C, whereby the white spots appearing in the X-ray image can be removed as noise. Meanwhile, a case where white spots are likely to occur is, for example, a case where the tube voltage of the X-ray irradiator is high, or the like.

Meanwhile, it is necessary to prepare a large amount of image data which is training data used to construct the trained model 207C. In addition, the structure image is preferably an image with little noise, ideally an image with no noise. Therefore, generating a structure image through simulation calculation enables a large number of noise-free images to be generated, and thus generating a structure image through simulation calculation is effective.

The image acquisition device 1C of the third embodiment includes the two-dimensional sensor 12C as a flat panel sensor. The scintillator units $Q_{1,1}$ to $Q_{M,N}$ and the separation units R of the scintillator layer 11C are provided for each of the pixels $P_{1,1}$ to $P_{M,N}$ of the two-dimensional sensor 12C. This reduces blurring in the X-ray image acquired by the image acquisition device 1C. The result is higher contrast and higher noise intensity in the X-ray image. Here, in the image acquisition device 1C of the third embodiment, noise removal corresponding to the relationship between the pixel value and the standard deviation of noise values in the X-ray image is executed using the trained model 207C constructed in advance through machine learning. This reduces only the noise intensity in the X-ray image. As described above, the image acquisition device 1C can acquire an X-ray image with reduced noise intensity and enhanced contrast.

Figure 32:
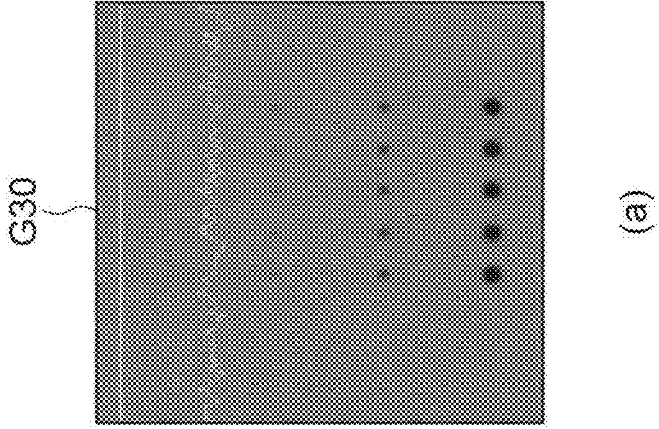
FIG. 32 is a diagram illustrating an example of X-ray images generated by simulation calculation.
Figure 32:
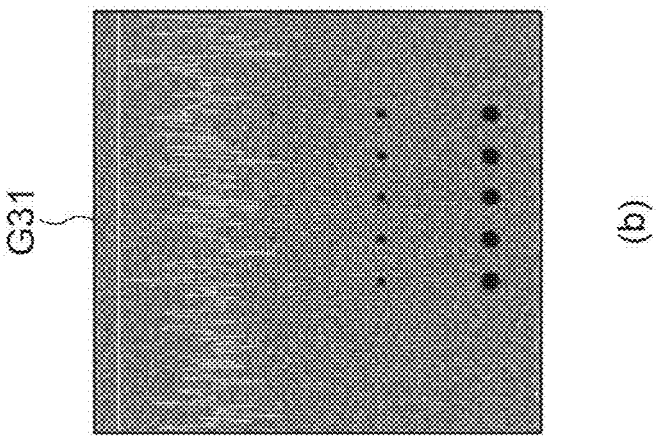
Figure 32:
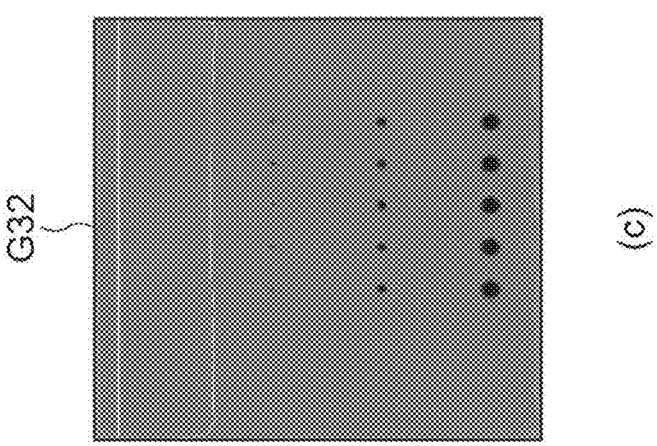

FIGS. 32(*a*), 32(*b*), and 32(*c*) show examples of simulation results of the X-ray image acquired by the image acquisition device 1C. An X-ray image G30 shown in FIG. 32(*a*) is an X-ray image generated by simulation calculation on the basis of the condition that image capturing has been performed using a scintillator made of cesium iodide (CsI) as the scintillator layer 11C. The scintillator made of CsI has, for example, a sheet-like shape extending along the pixels of the two-dimensional sensor 12C. The thickness of the scintillator made of CsI is set to 450 μm. An X-ray image G31 shown in FIG. 32(*b*) is an X-ray image generated by simulation calculation on the basis of the condition that the pixel scintillator having the structure shown in FIG. 28 is used as the scintillator layer 11C. An X-ray image G32 shown in FIG. 32(*c*) is an X-ray image generated by simulation calculation on the basis of the condition that image capturing has been performed using the pixel scintillator as the scintillator layer 11C and noise removal corresponding to the relationship between the pixel value and the standard deviation of noise values has been performed (condition that the same noise removal as the image acquisition device 1C according to the third embodiment has been performed). In this case, the pixel scintillator is provided for each pixel. The thickness of the pixel scintillator is set to, for example, 200 μm. The thickness of the partition wall (separation unit) of the pixel scintillator in a direction in which the pixels are arrayed is set to 40 μm. Meanwhile, the X-ray image G32 is an X-ray image after noise removal corresponding to the relationship between the pixel value and the standard deviation of noise values is executed in the X-ray image G31. In addition, in each simulation, the pixels of the two-dimensional sensor are set to have a rectangular shape with a side of 120 μm.

Hereafter, in the X-ray images G30, G31, and G32, the value indicating the magnitude of noise is the value of the standard deviation of intensity in the background portion (portion where black spots do not appear). The value indicating contrast is a difference between the average value of the intensity in the background portion and the minimum value of the intensity in the portion where the black spots appear. Further, the CN ratio (CNR: contrast to noise ratio) in the X-ray image G30, G31 and G32 is a value obtained by dividing the value indicating contrast by the value indicating the magnitude of noise. In the X-ray image G30, G31 and G32, the values indicating the magnitude of noise are 301.8, 1420.0, and 37.9, and the values indicating contrast are 3808.1, 9670.9, and 8844.3. In the X-ray image G30, G31 and G32, the CN ratios are 12.62, 6.81, and 233.16.

In the X-ray image G31 where the pixel scintillator is used, contrast is higher and noise is larger than in the X-ray image G30. In other words, the CN ratio in the X-ray image G31 is ½ times the CN ratio in the X-ray image G30. That is, an X-ray image from which noise is sufficiently removed cannot be acquired by using the pixel scintillator as the scintillator layer 11C alone. On the other hand, according to the third embodiment, for the X-ray image acquired after the pixel scintillator is used as the scintillator layer 11C, noise removal corresponding to the relationship between the pixel value and the standard deviation of noise values in the X-ray image is executed using the trained model 207C constructed in advance through machine learning. Thereby, in the X-ray image G32 according to the third embodiment, contrast increases and noise is reduced compared with the X-ray image G30. The CN ratio in the X-ray image G32 is 20 times the CN ratio in the X-ray image G30. That is, the image acquisition device 1C according to the third embodiment has the same conditions as the simulation conditions for the X-ray image G32, and thus it is possible to acquire an X-ray image from which noise is sufficiently removed.

In addition, in the control device 20C of the third embodiment, the noise distribution has a higher probability that the pixel value to which noise is added exceeds the original pixel value compared with the normal distribution. The pixel value to which noise is added along the noise distribution is calculated, and training image data is generated. The trained model 207C is constructed using the generated training image data. An X-ray image and a noise standard deviation map are input to the constructed trained model 207C, and image processing of removing noise from the X-ray image is executed. With such a configuration, image processing of removing noise from the X-ray image is executed considering that the X-rays detected by the sensor in image capturing using the scintillator appear as white spots in the X-ray image. As a result, in the image acquisition device 1C using the scintillator layer 11C, it is possible to acquire an X-ray image from which noise is more effectively removed.

[Supplemental Description of Construction Unit 206]

Figure 33:
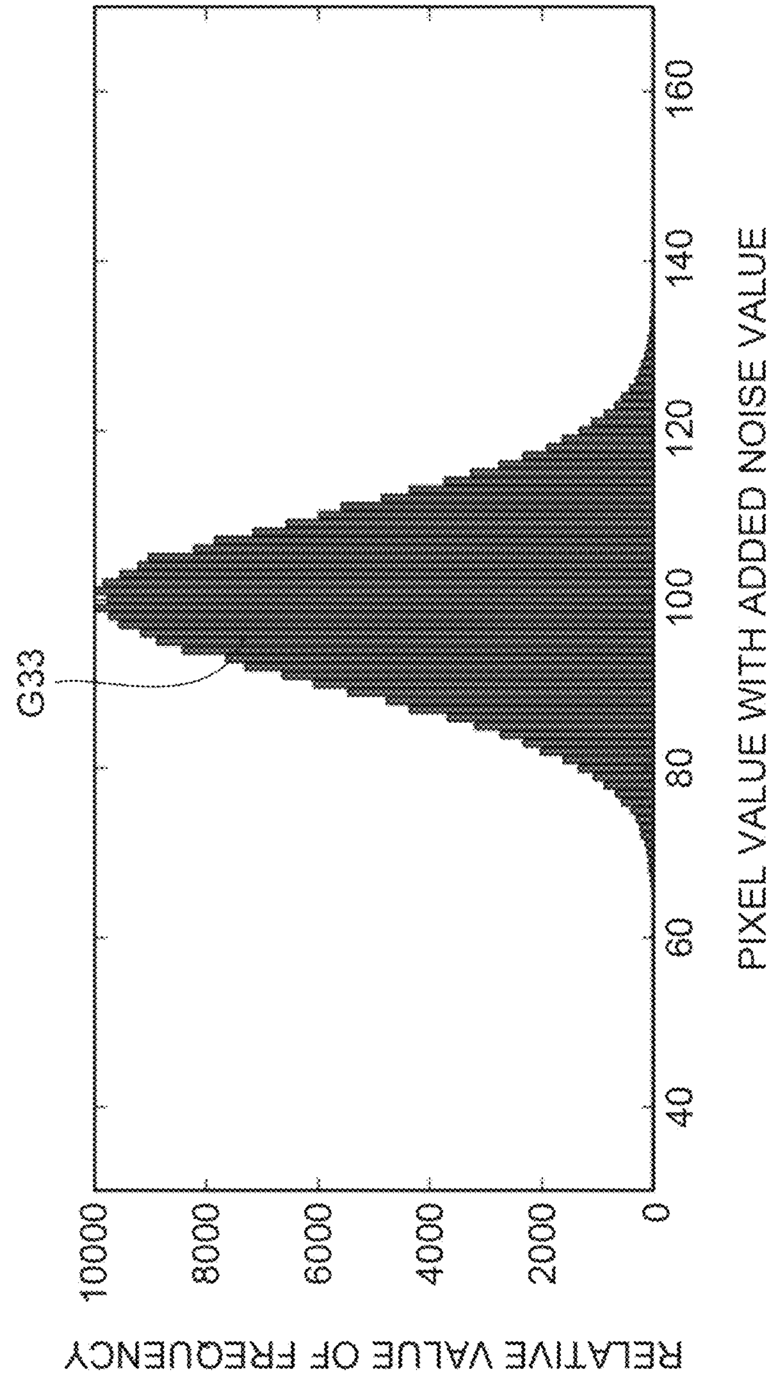
FIG. 33 is a graph illustrating an example of noise distribution used to generate training data.

The construction of the trained model 207 performed by the construction unit 206 is executed in the same way as the construction of the trained model 207C performed by the construction unit 206C. However, the noise distribution which is set in step S303 is not a noise distribution such as the noise distributions G28 and G29 described above, but a normal distribution. FIG. 33 is a diagram illustrating a normal distribution G33 used to generate training data. The horizontal axis in FIG. 33 indicates the pixel value to which the noise value is added with the pixel value before the noise value of a pixel is added being set to 100. The vertical axis in FIG. 33 is a relative value indicating the frequency of the noise pixel value.

Although various embodiments of the present disclosure have been described above, the embodiment of the present disclosure are not limited to the above embodiments. For example, the X-ray detection camera 10 is not limited to a dual-line X-ray camera, and may be a single line X-ray camera, a dual energy X-ray camera, a time delay integration (TDI) scan X-ray camera, a multi-line X-ray camera having a plurality of two or more lines, a two-dimensional X-ray camera, an X-ray flat panel sensor, an X-ray I.I, a direct conversion type X-ray camera (a-Se, Si, CdTe, CdZnTe, TlBr, PbI2, or the like) that does not uses a scintillator, an observation type camera using an optical lens with a scintillator based on lens coupling, a radiation-sensitive imaging tube, or a radiation-sensitive point sensor. In addition, the image acquisition device 1 is not also limited to the above embodiment, and may be a radiographic image processing system such as a computed tomography (CT) device that captured an image of the subject F in a stationary state. Further, the image acquisition device may be a radiographic image processing system that captures an image of the subject F while rotating the subject.

In addition, in the above-described embodiment, it is preferable that the noise map generation step includes deriving the evaluation value from average energy related to the radiation passing through the subject and the pixel value of each pixel in the radiographic image. In addition, in the above embodiment, it is preferable that the noise map generation unit derives the evaluation value from average energy related to the radiation passing through the subject and the pixel value of each pixel in the radiographic image. Here, in the comparative example, for example, when the average energy changes, the relationship between the pixel value and noise in the radiographic image fluctuates, and the noise cannot be sufficiently removed even with the trained model. In this regard, by adopting the above configuration, the spread of the noise value in the pixel value of each pixel in the radiographic image is evaluated in consideration of the average energy related to the radiation passing through the subject, and thus it is possible to realize noise removal corresponding to the relationship between the pixel value and the spread of noise in the radiographic image. As a result, it is possible to more effectively remove noise in the radiographic image.

In the above embodiment, it is also preferable to further include an input step of accepting an input of condition information indicating either conditions of a source of radiation or imaging conditions when the radiation is radiated to capture an image of the subject, and a calculation step of calculating the average energy on the basis of the condition information. In the above embodiment, it is also preferable to further include an input unit configured to accept an input of condition information indicating either conditions of a source of radiation or imaging conditions when the radiation is radiated to capture an image of the subject, and a calculation unit configured to calculate the average energy on the basis of the condition information. Further, it is also preferable that the condition information includes at least any one of a tube voltage of the source, information relating to the subject, information on a filter included in a camera used to capture an image of the subject, information on a filter included in the source, and information on a scintillator included in the camera used to capture an image of the subject. With such a configuration, the average energy of the radiation passing through the subject is calculated with a good degree of accuracy, and thus it is possible to realize noise removal corresponding to the relationship between the pixel value and the spread of noise. As a result, it is possible to more effectively remove noise in the radiographic image.

In the above embodiment, it is preferable to further include a calculation step of calculating the average energy from the pixel value of each pixel in the radiographic image. In the above embodiment, it is preferable to further include a calculation unit configured to calculate the average energy from the pixel value of each pixel in the radiographic image. With such a configuration, the average energy of the radiation passing through the subject is calculated with a good degree of accuracy for each pixel value of each pixel in the radiographic image, and thus it is possible to realize noise removal corresponding to the relationship between the pixel value of each pixel in the radiographic image and the spread of noise. As a result, it is possible to more effectively remove noise in the radiographic image.

In addition, it is preferable that the image acquisition step includes acquiring a radiographic image of a jig obtained by irradiating the jig with radiation and capturing an image of the radiation passing through the jig, and that the noise map generation step includes deriving the relationship data from the radiographic image of the jig. In addition, it is preferable that the image acquisition unit acquires a radiographic image of a jig obtained by irradiating the jig with radiation and capturing an image of the radiation passing through the jig, and that the noise map generation unit derives the relationship data from the radiographic image of the jig. With such a configuration, since the relationship data is generated on the basis of the radiographic image obtained by actually capturing an image of the jig and the noise map is generated, it is possible to realize noise removal corresponding to the relationship between the pixel value and the spread of noise. As a result, it is possible to more effectively remove noise in the radiographic image.

In addition, it is preferable that the image acquisition step includes acquiring a plurality of radiographic images without the subject, the noise map generation step includes deriving the relationship data from the plurality of radiographic images, and the plurality of radiographic images are a plurality of images that differ from each other in at least one of conditions of a source of radiation and imaging conditions. In addition, it is preferable that the image acquisition unit acquires a plurality of radiographic images without the subject, the noise map generation unit derives the relationship data from the plurality of radiographic images, and the plurality of radiographic images are a plurality of images that differ from each other in at least one of conditions of a source of radiation and imaging conditions. With such a configuration, since the relationship data is generated on the basis of the radiographic image obtained by actual image capturing and the noise map is generated, it is possible to realize noise removal corresponding to the relationship between the pixel value and the spread of noise. As a result, it is possible to more effectively remove noise in the radiographic image.

In addition, it is preferable that the evaluation value is the standard deviation of noise values. Thereby, since the spread of the noise value in the pixel value of each pixel in the radiographic image is evaluated more precisely, it is possible to realize noise removal corresponding to the relationship between the pixel value and noise. As a result, it is possible to more effectively remove noise in the radiographic image.

A machine-learning method according to the above embodiment includes a construction step of using a radiographic image as a training image and using a noise map generated from the training image on the basis of relationship data indicating a relationship between a pixel value and an evaluation value obtained by evaluating spread of a noise value, and noise-removed image data which is data obtained by removing noise from the training image, as training data, to construct a trained model that outputs the noise-removed image data on the basis of the training image and the noise map through machine learning. In the other aspect, it is preferable to further include a construction unit configured to use a training image which is a radiographic image, the noise map generated from the image on the basis of the relationship data, and noise-removed image data which is data obtained by removing noise from the training image, as training data, to construct a trained model that outputs the noise-removed image data on the basis of the training image and the noise map through machine learning. With such a configuration, the trained model used for noise removal in the radiographic image is constructed through machine learning using the training data. Thereby, when a radiographic image and a noise map generated from the radiographic image are input to the trained model, it is possible to realize noise removal corresponding to the relationship between the pixel value and the spread of noise. As a result, it is possible to more effectively remove noise in the radiographic image of the subject.

Alternatively, a trained model the above embodiment is constructed in the above construction step, the trained model causing a processor to execute image processing of removing noise from a radiographic image of a subject. In the other aspect, noise is removed from the radiographic image through machine learning in consideration of the spread of the noise value evaluated from the pixel value of each pixel in the radiographic image. This makes it possible to realize noise removal corresponding to the relationship between the pixel value and the spread of noise in the radiographic image using the trained model. As a result, it is possible to effectively remove noise in the radiographic image.

Further, a preprocessing method of the machine-learning method according to the above embodiment includes, in order to generate a noise map which is training data for the above machine-learning method, a noise map generation step of deriving the evaluation value from the pixel value of each pixel in the radiographic image on the basis of the relationship data indicating a relationship between the pixel value and the evaluation value obtained by evaluating the spread of the noise value, and generating a noise map that is data in which the derived evaluation value is associated with each pixel in the radiographic image. With such a configuration, the noise map which is training data for the above machine-learning method corresponds to the relationship between the pixel value and the evaluation value obtained by evaluating the spread of the noise value. Thereby, when a radiographic image and a noise map generated from the radiographic image are input to the trained model constructed using the above machine-learning method, it is possible to realize noise removal corresponding to the relationship between the pixel value and the spread of noise. As a result, it is possible to more effectively remove noise in the radiographic image of the subject.

REFERENCE SIGNS LIST

10 X-ray detection camera (imaging device)(camera)
12C Two-dimensional sensor (line sensor)(flat panel sensor)
20, 20A, 20B Control device (radiographic image processing module)
50 X-ray irradiator (radiation source)
201 Input unit
202, 202A Calculation unit
203, 203B Image acquisition unit
204, 204A, 204B Noise map generation unit
205 Processing unit
206 Construction unit
207 Trained model
G5 Noise standard deviation map (noise map)
G3, G23, G24, G25 Relational graph (relationship data) indicating correspondence relation between pixel values and standard deviation of Noise values
G7 Training image
G26 X-ray image (radiographic image) of jig
F Subject
P1 Member (jig)

The invention claimed is:

1. A radiographic image processing method comprising:
acquiring a radiographic image obtained by irradiating a subject with radiation and capturing an image of the radiation passing through the subject;
converting a pixel value of each pixel in the radiographic image into a standard deviation of a noise value on the basis of relationship data indicating a relationship between the pixel value and the standard deviation, and generating a noise standard deviation map that is data in which the converted standard deviation is associated with each pixel in the radiographic image; and
inputting the radiographic image and the noise standard deviation map in parallel to a trained model constructed in advance through machine learning and executing image processing of removing noise from the radiographic image.

2. The radiographic image processing method according to claim 1, wherein the acquiring of the radiographic image includes converting average energy related to the radiation passing through the subject and the pixel value of each pixel in the radiographic image into the standard deviation.

3. The radiographic image processing method according to claim 2, further comprising:
accepting an input of condition information indicating either conditions of a source of radiation or imaging conditions when the radiation is radiated to capture an image of the subject; and
calculating the average energy on the basis of the condition information,
wherein the condition information includes at least any one of a tube voltage of the source, information relating to the subject, information on a filter included in a camera used to capture an image of the subject, information on a filter included in the source, and information on a scintillator included in the camera.

4. The radiographic image processing method according to claim 2, further comprising calculating the average energy from the pixel value of each pixel in the radiographic image.

5. The radiographic image processing method according to claim 1, wherein the acquiring of the radiographic image includes acquiring a radiographic image of a jig obtained by irradiating the jig with radiation and capturing an image of the radiation passing through the jig, and the deriving of the evaluation value includes deriving the relationship data from the radiographic image of the jig.

6. The radiographic image processing method according to claim 1, wherein the acquiring of the radiographic image includes acquiring a plurality of radiographic images without the subject, the deriving of the evaluation value includes deriving the relationship data from the plurality of radiographic images, and the plurality of radiographic images are a plurality of images in which conditions of at least one out of conditions of a source of radiation and imaging conditions differ from each other.

7. A machine-learning method comprising:

converting a pixel value of each pixel in a radiographic image into a standard deviation of a noise value on the basis of relationship data indicating a relationship between the pixel value and the standard deviation, and generating a noise standard deviation map that is data in which the converted standard deviation is associated with each pixel in the radiographic image; and using the radiographic image as a training image and using the noise standard deviation map generated from the training image on the basis of the relationship data indicating the relationship between the pixel value and the standard deviation, and noise-removed image data which is data obtained by removing noise from the training image, as training data, to construct a trained model that outputs the noise-removed image data on the basis of the training image and the noise standard deviation map through machine learning.

8. A trained model constructed using the machine-learning method according to claim 7, the trained model causing a processor to execute image processing of removing noise from a radiographic image of a subject.

9. A radiographic image processing module comprising a processor configured to:

acquire a radiographic image obtained by irradiating a subject with radiation and capturing an image of the radiation passing through the subject;

convert a pixel value of each pixel in the radiographic image into a standard deviation of a noise value on the basis of relationship data indicating a relationship between the pixel value and the standard deviation, and generate a noise map that is data in which the converted standard deviation is associated with each pixel in the radiographic image; and input the radiographic image and the noise standard deviation map in parallel to a trained model constructed in advance through machine learning and execute image processing of removing noise from the radiographic image.

10. The radiographic image processing module according to claim 9, wherein the processor converts average energy related to the radiation passing through the subject and the pixel value of each pixel in the radiographic image into the standard deviation.

11. The radiographic image processing module according to claim 10, wherein the processor accept an input of condition information indicating either conditions of a source of radiation or imaging conditions when the radiation is radiated to capture an image of the subject, and the processor calculate the average energy on the basis of the condition information, wherein the condition information includes at least any one of a tube voltage of the source, information relating to the subject, information on a filter included in a camera used to capture an image of the subject, information on a filter included in the source, and information on a scintillator included in the camera used to capture an image of the subject.

12. The radiographic image processing module according to claim 10, wherein the processor calculate the average energy from the pixel value of each pixel in the radiographic image.

13. The radiographic image processing module according to claim 9, wherein the processor acquires a radiographic image of a jig obtained by irradiating the jig with radiation and capturing an image of the radiation passing through the jig, and derives the relationship data from the radiographic image of the jig.

14. The radiographic image processing module according to claim 9, wherein the processor acquires a plurality of radiographic images without the subject, and derives the relationship data from the plurality of radiographic images, and the plurality of radiographic images are a plurality of images in which conditions of at least one out of conditions of a source of radiation and imaging conditions differ from each other.

15. The radiographic image processing module according to claim 9, wherein the processor uses a training image which is a radiographic image, the noise map generated from the image on the basis of the relationship data, and noise-removed image data which is data obtained by removing noise from the training image, as training data, to construct a trained model that outputs the noise-removed image data on the basis of the training image and the noise map through machine learning.

16. A radiographic image processing program causing a processor to function as:

acquiring a radiographic image obtained by irradiating a subject with radiation and capturing an image of the radiation passing through the subject;

converting a pixel value of each pixel in the radiographic image into a standard deviation of a noise value on the basis of relationship data indicating a relationship between the pixel value and the standard deviation, and generating a noise map that is data in which the converted standard deviation is associated with each pixel in the radiographic image; and inputting the radiographic image and the noise standard deviation map in parallel to a trained model constructed in advance through machine learning and executing image processing of removing noise from the radiographic image.

17. A radiographic image processing system comprising:

the radiographic image processing module according to claim 9;

a source configured to irradiate the subject with radiation; and an imaging device configured to capture an image of the radiation passing through the subject and acquire the radiographic image.

18. The radiographic image processing system according to claim 17, wherein the imaging device has a line sensor.

19. The radiographic image processing system according to claim 17, wherein the imaging device has a two-dimensional sensor.

* * * * *